US009725723B2

(12) United States Patent
Hedtjarn et al.

(10) Patent No.: US 9,725,723 B2
(45) Date of Patent: Aug. 8, 2017

(54) COMPOSITIONS AND METHODS FOR MODULATION OF FGFR3 EXPRESSION

(71) Applicant: ROCHE INNOVATION CENTER COPENHAGEN A/S, Horsholm (DK)

(72) Inventors: Maj Hedtjarn, Horsholm (DK); Soren Ottosen, Horsholm (DK)

(73) Assignee: Roche Innovation Center Copenhagen A/S, Hoersholm (DK)

( * ) Notice: Subject to any disclaimer, the term of this patent is extended or adjusted under 35 U.S.C. 154(b) by 0 days.

(21) Appl. No.: 14/647,430

(22) PCT Filed: Nov. 25, 2013

(86) PCT No.: PCT/EP2013/074552
§ 371 (c)(1),
(2) Date: May 26, 2015

(87) PCT Pub. No.: WO2014/080004
PCT Pub. Date: May 30, 2014

(65) Prior Publication Data
US 2015/0307886 A1 Oct. 29, 2015

Related U.S. Application Data

(60) Provisional application No. 61/729,922, filed on Nov. 26, 2012.

(51) Int. Cl.
A61K 48/00 (2006.01)
C07H 21/02 (2006.01)
C07H 21/04 (2006.01)
C12N 15/11 (2006.01)
C12N 15/113 (2010.01)

(52) U.S. Cl.
CPC ...... C12N 15/1138 (2013.01); C12N 2310/11 (2013.01); C12N 2310/3231 (2013.01); C12N 2310/341 (2013.01); C12N 2310/351 (2013.01); C12N 2320/30 (2013.01); C12N 2320/34 (2013.01)

(58) Field of Classification Search
USPC .......................................... 514/44; 536/24.5
See application file for complete search history.

(56) References Cited

FOREIGN PATENT DOCUMENTS

| WO | WO03/023004 | 3/2003 |
| WO | WO2007/146511 | 12/2007 |
| WO | WO2009/090182 | 7/2009 |
| WO | WO2011/139842 | 11/2011 |
| WO | WO2014/080004 | 5/2014 |

OTHER PUBLICATIONS

Baujat et al., "Achondroplasia," Bailliere's Best Practice and Research, Clinical Reumatology, 22:3-18 (2008).
Silvie Foldynova-Trantirkova et al., "Sixteen years and counting: The current understanding of fibroblast growth factor receptor 3 (FGFR3) signaling in skeletal dysplasias," Human Mutation, 33:29-41 (2012).
International Preliminary Report and International Search Report, Written Opinion in corresponding Application No. PCT/EP2013/074552, dated May 26, 2015, pp. 1-10.

Primary Examiner — Terra C Gibbs
(74) Attorney, Agent, or Firm — Fish & Richardson P.C.

(57) ABSTRACT

Disclosed are oligonucleotides which target and hybridize to nucleic acid molecules encoding FGFR3, leading to reduced expression of FGFR3. Reduction in the aberrant expression of FGFR3 is beneficial for the treatment of certain medical disorders, such as achondroplasia.

14 Claims, 11 Drawing Sheets

FIG. 4 (con't)
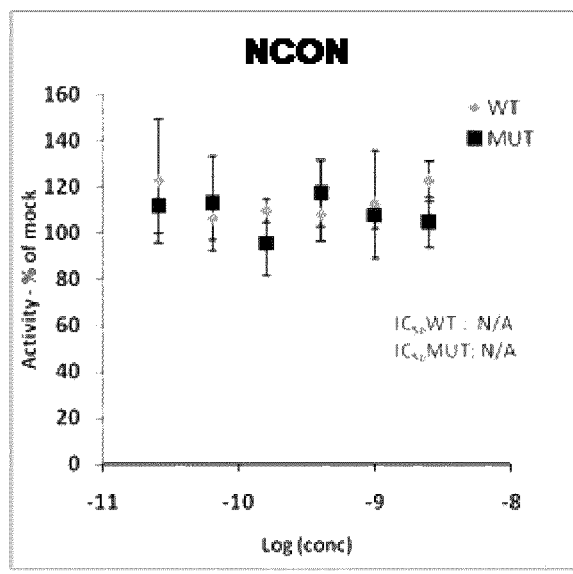

COMPOSITIONS AND METHODS FOR MODULATION OF FGFR3 EXPRESSION

This application is the U.S. national stage under 35 USC §371 of International Application Number PCT/EP2013/074552, filed on 25 Nov. 2013, which claims priority to U.S. Application No. 61/729,922, filed on 26 Nov. 2012, the entire contents of which is hereby incorporated by reference.

FIELD

The present application relates to oligonucleotides and related pharmaceutical compositions that target and hybridize to nucleic acids encoding fibroblast growth factor receptor type 3 (FGFR3) and to methods of using the oligonucleotides to modulate expression of FGFR3. In particular, certain embodiments are directed to antisense oligonucleotides that hybridize with nucleic acids, such as mRNA, encoding FGFR3 and to methods for modulating the expression of FGFR3 with such antisense oligonucleotides. Reduction of FGFR3 expression is beneficial for a range of medical disorders, such as achondroplasia.

BACKGROUND

Fibroblast growth factor receptors (FGFR) are high-affinity receptors for the fibroblast growth factors. These factors have a diverse role in cell growth, differentiation and other biological processes, their precise function being dependent on the target cell and development stage. It has been found that mutations in the FGFR genes cause a variety of disorders. For example, FGFR1 and FGFR2 mutations occur in craniosynostoses, and mutations in FGFR3 have been implicated in skeletal dysplasias such as achondroplasia, hypochondroplasia and thanatophoric dysplasia (types I and II).

Current therapies for the treatment of dysplasias such as achondroplasia include orthopedic surgeries such as artificial hip joint replacement or leg lengthening and growth hormone therapy. Leg lengthening involves cutting bones at the age of ten years or after and gradually increasing body height using a special leg lengthening device over several courses of about six months. However, this procedure inflicts great pain on patients. Growth hormone therapy increases body height by means of periodic growth hormone injections starting from childhood. However, growth ceases when injections are stopped. Neither of the foregoing therapies is curative, nor is either considered ideal from the viewpoint of a patient's quality of life. Further developments are needed to identify novel therapies for the treatment of achondroplasia, such as treatments which modulate the expression of FGFR3 as a means of curing, or at least improving the survival and morbidity associated with, achondroplasia in humans.

SUMMARY

The present application provides novel oligonucleotides, particularly locked nucleic acid (LNA) antisense oligonucleotides, and therapeutic interventions useful for the treatment of diseases associated with the aberrant expression of FGFR3 (e.g., dysplasias such as achondroplasia). The inventions disclosed herein relate to the discovery that contacting cells or tissues aberrantly expressing FGFR3 with the oligonucleotides of the present invention modulates the expression of FGFR3 (and in particular mutated or naturally occurring variants of FGFR3). In particular embodiments, modulating the expression of FGFR3, for example, restores normal chondrocyte function. The oligonucleotides of the present invention and the methods of using such oligonucleotides to modulate the aberrant expression of FGFR3 provide a means of improving the survival and morbidity associated with, or even curing, aberrant expression of FGFR3 such as, for example, achondroplasia.

In one aspect, the invention relates to oligonucleotides of from about 8 to about 50 nucleotides in length which hybridize to an FGFR3 target sequence, e.g., a mammalian FGFR3 gene or mRNA sequence (e.g., a naturally-occurring FGFR3 gene or mRNA). In certain aspects such oligonucleotides hybridize to an FGFR3 target sequence with sufficient stability (e.g., with sufficient hybridization strength and for a sufficient period of time) to inhibit expression of an FGFR3 gene product (e.g., an FGFR3 protein). Oligonucleotides which are particularly suitable for this purpose and others are described herein.

The term hybridize as used herein is understood as capable of hybridising.

In one aspect, the present invention provides oligonucleotides of from about 8 to about 50 nucleotides in length (e.g., from about 8 to 30, 8 to 20, 12 to 18, or 14 to 16 nucleotides in length) which comprise a contiguous nucleotide sequence (a first region) of from about 8 to about 30 nucleotides (e.g., about 8, 9, 10, 11, 12, 13, 14, 15, 16, 17, 18, 19, 20, 21, 22, 23, 24, 25, 26, 27, 28, 29, or 30 nucleotides in length) having at least 80% identity (e.g., at least about 85%, 90%, 95%, 96%, 97%, 98%, 99% or 100% identity) with a region corresponding to the reverse complement of the coding region of a mammalian FGFR3 gene or the complement of mRNA encoding FGFR3. For example, the oligonucleotides of the present invention may comprise a contiguous nucleotide sequence which is at least 80% complementary to a portion of a nucleic acid sequence encoding FGFR3 (e.g., FGFR3 DNA, pre-mRNA or mRNA). The oligonucleotides disclosed herein may comprise a nucleic acid sequence that is complementary to a region of a mutated FGFR3 gene or to the corresponding mRNA. Similarly, the oligonucleotides disclosed herein may comprise a sequence that is complementary to the gene product of an FGFR3 gene (e.g., mRNA encoded by the FGFR3 gene) or a polymorph or naturally-occurring variant thereof that encodes a mutation such as a glycine to arginine substitution at position 380 of the FGFR3 gene product (referred to herein as G380R), as is encoded for example by SEQ ID NO: 4, or naturally-occurring variants thereof (e.g., SNP ID's rs28931614, rs11943863 or rs17881656). In particular, the oligonucleotides described herein may be at least 80% complementary (e.g., at least 85%, 90%, 95%, 96%, 97%, 98%, 99% or more complementary) to a nucleic acid sequence encoding a mutated region of an FGFR3 gene or mRNA, such as a region encoding the G380R mutation and the regions immediately upstream and/or downstream of the region encoding the G380R mutation (e.g., about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250 or more nucleotides upstream and/or downstream from the location of the G380R mutation).

In another aspect, the invention provides oligonucleotides comprising about 8 to about 20 nucleotides, wherein the oligonucleotides hybridize to at least an 8-nucleobase portion of a nucleic acid encoding FGFR3 (e.g., FGFR3 mRNA). For example, in some embodiments the oligonucleotides of the present invention hybridize to the nucleic acids (i.e., mRNA) encoding the G380R mutation, or to a region immediately surrounding and/or adjacent to the nucleic acids encoding the FGFR3 G380R mutation at position 1138 of codon 380. In some embodiments, the oligonucleotides are complementary to a region of a single stranded nucleic acid molecule encoding FGFR3, such as, for example a region of a nucleic acid molecule having the sequence of a portion of SEQ ID NO: 4 or naturally occurring variants thereof (e.g., SNP ID's rs28931614, rs11943863 or rs17881656).

In some embodiments, the claimed oligonucleotides comprise a sequence which is complementary to a DNA sequence encoding FGFR3 mRNA or a portion thereof, or alternatively the claimed oligonucleotides hybridize to an RNA sequence (e.g., pre-mRNA or mRNA) or portion thereof encoded thereby. When brought into contact with targeted cells or tissues (e.g., the chondrocytes in the growth plate of long bones of a patient affected by or afflicted with achondroplasia) the oligonucleotides disclosed herein can selectively reduce the expression of FGFR3 (and in particular mutated or aberrantly expressed FGFR3), thereby restoring normal chondrocyte function. For example, the oligonucleotides of the present invention can target the nucleic acids (e.g., mRNA) encoding mutated or aberrantly expressed FGFR3, such as, for example, the mRNA comprising or encoded by SEQ ID NO: 15, SEQ ID NO: 16, SEQ ID NO: 17, SEQ ID NO: 18, SEQ ID NO: 19 and/or SEQ ID NO: 20, or a particular portion or region of any of the foregoing (e.g., the region encoding the G380R mutation) and thereby modulate the expression of FGFR3, such that expression is reduced and/or inhibited by at least about 10%, 20%, 25%, 35%, 40%, 50%, or preferably at least 60%, 65%, 70%, 75%, 85%, 90%, 95%, 99% or 100%.

In yet another aspect, the invention provides compositions comprising oligonucleotides such as those described herein. In some embodiments, the compositions can include a pharmaceutical composition comprising one or more oligonucleotides described herein together with one or more pharmaceutically acceptable excipients, adjuvants, or other molecules to facilitate or improve the delivery or stability of the composition. In some embodiments, the inventions provide for a conjugate comprising one or more oligonucleotides described herein and at least one non-nucleotide or non-polynucleotide moiety attached, for example, covalently or non-covalently attached, to said oligonucleotide. Also disclosed herein are oligonucleotides and conjugates and pharmaceutical compositions comprising the same for use as a medicament, such as for the treatment of diseases associated with the aberrant expression of FGFR3 (e.g., dysplasias such as achondroplasia), and methods of treating such diseases by administering the oligonucleotides, conjugates and/or pharmaceutical compositions described herein to a mammalian subject, for example, a human subject such as a paediatric human subject (before or after birth) or an adult human subject.

In another aspect, the inventions provide for the use of an oligonucleotide or a conjugate thereof for the manufacture of a medicament for the treatment of achondroplasia. The invention also provides for methods of treating diseases or conditions associated with the aberrant expression of FGFR3, such as achondroplasia, the methods comprising the steps of administering an effective amount of an oligonucleotide, a conjugate and/or a pharmaceutical composition according to the invention, to a patient suffering from, likely to suffer from or otherwise affected by or afflicted with achondroplasia (e.g., such as a human paediatric or adult patient suffering from or susceptible to achondroplasia). In some embodiments, the disease, disorder or condition associated with the aberrant expression of FGFR3 relates to the over-expression of FGFR3, and in particular the over-expression of the mutated FGFR3 (e.g., FGFR3 comprising the G380R missense mutation). In some embodiments, the oligonucleotides, conjugates and pharmaceutical compositions described herein preferentially modulate the expression of an FGFR3 mutant or polymorph or naturally occurring variant, such as for example an FGFR3 mutant, polymorph or naturally occurring variant which comprises a glycine to arginine substitution at position 380 (G380R), (e.g., as is encoded by SEQ ID NO: 4 or SNP ID's rs28931614, rs11943863 or rs17881656). Such preferential modulation of the expression of an FGFR3 mutant, polymorph or naturally occurring variant by the oligonucleotides of the present invention may be partial or absolute in nature relative to the expression of wild-type FGFR3 (e.g., as is encoded by SEQ ID NO: 1). For example, when administered to a patient with heterozygous achondroplasia, the oligonucleotides of the present invention may target both mRNA encoding wild-type FGFR3 and mRNA encoding a mutated FGFR3 polymorph or naturally occurring variant, however such oligonucleotides may modulate the expression of each target to a varying extent, such that, for example, the expression of the mutated FGFR3 polymorph or variant is modulated to a greater extent than is the expression of the wild-type FGFR3. The oligonucleotides of the present invention may, for example, target and reduce the expression of a mutated FGFR3 polymorph that comprises a G380R substitution (e.g., as is encoded by SEQ ID NO: 4 or SNP ID's rs28931614, rs11943863 or rs17881656) by a factor of 2, 4, 8, 10, 15, 25, 50, 75, 100 or more; while the same oligonucleotide respectively reduces the expression of a wild-type FGFR3 (e.g., as encoded by SEQ ID NO: 1) by a factor of 1, 2, 4, 5, 10, 15, 25, 50, 75, 100 or more. Similarly, the oligonucleotides of the present invention may, for example, target and reduce the expression of a mutated FGFR3 polymorph or variant that comprises a G380R mutation (e.g., as is encoded by SEQ ID NO: 4 or SNP ID's rs28931614, rs11943863 or rs17881656) by about 1%, 2.5%, 5%, 10%, 20%, 35%, 40%, 50%, 60%, 75%, 80%, 85%, 90%, 95%, 97.5%, 99% or more; while the same oligonucleotide reduces the expression of a wild-type FGFR3 (e.g., as encoded by SEQ ID NO: 1) by about 1%, 2.5%, 5%, 10%, 20%, 35%, 40%, 50%, 60%, 75%, 80% or 90%. Also disclosed herein are oligonucleotides which target and/or hybridize to nucleic acids encoding mutated FGFR3 on a discriminatory basis relative to nucleic acids that encode functional or wild-type FGFR3. For example, in a patient with heterozygous achondroplasia or cancer, such as bladder cancer the oligonucleotides of the invention may target and reduce the expression of a mutated FGFR3 allele by about 1%, 2.5%, 5%, 10%, 20%, 35%, 40%, 50%, 60%, 75%, 80%, 90%, 95%, 97.5%, 99%, or more relative to the expression of a functional or wild-type FGFR3 allele. Alternatively, the oligonucleotides of the present invention may increase the ratio of expression of a wild-type FGFR3 gene product or mRNA (e.g., in a paediatric patient affected by heterozygous achondroplasia) to the expression of a mutated FGFR3 gene product or mRNA. In some embodiments the oligonucleotides, conjugates and pharmaceutical compositions reduce or otherwise inhibit expression of mutated FGFR3 (e.g., by preferentially targeting and hybridizing to nucleic acids (e.g., mRNA) which encode the FGFR3 G380R mutation in an allele of a patient with heterozygous achondroplasia), while not affecting or minimally affecting the expression of FGFR3 which does not encode the mutation.

In some embodiments, the oligonucleotides disclosed herein hybridize to the gene product of FGFR3 (i.e., mRNA), for example, the mRNA gene product encoded by a mutated FGFR3 polymorph or variant which comprises a glycine to arginine substitution at position 380 (e.g., as is encoded by SEQ ID NO: 4). In other embodiments, the oligonucleotides hybridize to the gene products (e.g., mRNA) of the nucleic acids encoding a mutated FGFR3 polymorph or variant, where the nucleotides encoding such FGFR3 polymorph comprise a guanine to adenine transition substitution at position 1394 of codon 380. In other embodiments, the oligonucleotides of the present invention may specifically hybridize to gene products of the nucleic acids (i.e., mRNA) encoding the mutated FGFR3 G380R polymorph or variant (e.g., as is encoded by SEQ ID NO: 4), while the same oligonucleotide does not hybridize to the gene products of the nucleic acids (i.e., mRNA) encoding the wild-type FGFR3 (e.g., as is encoded by SEQ ID NO: 1). Such preferential or discriminatory hybridization of the oligonucleotides to the nucleic acids encoding the mutated FGFR3 G380R polymorph, can modulate the expression of the mutant gene product while the expression of the wild-type FGFR3 gene product is preserved or otherwise remains unchanged. For example, the oligonucleotides of the present invention may target and preferentially hybridize to mRNA comprising or encoded by a nucleic acid comprising SEQ ID NOS: 15-20 (or a fragment thereof), such that the expression of the protein encoded by such mRNA is reduced and/or inhibited by at least about 10%, 20%, 25%, 35%, 40%, 50%, or preferably at least 60%, 65%, 70%, 75%, 85%, or most preferably at least 90%, 95%, 99% or 100%.

In some embodiments, the oligonucleotides of the present invention hybridize to the nucleic acids (e.g., mRNA) encoding human FGFR3 (e.g., the FGFR3 mRNA encoded by Accession Number NM_000142, inclusive of any variants and polymorphs thereof) where such oligonucleotides do not cross-hybridize to the nucleic acids encoding FGFR3 of other species. For example, the oligonucleotides of the present invention may target and hybridize to the human FGFR3 mRNA (e.g., as is encoded by SEQ ID NO: 1 and/or SEQ ID NO: 4) and not hybridize to the mouse FGFR3 mRNA (e.g., as is encoded by SEQ ID NO: 7) or the rat FGFR3 mRNA (e.g., as is encoded by SEQ ID NO: 8). Also contemplated are oligonucleotides that preferentially hybridize to one or more of FGFR3 mRNA target sequences that comprise or are encoded by SEQ ID NO: 15, SEQ ID NO: 16, SEQ ID NO: 17, SEQ ID NO: 18, SEQ ID NO: 19 or SEQ ID NO: 20. The oligonucleotides of the present invention may preferably hybridize to human FGFR3 mRNA which encodes a G380R mutation or to a fragment thereof (e.g., the FGFR3 mRNA encoded by Accession Number NM_000142) while not cross-hybridizing to FGFR3 mRNA of the mouse or rat FGFR3 gene, and thus modulate the expression of the targeted human FGFR3. Alternatively, the same oligonucleotide may specifically hybridize to the nucleic acids encoding an FGFR3 polymorph which encodes a G380R mutation, but may not hybridize to the nucleic acids encoding the wild-type of the human, mouse or rat species which lacks or does not otherwise encode that G380R mutation under the same or similar stringency conditions.

Also provided are methods of inhibiting the aberrant expression of FGFR3, and in particular methods of inhibiting the aberrant expression of the gene products of the mutated FGFR3 gene (e.g., mRNA encoding FGFR3), in a cell (e.g., a chondrocyte or a bladder cell) which is expressing a mutated FGFR3. In some embodiments, the method comprises administering an oligonucleotide, conjugate or pharmaceutical composition according to the invention to a patient, or otherwise contacting a cell or tissue with such oligonucleotide, conjugate or pharmaceutical composition so as to inhibit the expression of FGFR3 (e.g., FGFR3 comprising the G380R mutation) in such patient or cell.

Also disclosed are oligonucleotides of from about 8 to 50 monomers, which comprise a first region of about 8 to 50 contiguous monomers (e.g., nucleotides), wherein the sequence of such first region is at least 80% identical (e.g., at least 85%, at least 90%, at least 95%, at least 99% identical) to one or more selected target sequences (e.g., a target sequence comprising mRNA encoding mutated FGFR3). In some embodiments, the selected target sequences may comprise a region of nucleic acids encoding mammalian FGFR3 (e.g., mRNA) or a fragment thereof. Further provided are antisense oligonucleotides, for example, 8 to 50, 12 to 30 or 12 to 20 nucleotides in length. For example, in some embodiments the oligonucleotides comprise one or more locked nucleic acid (LNA) residues or monomeric units (e.g., SEQ ID NO: 21, SEQ ID NO: 22, SEQ ID NO: 23, SEQ ID NO: 24 or SEQ ID NO: 25). Where the oligonucleotides of the present invention comprise two or more LNA monomeric units (e.g., two or more β-D-oxy-LNA monomeric units), such LNA monomeric units may be located consecutively relative to each other, or alternatively such LNA monomeric units may be located non-consecutively relative to each other. For example, disclosed herein are antisense oligonucleotides comprising SEQ ID NO: 14, wherein the oligonucleotides modulate expression of FGFR3, and wherein the oligonucleotides comprise at least one locked nucleic acid at one or more positions selected from the group consisting of: (a) the guanine nucleotide at position 1 is an oxy-LNA; (b) the adenine nucleotide at one or more of positions 2 and 3 is an oxy-LNA; (c) the cytosine nucleotide at one or more of positions 10 and 11 is an oxy-LNA; and (d) the thymine nucleotide at position 12 is an oxy-LNA.

Optionally, such locked antisense oligonucleotides may comprise one or more sugar substitutions, such as for example, a 2'-O-methoxyethyl sugar substitution. Also provided herein are conjugates which comprise one or more of the oligonucleotides according to the invention, wherein such oligonucleotides comprise at least one non-nucleotide or non-polynucleotide moiety which is covalently attached to the oligonucleotide of the invention.

Also provided are pharmaceutical compositions which comprise one or more of the oligonucleotides or the conjugates according to the invention, and a pharmaceutically acceptable diluent, carrier, solvent, salt or adjuvant. Also provided are pharmaceutical compositions which comprise one or more of the oligonucleotides of the invention. Such pharmaceutical compositions may be administered, for example, parenterally by injection or infusion directly to the target site of action or may be administered by inhalation, peritoneally, topically or orally.

Further provided are methods of down-regulating the expression of aberrantly expressed FGFR3 (e.g., at the mRNA level), and in particular down-regulating the expression of mutant or naturally-occurring variants of FGFR3 (e.g., G380R, or a mutation characterising a cancer, such as bladder cancer), in cells or tissues. Such methods comprise contacting the cells or tissues, in vitro or in vivo, with an effective amount of one or more of the oligonucleotides, conjugates or compositions of the invention. In some embodiments, the oligonucleotides and compositions of the present invention are capable of down-regulating the expression of mutated or aberrantly expressed FGFR3 in a mammal (e.g., in a human patient suffering from or otherwise affected by cancer, such as bladder cancer or heterozygous achondroplasia) while not modulating or otherwise affecting the expression of a normally functioning or wild-type allele.

Also disclosed are methods of treating an animal (e.g., a non-human animal or a human) suspected of having, or susceptible to, a disease or condition, associated with the aberrant expression, or over-expression of FGFR3 by administering to the animal a therapeutically or prophylactically effective amount of one or more of the oligonucleotides, conjugates or pharmaceutical compositions described herein. Furthermore, provided herein are methods of using oligonucleotides to inhibit the expression of mutated or aberrantly expressed FGFR3 (e.g., mutated or naturally-occurring variants of FGFR3), and for the treatment of diseases associated with the aberrant expression or activity of FGFR3.

Also provided are methods of treating conditions associated with the aberrant expression of FGFR3 (e.g., cancers or dysplasias such as achondroplasia). Also provided are methods of restoring chondrocyte function, comprising delivering to, or contacting chondrocyte cells aberrantly expressing FGFR3, with one or more of the oligonucleotides of the present invention. The conditions under which the claimed method introduces the oligonucleotides to the chondrocyte cells are sufficient to reduce aberrant FGFR3 expression in the chondrocyte cells, and thereby restore normal cell function. In some embodiments, such methods preferentially reduce the expression of a FGFR3 mutant, polymorph or naturally-occurring variant which comprises a guanine to adenine transition substitution at position 1138 of codon 380 (which corresponds to nucleotide position 1394 of the sequence encoded by SEQ ID NO: 4) at the mRNA level. The invention provides for methods of treating a disease such as cancer, such as bladder cancer or achondroplasia, the method comprising administering an effective amount of one or more oligonucleotides, conjugates, or pharmaceutical compositions thereof to a patient in need thereof (e.g., a human paediatric patient affected by achondroplasia). The invention provides for methods of inhibiting (e.g., by down-regulating) the expression of mutated or aberrantly expressed FGFR3 in a cell or a tissue, the method comprising the step of contacting the cell or tissue with an effective amount of one or more oligonucleotides disclosed herein or conjugates or pharmaceutical compositions thereof, to thereby down-regulate the expression of the mutated or aberrantly expressed FGFR3 (e.g., at the mRNA level).

The above discussed, and many other features and attendant advantages of the present invention will become better understood by reference to the following detailed description of the invention when taken in conjunction with the accompanying examples.

BRIEF DESCRIPTION OF THE FIGURES

As illustrated in FIG. 3, all ten oligonucleotides were found to produce a dose-dependent knock-down of the MUT reporter construct in the concentration ranges evaluated relative to the WT reporter construct.

As illustrated in FIGS. 5A and 5B, the effect of each of the ten oligonucleotides on the non-specific SCA3 and PTEN targets is significantly lower than the effect on the FGFR3 target.

As illustrated in FIG. 6, most of the ten oligonucleotides did not produce any appreciable degradation products.

DETAILED DESCRIPTION

Figure 1A:
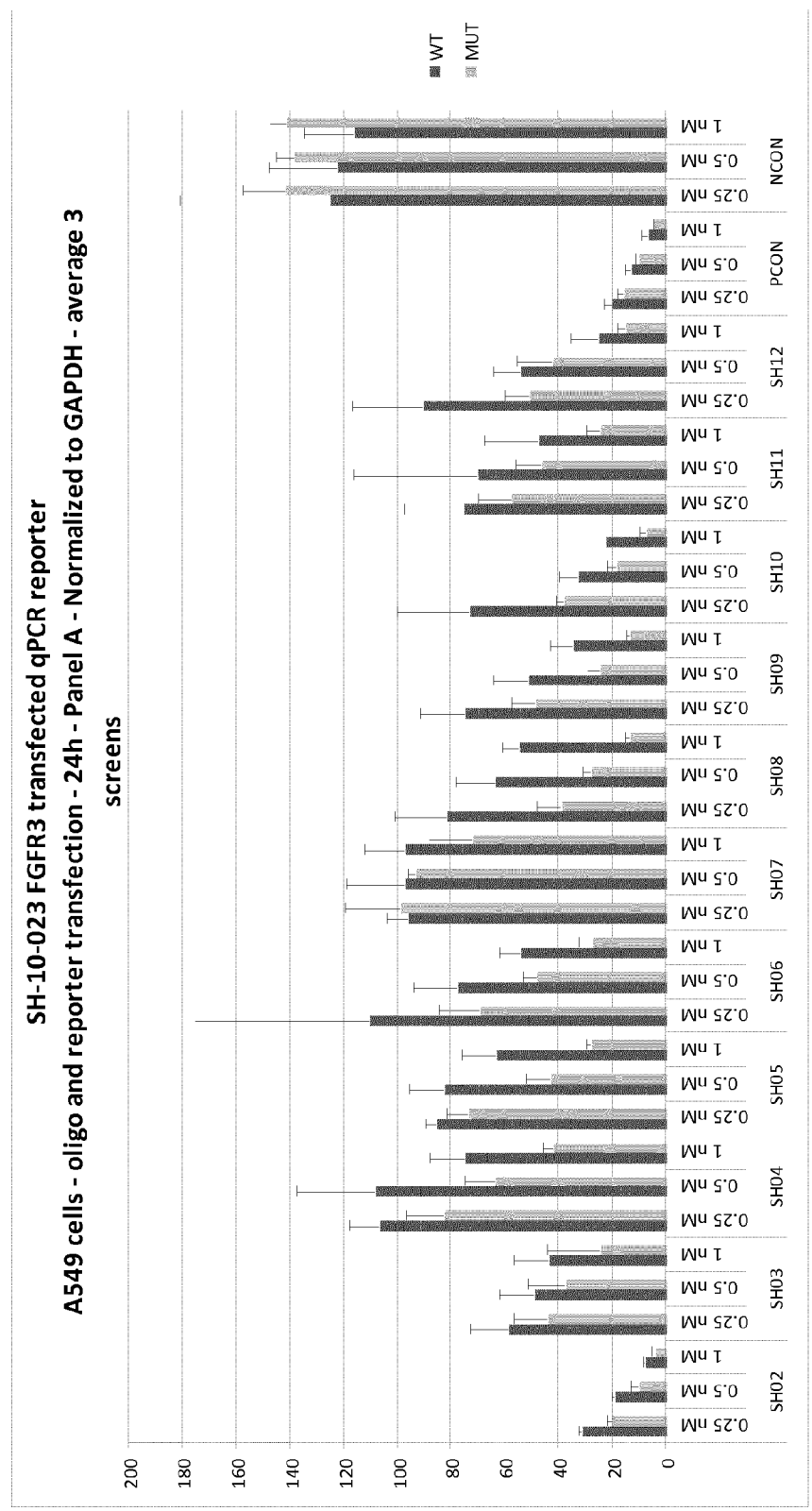
FIGS. 1A and 1B illustrate flag-tagged wild-type (WT) and mutant (MUT) reporter levels in A549 cells transfected with 21 different oligonucleotides complementary to portions of the region including and surrounding the nucleotides encoding the FGFR3 G380R mutation. The human A549 cells were co-transfected with each oligonucleotide and either the WT or MUT reporter construct. The cells were then harvested 24 hours after transfection, and the level of the flag-tagged reporter transcript was determined using a reporter-specific quantitative PCR assay. The results are expressed as percentage of the mock-treated samples. The results are reported as the average of three independent studies per oligonucleotide, and the error bars indicate the standard deviation. As illustrated in both FIGS. 1A and 1B, each of the 21 test oligonucleotides showed reduced expression of, and preferentially targeted, the MUT reporter construct relative to the WT reporter construct.

The oligonucleotides described herein provide specific therapeutic tools capable of modulating the expression of FGFR3. In some embodiments, the short (e.g., usually about less than 50, 40, 30, 20, 18, 17, 16, 15, 14, 13, 12, 10, 8 or less nucleotides in length) single-stranded synthetic oligonucleotides described herein have a base sequence complementary to the FGFR3 RNA target sequence (e.g., pre-mRNA or mRNA) and form a hybrid duplex by hydrogen bonded base pairing. For example, in some embodiments the oligonucleotides of the present invention may target or be complementary to nucleic acids encoding FGFR3 (e.g., mRNA encoding FGFR3) or a fragment thereof (e.g., SEQ ID NOS: 5 or 6) and thereby modulate the expression of FGFR3. In other embodiments, the oligonucleotides of the present invention may generally work by a cleavage mode of action or sterically blocking enzymes involved in processing pre-mRNA or translation of mRNA. This hybridization can be expected to prevent expression, (i.e., translation of the target mRNA code into its protein product) and thus preclude subsequent effects of the protein product. Accordingly, the oligonucleotides and methods described herein can be used to ameliorate or treat one or more conditions (e.g., diseases or syndromes) associated with the aberrant expression of FGFR3, for example, cancer, such as bladder cancer, skeletal dysplasias such as achondroplasia, hypochondroplasia and thanatophoric dysplasia (types I and II).

Achondroplasia, which is the most common form of human dwarfism, is caused by a point mutation in the transmembrane domain of the FGFR3 gene. Hypochondroplasia and thanatophoric dysplasia (types I and II) are also due to single mutations in the FGFR3 gene. In affected patients, body proportions and physical features are abnormal at birth, which in most cases forms the basis of diagnosis usually at or soon after birth. The signs of dwarfism become steadily more apparent with age. Overall, most patients have a relatively normal life, with cardiovascular complications, spinal cord obstruction, and upper airway obstruction being the most severe effects. The incidence of achondroplasia is approximately 1 in 110,000 to 1 in 130,000 live births.

The clinical features of heterozygous achondroplasia are very consistent among patients, and include proximal shortening of the extremities, midface hypoplasia, narrowing of the spinal column and relative macrocephaly. Final achondroplasia adult height ranges between 112-145 cm. Histologically, the epiphyseal and growth plate cartilage of achondroplasia patients have a normal. However, morphometric examinations of such patients have revealed that the growth plate is shorter than normal and that the shortening is greater in homozygous than in heterozygous achondroplasia, suggesting a gene dosage effect. The intercolumnar matrix of achondroplasia patients is more abundant than normal and focus of vascularization and transverse tunneling of the cartilage (ingrowth of blood vessels) has been observed in some cases. In addition, marked periosteal bone formation has been observed. The underlying mechanism of achondroplasia is believed to be a defect in the maturation of long bones growth plate chondrocytes.

The role of the FGFR3 gene in the growth plate appears to be one of negative regulation of intrinsic growth rates. In particular, mice that are homozygous for FGFR3 null alleles (e.g., by gene knock-out) show kyphosis, scoliosis, overgrowth of long bones and enlargement of the hypertrophic zone of growth plates. This phenotype is consistent with a role of FGFR3 in regulating chondrocyte proliferation (upper-hypertrophic cells) and final differentiation (lower-hypertrophic cells) at the growth plates of tubular long bones and at the sutures of the skull.

Achondroplasia is inherited in an autosomal dominant fashion, and can be caused by gain-of-function mutations in the expression of FGFR3. Reports have shown that achondroplastic patients can have mutations in FGFR3 located at chromosome 4p16.3. Two of the mutations in the FGFR3 gene have been shown to cause more than 99% of achondroplasia cases. Of these two mutations, approximately 97% relate to a G1138A mutation in exon 8 of the FGFR3 gene, and approximately 2.5% relate to a G1138C mutation in exon 8 of the FGFR3 gene. The G1138A mutation is also referred to as 1394 G>A mutation, when mapped to current genbank entry for FGFR3 NM_000142.4 (SEQ ID NO:1) or as 1138 G>A, when mapped to the obsolete genbank entry NM_000142.1. The latter nomenclature, although obsolete, is maintained in the bulk of the literature, including present-day publications. The 1394 and 1138 position are used interchangeably herein. Both the G1138A and the G1138C mutations can result in a change of the amino acid Glycine at the codon 380 position to Arginine (sometimes referred to as the "G380R" mutation) in the FGFR3 amino acid sequence. Other disease causing mutations in FGFR3 include a Gly 375 to Cys mutation which lies in the transmembrane domain of FGFR3 and a Gly 346 to Glu mutation within the Ig3-TM linker region of FGFR3.

In addition to achondroplasia, mutations and changes in expression levels of FGFR3 has been shown to be strongly correlated to bladder cancer. Approximately 75% of low-grade, non-muscle invasive papillary bladder tumors have been shown to contain activating mutations in FGFR3. In muscle invasive tumors, although the prevalence of activating mutations in FGFR3 is lower (20%), expression levels of FGFR3 are increased in 50% of tumors, leading to higher FGFR3 activity. The correlation between either activating mutations or increased expression levels of FGFR3 and tumor formation supports a model where cancer cell proliferation is driven by increase in FGFR3 activity. This is supported by in vitro and in vivo experiments where small molecule inhibitors and antibodies directed against FGFR3 can reduce cell proliferation in in vitro models of bladder cancer and significantly reduce tumor size in rodent models of bladder cancer.

Treatment of bladder cancer is currently based on resection of the tumors, a method that is plagued by a high rate of recurrence, leading to progression and metastasis of the cancer. The resection is often followed by chemotherapy and, if the cancer becomes muscle invasive, by removal of the bladder. Intravesicular treatment of the cancer by an FGFR3-directed therapy may reduce or eliminate the need for tumor resection and reduce the rate of cancer progression and metastasis.

A number of specific FGFR3 mutations, such as these indicated in the Table below have been identified in clinical isolates of bladder cancer. In general, these mutations are activating mutations, which affect dimerization of FGFR3, activation or signaling by FGFR3 and often results in ligand independent growth of the tumor cells. FGFR3-directed antisense oligonucleotides may be used against the specific mutations, to minimize side effects mediated through the loss of wild-type FGFR3 function, or may be used against a site in the transcript distal from the mutation, allowing for treatment of cancers where the mutation renders the cancer resistant to small molecules or antibodies.

TABLE

Known nucleotide and amino acid changes in human bladder tumors. Nucleotides and amino acids are mapped on the NM_000142.1 sequence. Amino acids in parenthesis refer to the same amino acid changes, reported in the literature, but mapped to a previous version of the transcript, which differs in length by two amino acids.

| Nucleotide change | Amino acid change |
| --- | --- |
| 742 C > T | R248C |
| 746 C > G | S249C |
| 1114 G > T | G372C |
| 1117 A > T | S373C |
| 1124 A > G | Y375C |
| 1138 G > C | G380R (G382R) |
| 1138 G > A | G380E (G382E) |
| 1156 T > C | F384L (F386L) |
| 1172 C > A | A391E |
| 1948 A > G | K650E (K652E) |
| 1948 A > C | K650Q (K652Q) |
| 1949 A > T | K650M (K652M) |

The oligonucleotides, pharmaceutical compositions and methods described herein can be used to ameliorate or treat cancer, such as bladder cancer or skeletal dysplasias such as achondroplasia, for example, by reducing the expression or function of aberrant FGFR3 nucleic acid molecules.

Oligonucleotides

In some embodiments the oligonucleotides described herein target nucleic acids encoding aberrantly expressed FGFR3 (e.g., mRNA encoding FGFR3 as provided in SEQ ID NO: 4 and/or fragments thereof as provided in SEQ ID NO: 5 and SEQ ID NO: 6) and naturally occurring variants of such nucleic acids, and thereby modulate expression of FGFR3. As used herein, the term "oligonucleotide" refers to a molecule formed by the covalent linkage of two or more nucleotides. The term oligonucleotide generally includes oligonucleosides, oligonucleotide analogues, oligonucleotide mimetics and chimeric combinations of these. In the context of the present invention, a single nucleotide unit may also be referred to as a monomer or unit. In some embodiments, the terms "nucleoside", "nucleotide", "unit" and "monomer" are used interchangeably. It will be recognized that when referring to a sequence of nucleotides or monomers, what is referred to is the sequence of bases, such as, for example A, T (or U), G, or C.

In some embodiments, the oligonucleotides disclosed herein are useful for modulating the expression of nucleic acid molecules (e.g., modulating the expression of aberrantly expressed FGFR3) via an antisense mechanism of action. This modulation may be accomplished, for example, by providing oligonucleotides which are complementary to and/or hybridize to one or more target nucleic acid molecules, such as mRNA (e.g., SEQ ID NO: 4). In some embodiments, the oligonucleotides of the present invention are complementary to a specific region of a target nucleic acid (e.g., the region of FGFR3 mRNA encoding the G380R mutation). In some embodiments, the oligonucleotides of the present invention are capable of hybridizing to a specific region of a target nucleic acid (e.g., the region of FGFR3 mRNA encoding the G380R mutation).

As used herein, the phrase "target nucleic acid" is intended to encompass DNA and RNA (including pre-mRNA and mRNA or portions thereof) transcribed from such DNA, and also cDNA derived from such RNA. For example, in some embodiments, the phrase "target nucleic acid" is used to refer to nucleic acids encoding FGFR3 (e.g., mRNA), or in particular nucleic acids encoding mutated or aberrantly expressed FGFR3. As used herein, the term "gene product" refers to any biochemical materials resulting from expression of a gene or nucleic acid (e.g., DNA or RNA) and include, but are not limited to mRNA, RNA and/or proteins. For example, in some embodiments, when used with respect to the FGFR3 gene the phrase gene product refers to mRNA encoded by FGFR3. In certain embodiments, the target nucleic acid comprises a nucleic acid sequence selected from the group consisting of SEQ ID NO: 1, SEQ ID NO: 2, SEQ ID NO: 3, SEQ ID NO: 4, SEQ ID NO: 15, SEQ ID NO: 16, SEQ ID NO: 17, SEQ ID NO: 18, SEQ ID NO: 19 and SEQ ID NO: 20. In other embodiments, the oligonucleotides disclosed herein are complementary to and/or hybridize to a nucleic acid sequence comprising one or more of SEQ ID NO: 1, SEQ ID NO: 2, SEQ ID NO: 3, SEQ ID NO: 4, SEQ ID NO: 15, SEQ ID NO: 16, SEQ ID NO: 17, SEQ ID NO: 18, SEQ ID NO: 19 and/or SEQ ID NO: 20.

In some embodiments, the oligonucleotide compounds of the present invention are complementary to one or more target nucleic acids (e.g., mRNA encoding FGFR3) and interferes with the normal function of the targeted nucleic acid (e.g., by an antisense mechanism of action). This interference with or modulation of the function of a target nucleic acid by the oligonucleotides of the present invention which specifically hybridize to it is generally referred to as "antisense". The functions of DNA to be interfered with may include replication and transcription. The functions of RNA to be interfered with may include functions such as, for example, translocation of the RNA to the site of protein translation, translation of protein from the RNA, splicing of the RNA to yield one or more mRNA species, and catalytic activity which may be engaged in or facilitated by the RNA. In some embodiments, the overall effect of interference with a target nucleic acid function is modulation of the expression of the product of such target nucleic acid (e.g., FGFR3).

As the phrases are used herein, "antisense compound" or an "antisense oligonucleotide" refers to an oligonucleotide that is at least partially complementary (e.g., 100%, about 99%, 98%, 97.5%, 95%, 90%, 85%, 80%, 75%, 70%, 65%, 60%, 55%, or 50% complementary) to the region of a nucleic acid molecule, and in particular a target nucleic acid such as the mRNA encoding an aberrantly expressed protein or enzyme. In some embodiments, the antisense compound or antisense oligonucleotide is capable of hybridizing to a target nucleic acid, thereby modulating its expression. Consequently, while all antisense compounds can be said to be oligonucleotides, not all oligonucleotides are antisense compounds.

The oligonucleotides of the present invention consist of or comprise a contiguous nucleotide sequence of from about 8 to 50 nucleotides in length, such as for example 8 to 30 nucleotides in length. In various embodiments, the compounds of the invention do not comprise RNA units or monomers, but rather, for example, comprise DNA units or monomers and/or in some instances LNA units or monomers. It is preferred that the compound according to the invention is a linear molecule or is synthesized as a linear molecule. In some embodiments the oligonucleotide is a single stranded molecule, and preferably does not comprise short regions of, for example, at least 3, 4 or 5 contiguous nucleotides, which are complementary to equivalent regions within the same oligonucleotide (i.e., duplexes). In this regard, the oligonucleotide is not essentially double stranded.

The Target Sequences

In certain embodiments, the oligonucleotides described herein are capable of modulating, or in some embodiments down-regulating (e.g. reducing or eliminating) the expression of the FGFR3 (e.g., down-regulating aberrantly expressed FGFR3 at the mRNA level). In this regards, the oligonucleotides of the invention can affect the inhibition of FGFR3, typically in a mammalian cell such as a human cell (e.g., an A549 cell, a HeLa cell, a bladder cell or in a chondrocyte). In some embodiments, the oligonucleotides of the invention hybridize to the target nucleic acid (e.g., mutated or aberrantly expressed FGFR3 mRNA) and affect inhibition or reduction of expression of at least 10% or 20% compared to the normal expression level (e.g., such as the expression level in the absence of the oligonucleotide or conjugate). For example, the oligonucleotides disclosed herein may affect at least about a 30%, 40%, 50%, 60%, 70%, 80%, 90%, 95%, 97.5%, 98%, 99% or 100% reduction or inhibition of the expression of FGFR3 compared to the normal expression level of FGFR3 seen an individual carrying an FGFR3 mutant allele. In some embodiments, such modulation is evident upon exposing a targeted cell or tissue to a concentration of about 0.04 nM-25 nM (e.g., a concentration of about 0.8 nM-20 nM) of the compound of the invention. In the same or a different embodiment, the inhibition of expression of the target nucleic acid (e.g., mRNA encoding mutated FGFR3) is less than 100% (e.g., such as less than about 98% inhibition, less than about 95% inhibition, less than about 90% inhibition, less than about 80% inhibition or less than about 70% inhibition). In some embodiments, the oligonucleotides disclosed herein are capable of modulating expression of FGFR3 at the mRNA level (e.g., by targeting and hybridizing to mRNA encoding mutated or aberrantly expressed FGFR3). Modulation of expression (e.g., at the mRNA level) can be determined by measuring protein levels or concentrations (e.g., by SDS-PAGE followed by Western blotting using suitable antibodies raised against the target protein). Alternatively, modulation of expression (e.g., at the mRNA level) can be determined by measuring levels or concentrations of mRNA, (e.g., by Northern blotting or quantitative RT-PCR). When measuring expression via the evaluation of mRNA levels or concentrations, the degree of down-regulation when using an appropriate dosage or concentration of an oligonucleotide (e.g., about 0.04 nM-25 nM, or about 0.8 nM-20 nM), can be greater than about 10%, from about 10-20%, greater than about 20%, greater than about 25%, or greater than about 30% relative to the normal levels or concentrations observed in the absence of the oligonucleotide, conjugate or composition of the invention.

In the context of the present invention, the terms "modulating" or "modulation" can mean one or more of an increase (e.g., stimulation or upregulation) in the expression of a gene or gene product (e.g., FGFR3 mRNA), a decrease (e.g., downregulation or inhibition) in the expression of a gene or gene product (e.g., FGFR3 mRNA), and a change in the relative expression between two or more gene products (e.g., a reduction in the expression of mutant FGFR3 relative to the expression of wild-type FGFR3). In some contexts described herein, downregulation and inhibition are the preferred forms of modulation, in particular as it relates to modulating the expression of mutated FGFR3. In some contexts described herein, the term "expression" means the process by which information from a gene or nucleic acid (e.g., DNA) is used in the synthesis of gene products (e.g., mRNA, RNA and/or proteins) and includes, but is not limited to, one or more of the steps of replication, transcription and translation. The steps of expression which may be modulated by the oligonucleotides of the present invention may include, for example, transcription, splicing, translation and post-translational modification of a protein.

As it relates to targeting, modulation and expression, the term "FGFR3" broadly can refer to the fibroblast growth factor receptor type 3 gene or its gene product (e.g., pre-mRNA, mature mRNA, cDNA, or protein) and can include both mutated and wild-type forms, iso forms and variants thereof (e.g., the nucleic acids encoding human FGFR3 and coding for FGFR3 protein). The italicized term, "FGFR3" as used herein typically refers to the FGFR3 gene. The term "wild-type" as it describes FGFR3, refers to the most frequently observed FGFR3 allele, nucleotide sequence, amino acid sequence, or phenotype in a subject or population. For example, relative to a G380R mutated FGFR3 allele in a patient with heterozygous achondroplasia, the term "wild-type" refers to the remaining allele that does not comprise a G380R mutation. The term "mutated" as it describes FGFR3 refers to an altered allele, nucleotide sequence, amino acid sequence, or phenotype in a subject or population, for example, transition and transversion point mutations that result in the replacement of a single base nucleotide with another nucleotide of the genetic material (e.g., DNA or RNA). An example of a mutation is the G to A transition substitution at position 1138 of the coding region of human FGFR3 (corresponding to position 1394 of human FGFR3 (NM_000142), and inclusive of any variants and polymorphs thereof which comprise the same G to A transition substitution), which results in the codon position 380 being changed from GGG (coding for arginine or R) to AGG or CGG (coding for glycine or G), thus the use of the reference "G380R" to describe the mutation. The SNP ID for this mutation is SNP rs28931614.

As it specifically relates to FGFR3, the phrase "modulating the expression" means a stimulation, upregulation, downregulation, and/or inhibition of the gene products of the FGFR3 gene (e.g., the gene products of the wild-type and/or mutated FGFR3). For example, the oligonucleotides of the present invention that target the nucleic acids (e.g., mRNA) encoding aberrantly expressed FGFR3 and specifically hybridize to such nucleic acids (e.g., mRNA encoding FGFR3) can modulate the expression FGFR3. The oligonucleotides described herein can modulate the expression of both wild-type and mutated FGFR3 in patients with heterozygous achondroplasia. Alternatively, in preferred embodiments, the oligonucleotides described herein can preferentially downregulate or inhibit the expression of mutant FGFR3 (e.g., the oligonucleotides described herein may modulate the expression of the G380R mutant FGFR3 in patients with heterozygous achondroplasia caused by the FGFR3 G380R mutation).

In some embodiments, the oligonucleotides of the present invention are capable of targeting specific nucleic acids. Targeting in the context of the antisense oligonucleotides described herein to a particular nucleic acid can be a multi-step process. The process usually begins with the identification of a nucleic acid sequence whose function is to be modulated. This may be, for example, a nucleic acid (e.g., mRNA) whose expression is associated with a particular disorder or disease state (e.g., achondroplasia). In some embodiments, the target nucleic acid (e.g., mRNA) encodes FGFR3. For example, the target nucleic acid may comprise a region or fragment of the nucleic acid gene encoding the G380R FGFR3 mutation, and the oligonucleotide targeting such region complement to and/or hybridize to the nucleic acids encoding FGFR3 mRNA. Alternatively, in some embodiments the target nucleic acid encodes a particular region of the FGFR3 gene (or the corresponding mRNA gene product thereof) which encodes the G380R mutation. The targeting process also can include a determination of a site or sites within the target gene for the antisense interaction to occur such that one or more desired effects will result. The one or more desired effects can include, for example, modulation of expression of a gene product (e.g., wild-type and/or mutant mRNA or protein), selective binding (e.g., increased binding affinity) for the target site relative to other sites on the same gene or mRNA or on other genes or mRNAs, sufficient or enhanced delivery to the target, and minimal or no unwanted side effects. In some embodiments, a preferred targeted nucleic acid or mRNA site encodes the FGFR3 G380R mutation and/or the region surrounding or adjacent to such G380R mutation. In particular, a preferred site comprises the guanine to adenine nucleotide mutation at position 1138 of codon 380 of FGFR3.

The G380R mutation represents the most common mutation responsible for the development of achondroplasia. As described above, the term "G380R" refers to a point mutation that results in the replacement of arginine (R) for glycine (G) at codon 380 of the FGFR3 protein. In some contexts of the present inventions, the phrase "G380R region" can include codons that are upstream and/or downstream from the G380R mutation, for example, the region measuring about 2, 5, 10, 12, 20, 30, 50, 60, 75, 80, 100 or more codons upstream and/or downstream from the G380R mutation. The G380R mutation (GGG at codon position 380 changed to AGG or CGG) occurs within the transmembrane domain of the G380R receptor protein and results in hyperactivation of the receptor. Prolonged activation of FGFR3 results in premature cessation of chondrocyte proliferation, and premature chondrocyte differentiation. The G380R-mutated forms of FGFR3 have a disease-causing gain-of-function, and accordingly the antisense oligonucleotides described herein can selectively downregulate the expression of mutated FGFR3 in order to restore normal chondrocyte function by allowing the remaining wild-type allele to guide proper expansion of the growth plates in the long bones. Specifically, in patients with heterozygous achondroplasia, the oligonucleotides described herein target and hybridize to nucleic acids (i.e., mRNA) encoding G380R-mutated FGFR3 (e.g., a nucleic acid encoded by the sequence comprising SEQ ID NO: 4) on a discriminatory or selective basis, such that expression of mutated FGFR3 allele is downregulated or inhibited, while the same compound does not target or hybridize to the wild-type FGFR3 (e.g., SEQ ID NO: 1) or does so to a lesser extent, thus preserving the function of the remaining wild-type allele, thereby restoring normal chondrocyte function and guiding proper expansion of the growth plates in the long bones.

The oligonucleotides described herein may be delivered to one or more of an animal, a mammal, a human, or a cell. Targeted cell types may, in some embodiments, include chondrocyte cells, HeLa cells or A549 cells. In certain embodiments, the oligonucleotide concentration used (e.g., in A549 cells) may be about 0.25 nM, 0.5 nM, 1 nM, 5 nM, 40 nM, 100 nM, 200 nM, 250 nM or more. The oligonucleotide concentration used may, in some embodiments be 25 nM (e.g., in chondrocyte cells). The oligonucleotide concentration used may, in some embodiments be 1 nM (e.g., in chondrocyte cells). In the absence of a transfection reagent (e.g., using gymnotic delivery) an oligonucleotide concentration between about 1 µM-25 µM (e.g., such as about 5 µM) may be used to downregulate the target gene.

In certain embodiments, the oligonucleotides disclosed herein may be periodically administered to a subject (e.g., administered intravenously or subcutaneously to a human on a daily, weekly, monthly, quarterly, semi-annually or annual basis) at a dose of about 0.2 to about 20 mg/kg (e.g., administered in daily or weekly doses of at least about 0.2 mg/kg, 0.25 mg/kg, 0.5 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg, 5.0 mg/kg, 6.0 mg/kg, 7.5 mg/kg, 8.0 mg/kg, 10 mg/kg, 12.5 mg/kg, 15 mg/kg or 20 mg/kg). It should be noted that in some embodiments the determination of the appropriate concentration of oligonucleotide used to treat the cell may be performed in an in vitro cell assay using a transfection reagent (e.g., LIPOFECTIN).

In some embodiments, the oligonucleotides described herein are potent inhibitors of FGFR3 (i.e., are capable of modulating the expression of FGFR3 in a cell or tissue upon exposing such cell or tissue to a relatively low concentration of the oligonucleotide). In some embodiments, the oligonucleotides are capable of reducing or otherwise inhibiting the expression of FGFR3 (e.g., of mutated FGFR3) at relatively low concentrations of such oligonucleotide. For example, in some embodiments an oligonucleotide may inhibit expression of FGFR3 by a cell at a relatively low concentration (e.g., an $IC_{50}$ of less than about 5 nM as determined by a transfection assay, or an $IC_{50}$ of less than about 4 nM, such as less than 2 nM). As used herein, the term "$IC_{50}$" refers to the concentration of an oligonucleotide that is sufficient to inhibit an objective parameter (e.g., FGFR3 protein expression) by about fifty percent. In certain embodiments, the antisense oligonucleotides disclosed herein are characterized as selectively inhibiting the expression of mutant FGFR3 protein relative to the expression of wild-type FGFR3 protein. Accordingly, an oligonucleotide may be characterized as inhibiting the expression of mutant FGFR3 protein at a lower concentration (e.g., about two-fold lower) relative to the concentration required to inhibit expression of a wild-type FGFR3 protein. For example, the antisense oligonucleotides may demonstrate at least a two-fold difference in the $IC_{50}$ for the mutant and wild-type FGFR3 proteins (e.g., at least about a 2.5-, 3-, 4-, 5-, 6-, 7-, 8-, 9- or 10-fold difference in the $IC_{50}$ required to inhibit expression of the FGFR3 mutant protein relative to the normal or wild-type protein in a mammal with heterozygous achondroplasia).

The invention therefore provides methods of modulating (e.g., downregulating or inhibiting) the expression of an aberrantly expressed FGFR3 protein and/or FGFR3 mRNA, and in particular FGFR3 mRNA encoded by a G380R-mutated FGFR3 gene, in a cell aberrantly expressing such FGFR3 protein and/or mRNA (e.g., a chondrocyte expressing the G380R mutant FGFR3 protein and/or mRNA). Such methods comprise administering the oligonucleotide or conjugate according to the invention to a cell (or otherwise contacting such cell with such oligonucleotide or conjugate) to downregulate or inhibit the expression of FGFR3 protein and/or mRNA in said cell. In some embodiments, the cell can be an in vitro or in vivo mammalian cell, such as a human cell. For example, an oligonucleotide of the present invention that targets a mutated FGFR3 gene and is capable of specifically hybridize to the gene product thereof (e.g., mutated FGFR3 mRNA) may modulate the expression of mutated FGFR3. The oligonucleotides of the present invention may modulate the expression of wild-type and/or mutated FGFR3 alleles in patients with heterozygous achondroplasia. The administration to the patient (e.g., human or mammalian), subject (e.g., human or mammalian), and/or cell (e.g., human or mammalian) may occur in vivo, ex vivo, or in vitro. For example, in some embodiments, the oligonucleotide in a pharmaceutically acceptable formulation and/or in a pharmaceutically acceptable carrier or delivery vehicle may be administered directly into the patient's or subject's body, by methods described herein. Alternatively, in some embodiments, the oligonucleotide may be administered to cells after they are removed and before they are returned to the patient's or subject's body. In some embodiments, the cells may be maintained under culture conditions after they are removed and before they are returned to the patient's or subject's body.

The phrase "target nucleic acid", as used herein refers to the nucleic acids (e.g., mRNA) encoding mammalian FGFR3, and in particular refers to the nucleic acids (e.g., mRNA) encoding mutated or aberrantly expressed FGFR3. For example, disclosed herein are target nucleic acids which encoding G380R-mutated FGFR3 (e.g., mRNA encoding G380R-mutated FGFR3, such as is encoded by SEQ ID NO: 4). Suitable target nucleic acids include nucleic acids encoding FGFR3 or naturally occurring variants thereof, and RNA nucleic acids derived therefrom (e.g., mRNA target sequences comprising or corresponding to SEQ ID NOS: 15-20), preferably mRNA, such as pre-mRNA, although preferably mature mRNA. In some embodiments (e.g., when used in a research or diagnostic context) the "target nucleic acid" may be a cDNA or a synthetic oligonucleotide derived from the above DNA or RNA nucleic acid targets. The oligonucleotides according to the invention are capable of hybridizing to the target nucleic acid or to the gene product of such target nucleic acid. It will be recognized that in some embodiments the target nucleic acid sequence is a cDNA sequences and as such, corresponds to the mature mRNA target sequence, although uracil may be replaced with thymidine in the cDNA sequences.

The term "naturally occurring variant thereof" refers to variants of the FGFR3 polypeptide or nucleic acid sequence which exist naturally within the defined taxonomic group, such as mammalian, such as mouse, monkey, and preferably human. Typically, when referring to "naturally occurring variants" of a polynucleotide the term also may encompass any allelic variant of the FGFR3 encoding genomic DNA that is found at the chromosome 4p16.3 by chromosomal translocation or duplication, and the RNA, such as mRNA derived therefrom. For example, naturally occurring variants of FGFR3 may include the G380R mutant, as is encoded for example by SEQ ID NO: 4, or the naturally occurring variants thereof (e.g., SNP ID's rs28931614, rs11943863 or rs17881656). Naturally occurring variants may also include variants derived from alternative splicing of the FGFR3 mRNA. When referenced to a specific polypeptide sequence the term also includes naturally occurring forms of the protein which may therefore be processed, for example, by co- or post-translational modifications (e.g., signal peptide cleavage, proteolytic cleavage, glycosylation, etc.)

Sequences

In some embodiments the oligonucleotides comprise or consist of a contiguous nucleotide sequence which corresponds to the reverse complement of a nucleotide sequence of SEQ ID NO: 1 or SEQ ID NO: 4, or a fragment of SEQ ID NO: 1 or SEQ ID NO: 4. Thus, the oligonucleotide can comprise or consist of a sequence selected from the group consisting of SEQ ID NOS: 9, 10, 11, 12, 13 or 14, wherein said oligonucleotide (or contiguous nucleotide portion thereof) may optionally have one, two, or three mismatches against the selected target sequence. In some embodiments, the oligonucleotides may comprise or consist of a contiguous nucleotide sequence which corresponds to the reverse complement of a nucleotide sequence encoding the FGFR3 sequence region that includes the G380R mutation and nucleotides surrounding such mutation. For example, in some embodiments the oligonucleotides may comprise the sequences identified in Table 1 (i.e., SEQ ID NO: 9, SEQ ID NO: 10, SEQ ID NO: 11, SEQ ID NO: 12, SEQ ID NO: 13 or SEQ ID NO: 14). The oligonucleotides may be complementary to a region of a nucleic acid (e.g., mRNA) encoding FGFR3 that includes the G380R mutation (e.g., a region which is about 1, 2, 3, 4, 5, 6, 7, 8, 9, 10, 11, 12, 13, 14, 15, 16, 17, 18, 19, 20 or more nucleotides upstream and/or downstream from the G380R mutation), such as the target sequences identified in Table 1. For example, in some embodiments the oligonucleotides may be complementary to the mRNA target sequences identified in Table 1 (e.g., SEQ ID NO: 15, SEQ ID NO: 16, SEQ ID NO: 17, SEQ ID NO: 18, SEQ ID NO: 19 or SEQ ID NO: 20). In some embodiments, such complementary oligonucleotides are capable of hybridizing to the gene product of FGFR3 (i.e., FGFR3 mRNA), and in particular the gene product of FGFR3 encoding the G380R mutation.

TABLE 1

| Oligo-nucleotide SEQ ID NO | Oligo-nucleotide Sequence | mRNA Target Sequence Identifier | mRNA Target Sequence |
|---|---|---|---|
| SEQ ID NO: 9 | 5'-CTGTAGCTGA GGATGC-3' | SEQ ID NO: 15 | 5'-GCAUCCUCAGC UACAG-3' |
| SEQ ID NO: 10 | 5'-GAAGCCCACC CTGTA-3' | SEQ ID NO: 16 | 5'-UACAGGGUGGG CUUC-3' |
| SEQ ID NO: 11 | 5'-GAAGAAGCCC ACCCTG-3' | SEQ ID NO: 17 | 5'-CAGGGUGGGCU UCUUC-3' |
| SEQ ID NO: 12 | 5'-AAGAAGCCCA CCCT-3' | SEQ ID NO: 18 | 5'-AGGGUGGGCUU CUU-3' |
| SEQ ID NO: 13 | 5'-GAAGAAGCCC ACCCT-3' | SEQ ID NO: 19 | 5'-AGGGUGGGCUU CUUC-3' |
| SEQ ID NO: 14 | 5'-GAAGCCCACC CT-3' | SEQ ID NO: 20 | 5'-AGGGUGGGCUU C-3' |

The oligonucleotide may comprise or consist of a contiguous nucleotide sequence which is fully complementary (perfectly complementary) to the equivalent region of a nucleic acid which encodes a mammalian FGFR3 (e.g., SEQ ID NO: 1, SEQ ID NO: 4 or a fragment thereof). Thus, the oligonucleotide can comprise or consist of an antisense nucleotide sequence capable of hybridizing to the nucleic acids encoding FGFR3 (i.e., FGFR3 mRNA).

However, in some embodiments, the oligonucleotide may tolerate 1, 2, 3 or 4 (or more) mismatches, when hybridizing to the target sequence and still sufficiently bind to the target to show the desired effect (e.g., downregulation of the target mRNA). Mismatches may, for example, be compensated by increased length of the oligonucleotide sequence and/or an increased number of nucleotide analogues, such as locked nucleic acids (LNA), present within the nucleotide sequence. In some embodiments, the contiguous nucleotide sequence comprises no more than 3 mismatches (e.g., no more than 1 or no more than 2 mismatches) when hybridizing to a target sequence, such as to the corresponding region of a nucleic acid which encodes a mammalian FGFR3 mRNA. In some embodiments, the contiguous nucleotide sequence comprises no more than a single mismatch when hybridizing to the target sequence, such as the corresponding region of a nucleic acid which encodes a mammalian FGFR3 mRNA.

The nucleotide sequence of the oligonucleotides of the invention or the contiguous nucleotide sequence is preferably at least 80% complementary to a sequence selected from the group consisting of SEQ ID NOS: 15, 16, 17, 18, 19 or 20, such as at least 85%, at least 90%, at least 91%, at least 92%, at least 93%, at least 94%, at least 95%, at least 96%, at least 97%, at least 98%, at least 99%, such as at least 100% complementary.

The nucleotide sequence of the oligonucleotides of the invention or the contiguous nucleotide sequence is preferably at least 80% homologous to the reverse complement of a corresponding sequence present in SEQ ID NO: 4, such as at least 85%, at least 90%, at least 91%, at least 92%, at least 93%, at least 94%, at least 95%, at least 96% homologous, at least 97% homologous, at least 98% homologous, at least 99% homologous, such as 100% homologous (identical).

The nucleotide sequence of the oligonucleotides of the invention or the contiguous nucleotide sequence is preferably at least 80% complementary to a sub-sequence present in SEQ ID NO: 4, such as at least 85%, at least 90%, at least 91%, at least 92%, at least 93%, at least 94%, at least 95%, at least 96% complementary, at least 97% complementary, at least 98% complementary, at least 99% complementary, such as 100% complementary (perfectly complementary).

In some embodiments the oligonucleotide (or contiguous nucleotide portion thereof) is selected from, or comprises, one of the sequences selected from the group consisting of SEQ ID NOS: 9, 10, 11, 12, 13 or 14, or a sub-sequence of at least about 6-10 contiguous nucleotides thereof. In some embodiments, said oligonucleotide (or contiguous nucleotide portion thereof) may optionally comprise one, two, or three mismatches when compared to the sequence.

In some embodiments the sub-sequence may consist of 8, 9, 10, 11, 12, 13, 14, 15, 16, 17, 18, 19, 20, 21, 22, 23, 24, 25, 26, 27, 28, or 29 contiguous nucleotides, such as from about 12-22, such as from about 12-18 nucleotides. Suitably, in some embodiments, the sub-sequence is of the same length as the contiguous nucleotide sequence of the oligonucleotide of the invention.

However, it is recognized that, in some embodiments the nucleotide sequence of the oligonucleotide may comprise additional 5' or 3' nucleotides or modifications, such as, independently 1, 2, 3, 4 or 5 additional nucleotides 5' and/or 3', which are non-complementary to the target sequence. In this respect, the oligonucleotides of the invention may, in some embodiments, comprise a contiguous nucleotide sequence flanked 5' and or 3' by additional nucleotides. In some embodiments the additional 5' or 3' nucleotides are naturally occurring nucleotides, such as DNA or RNA. In some embodiments, the additional 5' or 3' nucleotides may represent region W as referred to in the context of the gapmer oligonucleotides disclosed herein.

In some embodiments the oligonucleotide according to the invention consists or comprises of a nucleotide sequence according to SEQ ID NOS: 9, 10, 11, 12, 13 or 14, or a sub-sequence of thereof.

In some embodiments the oligonucleotide according to the invention consists of or comprises a nucleotide sequence according to SEQ ID NO: 9 or a sub-sequence of thereof.

In some embodiments the oligonucleotide according to the invention consists of or comprises a nucleotide sequence according to SEQ ID NO: 10 or a sub-sequence of thereof.

In some embodiments the oligonucleotide according to the invention consists of or comprises a nucleotide sequence according to SEQ ID NO: 11 or a sub-sequence of thereof.

In some embodiments the oligonucleotide according to the invention consists of or comprises a nucleotide sequence according to SEQ ID NO: 12 or a sub-sequence of thereof.

In some embodiments the oligonucleotide according to the invention consists of or comprises a nucleotide sequence according to SEQ ID NO: 13 or a sub-sequence of thereof.

In some embodiments the oligonucleotide according to the invention consists of or comprises a nucleotide sequence according to SEQ ID NO: 14 or a sub-sequence of thereof.

In determining the degree of complementarity between the oligonucleotides of the invention (or regions thereof) and the target region of a nucleic acid (e.g., mRNA encoding mammalian FGFR3 protein) the degree of complementarity (or homology or identity) is expressed as the percentage identity (or percentage homology) between the sequence of the oligonucleotide (or region thereof) and the sequence of the target region (or the reverse complement of the target region) that best aligns therewith. The percentage is calculated by counting the number of aligned bases that are identical between the 2 sequences, dividing by the total number of contiguous monomers in the oligonucleotide, and multiplying by 100. In such a comparison, if gaps exist, it is preferable that such gaps are merely mismatches rather than areas where the number of monomers within the gap differs between the oligonucleotide of the invention and the target region. As used herein, the terms "homologous" and "homology" are interchangeable with the terms "identity" and "identical".

The phrases "corresponding to" and "corresponds to" refer to the comparison between the nucleotide sequence of the oligonucleotide (i.e., the nucleobase or base sequence) or contiguous nucleotide sequence and the equivalent contiguous nucleotide sequence of a further sequence selected from either, (i) a sub-sequence of the reverse complement of the nucleic acid target, such as the mRNA which encodes the FGFR3 protein, and/or (ii) the sequence of nucleotides provided herein such as the group consisting of SEQ ID NOS: 15, 16, 17, 18, 19 or 20, or sub-sequence thereof. Nucleotide analogues are compared directly to their equivalent or corresponding nucleotides. A first sequence which corresponds to a further sequence under (i) or (ii) typically is identical to that sequence over the length of the first sequence (such as the contiguous nucleotide sequence) or, as described herein may, in some embodiments, be at least 80% homologous to a corresponding sequence, such as at least 85%, at least 90%, at least 91%, at least 92% at least 93%, at least 94%, at least 95%, at least 96% homologous, such as 100% homologous (identical).

Once one or more target sites have been identified, oligonucleotides are chosen which are sufficiently complementary to the target (i.e., hybridize sufficiently well and with sufficient specificity, to give the desired effect). For example, upon identifying a region of FGFR3 mRNA to target, oligonucleotides may be chosen based upon complementarity to the mRNA target or alternatively to the DNA encoding such mRNA target. In this context, "hybridization" means hydrogen bonding, which may be Watson-Crick, Hoogsteen or reversed Hoogsteen hydrogen bonding, between complementary nucleoside or nucleotide bases. For example, adenine (A) and thymine (T) are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. The sequence of an antisense compound may be, for example, about 40%, 50%, 60%, 65%, 70%, 75%, 80%, 85%, 90%, 95%, 97%, 97.5%, 99% or 100% complementary to that of its target sequence to be specifically hybridizable. An antisense compound is specifically hybridizable when binding of the compound to the target DNA or RNA molecule interferes with the normal function of the target DNA or RNA to cause a loss of function or utility, and there is a sufficient degree of complementarity to avoid non-specific binding of the antisense compound to non-target sequences under conditions in which specific binding is desired, (e.g., under physiological conditions in the case of in vivo assays or therapeutic treatment, and in the case of in vitro assays, under conditions in which the assays are performed). The phrases "reverse complement", "reverse complementary" and "reverse complementarity" as used herein are interchangeable with the terms "complement", "complementary" and "complementarity".

Antisense and other oligonucleotides of the invention which hybridize to the target nucleic acids (e.g., mRNA encoding a mutated FGFR3 protein) and inhibit expression of the target nucleic acid are identified through experimentation, and the sequences of these compounds are herein identified as preferred embodiments of the invention (e.g., the sequences identified in Table 1). The target nucleic acids or sites to which these preferred sequences are complementary are herein referred to as "active sites" and are therefore preferred sites for targeting (e.g., target sequences identified in Table 1). An example of an active site contemplated by the present invention includes the regions surround a glycine to arginine mutation at codon 380 of FGFR3, such as for example, the G380R region. Therefore another embodiment of the invention encompasses compounds which hybridize to this active site region, which can include nucleotides immediately upstream and/or downstream from the active site. For example, the region measuring about 1, 2, 5, 10, 12, 20, 30, 50, 60, 75, 80, 100 or more codons upstream and/or downstream from the G380R mutation.

The phrases "corresponding nucleotide analogue" and "corresponding nucleotide" are intended to indicate that the nucleotide in the nucleotide analogue and the naturally occurring nucleotide are identical. For example, when the 2-deoxyribose unit of the nucleotide is linked to an adenine, the corresponding nucleotide analogue contains a pentose unit (different from 2-deoxyribose) linked to an adenine.

Length

The oligonucleotides may comprise or consist of a contiguous nucleotide sequence of a total of 5, 6, 7, 8, 9, 10, 11, 12, 13, 14, 15, 16, 17, 18, 19, 20, 21, 22, 23, 24, 25, 26, 27, 28, 29 or 30 contiguous nucleotides in length. In some embodiments, the oligonucleotides comprise or consist of a contiguous nucleotide sequence of a total of from about 8-25, such as about 10-22, such as about 12-18, such as about 13-17 or 12-16, such as about 13, 14, 15, 16 contiguous nucleotides in length. In some embodiments, the oligonucleotides comprise or consist of a contiguous nucleotide sequence of a total of 8, 9, 10, 11, 12, 13, or 14 contiguous nucleotides in length. In some embodiments, the oligonucleotide according to the invention consists of no more than 22 nucleotides, such as no more than 20 nucleotides, such as no more than 18 nucleotides, such as 15, 16 or 17 nucleotides. In some embodiments the oligonucleotide of the invention comprises less than 20 nucleotides. It should be understood that when a range is given for an oligonucleotide, or contiguous nucleotide sequence length it includes the lower an upper lengths provided in the range, for example from (or between) 10-30, includes both 10 and 30.

Nucleosides and Nucleoside Analogues

Nucleotide Analogues

The term "nucleotide" as used herein, refers to a glycoside comprising a sugar moiety, a base moiety and a covalently linked group, such as a phosphate or phosphorothioate internucleotide linkage group, and covers both naturally occurring nucleotides, such as DNA or RNA, and non-naturally occurring nucleotides comprising modified sugar and/or base moieties, which are also referred to as "nucleotide analogues" herein. Herein, a single nucleotide (unit) may also be referred to as a monomer or nucleic acid unit.

In field of biochemistry, the term "nucleoside" is commonly used to refer to a glycoside comprising a sugar moiety and a base moiety, and may therefore be used when referring to the nucleotide units, which are covalently linked by the internucleotide linkages between the nucleotides of the oligomer.

As one of ordinary skill in the art would recognise, the 5' nucleotide of an oligonucleotide does not comprise a 5' internucleotide linkage group, although may or may not comprise a 5' terminal group.

Non-naturally occurring nucleotides include nucleotides which have modified sugar moieties, such as bicyclic nucleotides or 2' modified nucleotides, such as 2' substituted nucleotides.

"Nucleotide analogues" are variants of natural nucleotides, such as DNA or RNA nucleotides, by virtue of modifications in the sugar and/or base moieties. Analogues could in principle be merely "silent" or "equivalent" to the natural nucleotides in the context of the oligonucleotide, i.e. have no functional effect on the way the oligonucleotide works to inhibit target gene expression. Such "equivalent" analogues may nevertheless be useful if, for example, they are easier or cheaper to manufacture, or are more stable to storage or manufacturing conditions, or represent a tag or label. Preferably, however, the analogues will have a functional effect on the way in which the oligomer works to inhibit expression; for example by producing increased binding affinity to the target and/or increased resistance to intracellular nucleases and/or increased ease of transport into the cell. Specific examples of nucleoside analogues are described by e.g. Freier & Altmann; *Nucl. Acid Res.*, 1997, 25, 4429-4443 and Uhlmann; *Curr. Opinion in Drug Development*, 2000, 3(2), 293-213, and below:

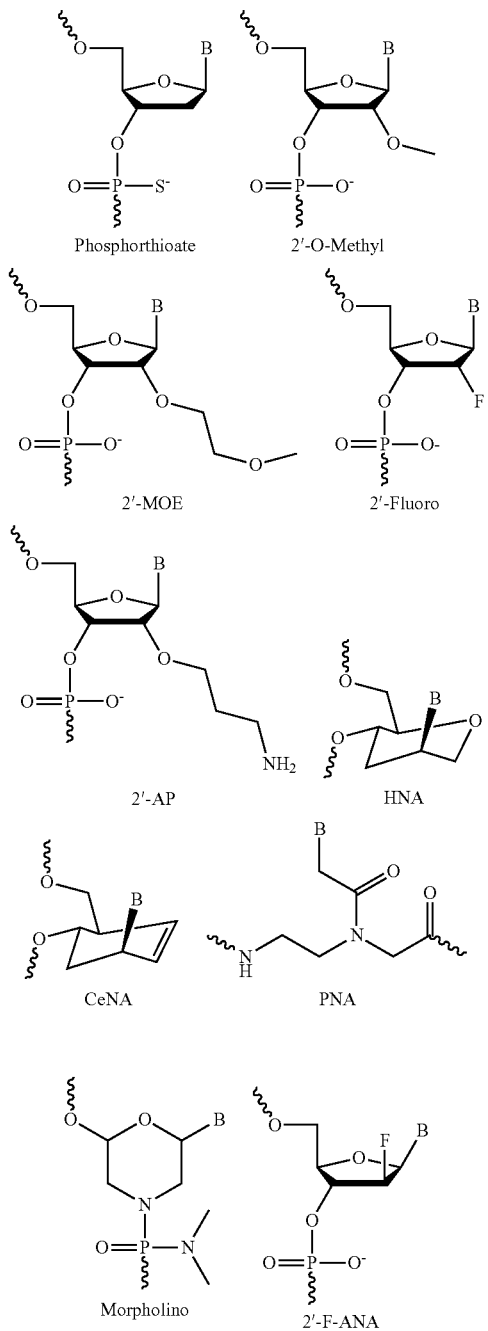

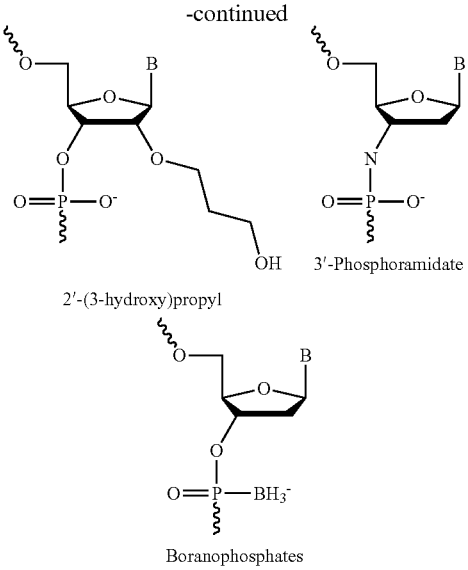

The oligomer may thus comprise or consist of a simple sequence of natural occurring nucleotides—preferably 2'-deoxynucleotides (referred here generally as "DNA"), but also possibly ribonucleotides (referred here generally as "RNA"), or a combination of such naturally occurring nucleotides and one or more non-naturally occurring nucleotides, i.e. nucleotide analogues. Such nucleotide analogues may suitably enhance the affinity of the oligomer for the target sequence.

Examples of suitable and preferred nucleotide analogues are provided by PCT/DK2006/000512 or are referenced therein.

Incorporation of affinity-enhancing nucleotide analogues in the oligomer, such as LNA or 2'-substituted sugars, can allow the size of the specifically binding oligomer to be reduced, and may also reduce the upper limit to the size of the oligomer before non-specific or aberrant binding takes place.

In some embodiments the oligomer comprises at least 2 nucleotide analogues. In some embodiments, the oligomer comprises from 3-8 nucleotide analogues, e.g. 6 or 7 nucleotide analogues. In the by far most preferred embodiments, at least one of said nucleotide analogues is a locked nucleic acid (LNA); for example at least 3 or at least 4, or at least 5, or at least 6, or at least 7, or 8, of the nucleotide analogues may be LNA. In some embodiments all the nucleotides analogues may be LNA.

It will be recognised that when referring to a preferred nucleotide sequence motif or nucleotide sequence, which consists of only nucleotides, the oligomers of the invention which are defined by that sequence may comprise a corresponding nucleotide analogue in place of one or more of the nucleotides present in said sequence, such as LNA units or other nucleotide analogues, which raise the duplex stability/$T_m$ of the oligomer/target duplex (i.e. affinity enhancing nucleotide analogues).

LNA

The term "LNA" refers to a bicyclic nucleoside analogue which comprises a C2*-C4* biradical (a bridge), and is known as "Locked Nucleic Acid" or "BNA" ("Bicyclic Nucleic Acid" or "Bridged Nucleic Acid"). It may refer to an LNA monomer, or, when used in the context of an "LNA oligonucleotide", LNA refers to an oligonucleotide containing one or more such bicyclic nucleotide analogues. In some aspects bicyclic nucleoside analogues are LNA nucleotides, and these terms may therefore be used interchangeably, and in such embodiments, both are characterized by the presence of a linker group (such as a bridge) between C2' and C4' of the ribose sugar ring.

In some embodiments the LNA used in the oligonucleotide compounds of the invention preferably has the structure of the general Formula A:

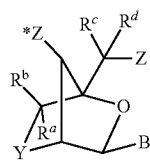

Formula A wherein Y is selected from the group consisting of —O—, —CH$_2$O—, —S—, —NH—, N(R$^e$) and/or —CH$_2$—; Z and Z* are independently selected among an internucleotide linkage, R$^H$, a terminal group or a protecting group; B constitutes a natural or non-natural nucleotide base moiety (nucleobase), and R$^H$ is selected from hydrogen and C$_{1-4}$-alkyl; R$^a$, R$^b$ R$^c$, R$^d$ and R$^e$ are, optionally independently, selected from the group consisting of hydrogen, optionally substituted C$_{1-12}$-alkyl, optionally substituted C$_{2-12}$-alkenyl, optionally substituted C$_{2-12}$-alkynyl, hydroxy, C$_{1-12}$-alkoxy, C$_{2-12}$-alkoxyalkyl, C$_{2-12}$-alkenyloxy, carboxy, C$_{1-12}$-alkoxycarbonyl, C$_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, DNA intercalators, photochemically active groups, thermochemically active groups, chelating groups, reporter groups, and ligands, where aryl and heteroaryl may be optionally substituted and where two geminal substituents R$^a$ and R$^b$ together may designate optionally substituted methylene (=CH$_2$); and R$^H$ is selected from hydrogen and C$_{1-4}$-alkyl. In some embodiments R$^a$, R$^b$ R$^c$, R$^d$ and R$^e$ are, optionally independently, selected from the group consisting of hydrogen and C$_{1-6}$ alkyl, such as methyl. For all chiral centers, asymmetric groups may be found in either R or S orientation, for example, two exemplary stereochemical isomers include the beta-D and alpha-L isoforms, which may be illustrated as follows:

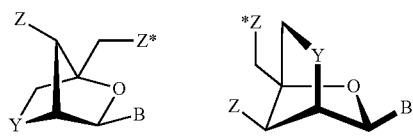

Specific exemplary LNA units are shown below:

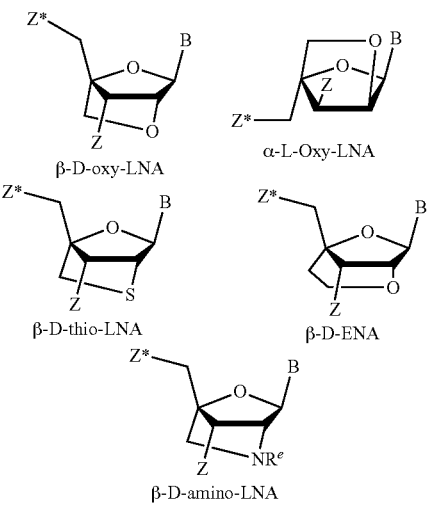

The term "thio-LNA" comprises a locked nucleotide in which Y in the general formula above is selected from S or —CH$_2$—S—. Thio-LNA can be in both beta-D and alpha-L-configuration.

The term "amino-LNA" comprises a locked nucleotide in which Y in the general formula above is selected from —N(H)—, N(R)—, CH$_2$—N(H)—, and —CH$_2$—N(R)— where R is selected from hydrogen and C$_{1-4}$-alkyl. Amino-LNA can be in both beta-D and alpha-L-configuration.

The term "oxy-LNA" comprises a locked nucleotide in which Y in the general formula above represents —O—. Oxy-LNA can be in both beta-D and alpha-L-configuration.

The term "ENA" comprises a locked nucleotide in which Y in the general formula above is —CH$_2$—O— (where the oxygen atom of —CH$_2$—O— is attached to the 2'-position relative to the base B). R$^e$ is hydrogen or methyl.

In some exemplary embodiments LNA is selected from beta-D-X-LNA or alpha-L-X-LNA (wherein X is oxy, amino or thio), or other LNAs disclosed herein including, but not limited to, (R/S) cET, cMOE or 5'-Me-LNA, in particular beta-D-oxy-LNA.

As used herein, "bicyclic nucleosides" refer to modified nucleosides comprising a bicyclic sugar moiety. Examples of bicyclic nucleosides include, without limitation, nucleosides comprising a bridge between the 4' and the 2' ribosyl ring atoms. In some embodiments, compounds provided herein include one or more bicyclic nucleosides wherein the bridge comprises a 4' to 2' bicyclic nucleoside. Examples of such 4' to 2' bicyclic nucleosides, include, but are not limited to, one of the formulae: 4'-(CH$_2$)—O-2' (LNA); 4'-(CH$_2$)—S-2'; 4'-(CH$_2$)$_2$—O-2' (ENA); 4'-CH(CH$_3$)—O-2' and 4'-CH(CH$_2$OCH$_3$)—O-2*, and analogs thereof (see, U.S. Pat. No. 7,399,845, issued on Jul. 15, 2008); 4'-C(CH$_3$)(CH$_3$)—O-2', and analogs thereof (see, published PCT International Application WO2009/006478, published Jan. 8, 2009); 4'-CH$_2$—N(OCH$_3$)-2', and analogs thereof (see, published PCT International Application WO2008/150729, published Dec. 11, 2008); 4'-CH$_2$—O—N(CH$_3$)-2' (see, published U.S. Patent Application US2004/0171570, published Sep. 2, 2004); 4'-CH$_2$—N(R)—O-2', wherein R is H, C$_1$-C$_{10}$ alkyl, or a protecting group (see, U.S. Pat. No. 7,427,672, issued on Sep. 23, 2008); 4'-CH$_2$—C(H)(CH$_3$)-2' (see, Chattopadhyaya, et al, J. Org. Chem., 2009, 74, 118-134); and 4'-CH$_2$—C(=CH$_2$)-2', and analogs thereof (see, published PCT International Application WO 2008/154401, published on Dec. 8, 2008). Also see, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc, 129(26) 8362-8379 (Jul. 4, 2007); Elayadi et al., Curr. Opinion Invens. Drugs, 2001, 2, 558-561; Braasch et al., Chem. Biol, 2001, 8, 1-7; Oram et al, Curr. Opinion Mol. Ther., 2001, 3, 239-243; U.S. Pat. Nos. 6,670,461, 7,053, 207, 6,268,490, 6,770,748, 6,794,499, 7,034,133, 6,525,191, 7,399,845; published PCT International applications WO 2004/106356, WO 94/14226, WO 2005/021570, and WO 2007/134181; U.S. Patent Publication Nos. US2004/0171570, US2007/0287831, and US2008/0039618; and U.S. patent Ser. Nos. 12/129,154, 60/989,574, 61/026,995, 61/026,998, 61/056,564, 61/086,231, 61/097,787, and 61/099,844; and PCT International Application Nos. PCT/US2008/064591, PCT/US2008/066154, and PCT/US2008/068922. Each of the foregoing bicyclic nucleosides can be prepared having one or more stereochemical sugar configurations including for example a-L-ribofuranose and beta-D-ribofuranose (see PCT international application PCT DK98/00393, published on Mar. 25, 1999 as WO 99/14226).

In some embodiments, bicyclic sugar moieties nucleosides include, but are not limited to, compounds having at least one bridge between the 4' and the 2' position of the pentofuranosyl sugar moiety wherein such bridges independently comprises 1 or from 2 to 4 linked groups independently selected from —[CiR$_a$XR$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(Ra)—; wherein: x is 0, 1, or 2; n is 1, 2, 3, or 4; each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_6$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C1-C$_{12}$ aminoalkyl, substituted C$_1$-C$_{12}$ aminoalkyl, or a protecting group.

In some embodiments, the bridge of a bicyclic sugar moiety is, —[C(R$_a$)(Rb)]$_n$—, —[C(R$_a$)(R$_b$)]$_n$—O—, —C(R$_a$R$_b$)—N(R)—O— or, —C(R$_a$R$_b$)—O—N(R)—. In some embodiments, the bridge is 4'-CH$_2$-2', 4'-(CH$_2$)$_2$-2', 4'-(CH$_2$)$_3$-2', 4'-CH$_2$—O-2', 4*-(CH$_2$)2-O-2', 4'-CH$_2$—O—N(R)-2', and 4'-CH$_2$—N(R)—O-2'-, wherein each R is, independently, H, a protecting group, or C$_1$-C$_{12}$ alkyl.

In some embodiments, bicyclic nucleosides are further defined by isomeric configuration. For example, a nucleoside comprising a 4'-2' methylene-oxy bridge, may be in the a-L configuration or in the beta-D configuration. Previously, a-L-methyleneoxy (4'-CH$_2$—O-2') BNA's have been incorporated into antisense oligonucleotides that showed antisense activity (Frieden et al, Nucleic Acids Research, 2003, 21, 6365-6372).

In some embodiments, bicyclic nucleosides include, but are not limited to, (A) a-L-Methyleneoxy (4'-CH$_2$—O-2') BNA, (B) beta-D-Methyleneoxy (4'-CH$_2$—O-2') BNA, (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F), Methyl(methyleneoxy) (4'-CH(CH$_3$)—O-2') BNA, (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

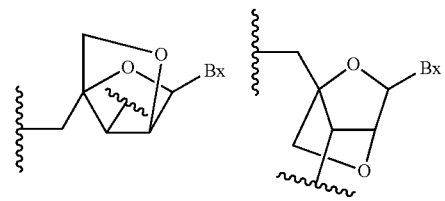

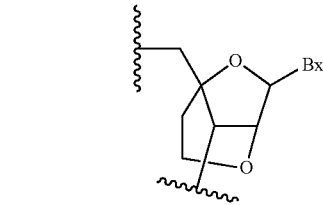

(G)

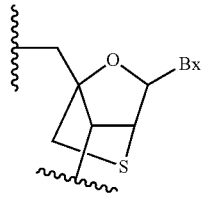

(H)

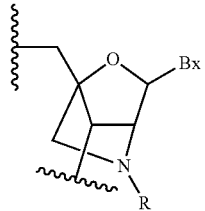

(I)

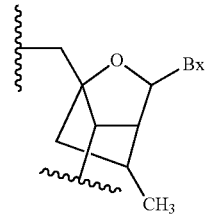

(J)

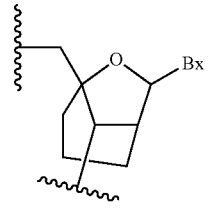

wherein Bx is the base moiety and R is, independently, H, a protecting group or C$_1$-C$_2$ alkyl. In some embodiments, bicyclic nucleoside having Formula I:

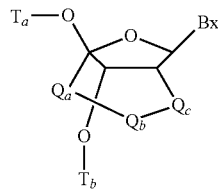

wherein:

Bx is a heterocyclic base moiety;

-$Q_a$-$Q_b$-$Q_c$- is —$CH_2$—N(Rc)-$CH_2$—, —C(=O)—N($R_c$)—$CH_2$—, —$CH_2$—O—N(Rc)-, —$CH_2$—N(Rc)-O—, or —N(Rc)-O—$CH_2$;

$R_c$ is $C_1$-$C_{12}$ alkyl or an amino protecting group; and $T_a$ and $T_b$ are each, independently, H, a hydroxyl protecting group, a conjugate group, a reactive phosphorus group, a phosphorus moiety, or a covalent attachment to a support medium.

In some embodiments, bicyclic nucleoside having Formula II:

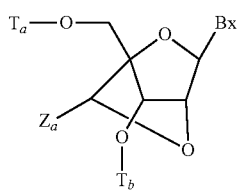

wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium; $Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol, or substituted thio.

In some embodiments, each of the substituted groups is, independently, mono or poly substituted with substituent groups independently selected from halogen, oxo, hydroxyl, $OJ_c$, $NJ_d$, $SJ_c$, $N_3$, OC(=X)$J_c$, and $NJ_e$C(=X)$NJ_cJ_d$, wherein each $J_c$, $J_d$, and $J_e$ is, independently, H, $C_1$-$C_6$ alkyl, or substituted $C_1$-$C_6$ alkyl and X is O or $NJ_c$.

In some embodiments, bicyclic nucleoside having Formula III:

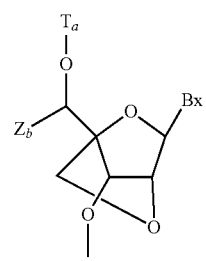

wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

$R_d$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, or substituted acyl (C(=O)—).

In some embodiments, bicyclic nucleoside having Formula IV:

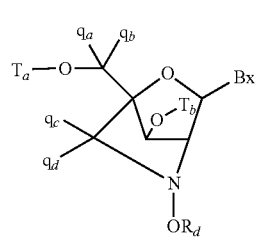

wherein:

Bx is a heterocyclic base moiety;

$T_a$ and $T_b$ are each, independently H, a hydroxyl protecting group, a conjugate group, a reactive phosphorus group, a phosphorus moiety, or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl; each $q_b$, $q_c$ and $q_d$ is, independently, H, halogen, $C_1$-$C_6$ alkyl, substituted $C_1$-$C_6$ alkyl, $C_2$-$C_e$ alkenyl, substituted $C_2$-$C_6$ alkenyl, $C_2$-$C_6$ alkynyl, or substituted $C_2$-$C_6$ alkynyl, $C_1$-$C_6$ alkoxyl, substituted $Q$-$C_6$ alkoxyl, acyl, substituted acyl, $C_1$-$C_6$ aminoalkyl, or substituted $C_1$-$C_6$ aminoalkyl;

In some embodiments, bicyclic nucleoside having Formula V:

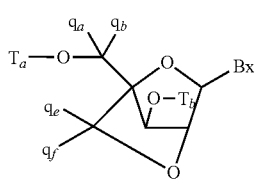

wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium; $q_a$, $q_b$, $q_c$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; or $q_e$ and $q_f$ together are =C($q_g$)($q_h$); $q_g$ and $q_h$ are each, independently, H, halogen, $C_1$-$C_{12}$ alkyl, or substituted $C_1$-$C_{12}$ alkyl. The synthesis and preparation of the methyleneoxy (4'-$CH_2$—O-2') BNA monomers adenine, cytosine, guanine, 5-methylcytosine, thymine, and uracil, along with their oligomerization, and nucleic acid recognition properties have been described (see, e.g., Koshkin et al., Tetrahedron, 1998, 54, 3607-3630). BNAs and preparation thereof are also described in WO 98/39352 and WO 99/14226.

Analogs of methyleneoxy (4'-CH$_2$—O-2') BNA, methyleneoxy (4'-CH$_2$—O-2') BNA, and 2'-thio-BNAs, have also been prepared {see, e.g., Kumar et al., Bioorg. Med. Chem. Lett., 1998, 8, 2219-2222). Preparation of locked nucleoside analogs comprising oligodeoxyribonucleotide duplexes as substrates for nucleic acid polymerases has also been described (see, e.g., Wengel et al., WO 99/14226). Furthermore, synthesis of 2'-amino-BNA, a novel comformationally restricted high-affinity oligonucleotide analog, has been described in the art (see, e.g., Singh et al., J. Org. Chem., 1998, 63, 10035-10039). In addition, 2'-amino- and 2'-methylamino-BNA's have been prepared and the thermal stability of their duplexes with complementary RNA and DNA strands has been previously reported.

In some embodiments, the bicyclic nucleoside has Formula VI:

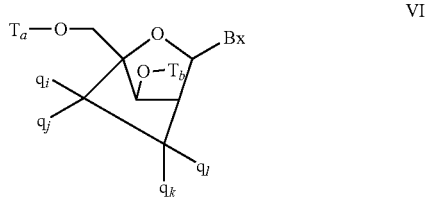

VI wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium; each qj, qj, $q_k$ and ql is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$alkynyl, substituted $C_2$-$C_{12}$ alkynyl, $C_1$-$C_{12}$ alkoxyl, substituted $C_2$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$, or (H)C(=S)$NJ_jJ_k$; and qi and $q_j$ or ql and $q_k$ together are =C($q_g$)($q_h$), wherein $q_g$ and $q_h$ are each, independently, H, halogen, $C_1$-$C_{12}$ alkyl, or substituted $C_1$-$C_6$ alkyl.

One carbocyclic bicyclic nucleoside having a 4'-(CH$_2$)$_3$-2' bridge and the alkenyl analog, bridge 4'-CH=CH—CH$_2$-2', have been described (see, e.g., Freier et al, Nucleic Acids Research, 1997, 25(22), 4429-4443 and Albaek et al, J. Org. Chem., 2006, 71, 7731-77 '40). The synthesis and preparation of carbocyclic bicyclic nucleosides along with their oligomerization and biochemical studies have also been described (see, e.g., Srivastava et al, J. Am. Chem. Soc. 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting the 2' carbon atom and the 4' carbon atom.

As used herein, "monocylic nucleosides" refer to nucleosides comprising modified sugar moieties that are not bicyclic sugar moieties. In some embodiments, the sugar moiety, or sugar moiety analogue, of a nucleoside may be modified or substituted at any position.

As used herein, "2'-modified sugar" means a furanosyl sugar modified at the 2' position. In some embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In some embodiments, 2' modifications are selected from substituents including, but not limited to: O[(CH$_2$)$_n$O]$_m$CH$_3$, O(CH$_2$)$_n$NH$_2$, O(CH$_2$)$_n$CH$_3$, O(CH$_2$)$_n$ONH$_2$, OCH$_2$C(=O)N(H)CH$_3$, and O(CH2)$_n$ON[(CH$_2$)$_n$CH$_3$]2, where n and m are from 1 to about 10. Other 2'-substituent groups can also be selected from: $C_1$-$C_{12}$ alkyl; substituted alkyl; alkenyl; alkynyl; alkaryl; aralkyl; O-alkaryl or O-aralkyl; SH; SCH$_3$; OCN; Cl; Br; CN; CF$_3$; OCF$_3$; SOCH$_3$; S0$_2$CH$_3$; ONO$_2$; NO$_2$; N$_3$; NH$_2$; heterocycloalkyl; heterocycloalkaryl; aminoalkylamino; polyalkylamino; substituted silyl; an R; a cleaving group; a reporter group; an intercalator; a group for improving pharmacokinetic properties; and a group for improving the pharmacodynamic properties of an antisense compound, and other substituents having similar properties. In some embodiments, modified nucleosides comprise a 2'-MOE side chain {see, e.g., Baker et al., J. Biol. Chem., 1997, 272, 1 1944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2-MOE substituent also have been shown to be antisense inhibitors of gene expression with promising features for in vivo use {see, e.g., Martin, P., He/v. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926). As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified ?THP nucleosides include, but are not limited to, what is referred to in the art as hexitol nucleic acid (HNA), anitol nucleic acid (ANA), manitol nucleic acid (MNA) {see Leumann, C J. Bioorg. and Med. Chem. (2002) 10:841-854), fluoro HNA (F-HNA), or those compounds having Formula X:

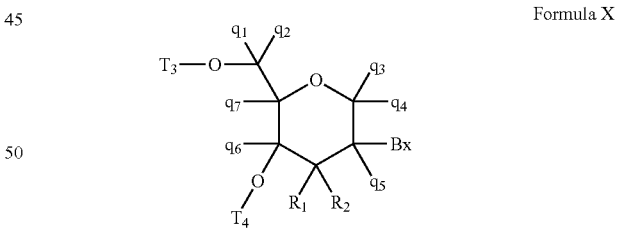

Formula X

X wherein independently for each of said at least one tetrahydropyran nucleoside analog of Formula X:

Bx is a heterocyclic base moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and T4 is H, a hydroxyl protecting group, a linked conjugate group, or a 5' or 3'-terminal group; $q_1$ $q_2$ $q_3$ $q_4$ $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and one of $R_1$ and $R_2$ is hydrogen and the other is selected from halogen, substituted or unsubstituted alkoxy, NJ$_1$J$_2$, SJ$_1$, N$_3$, OC(=X)J$_1$, OC(=X)NJ$_1$J$_2$, NJ$_3$C(=X) NJ$_1$J$_2$, and CN, wherein X is O, S, or NJ$_1$ and each J$_1$, J$_2$, and J$_3$ is, independently, H or C$_1$-C$_6$ alkyl.

In some embodiments, the modified THP nucleosides of Formula X are provided wherein q$_m$, q$_n$, q$_p$, q$_r$, q$_s$, q$_t$, and q$_u$ are each H. In some embodiments, at least one of q$_m$, q$_n$, q$_p$, q$_r$, q$_s$, q$_t$ and q$_u$ is other than H. In some embodiments, at least one of q$_m$, q$_n$, q$_p$, q$_r$, q$_s$, q$_t$ and q$_u$ is methyl. In some embodiments, THP nucleosides of Formula X are provided wherein one of R$_1$ and R$_2$ is F. In some embodiments, R$_1$ is fluoro and R$_2$ is H, R$_1$ is methoxy and R$_2$ is H, and R$_1$ is methoxyethoxy and R$_2$ is H.

As used herein, "2'-modified" or "2'-substituted" refers to a nucleoside comprising a sugar comprising a substituent at the 2' position other than H or OH. 2'-modified nucleosides, include, but are not limited to nucleosides with non-bridging 2'substituents, such as allyl, amino, azido, thio, O-allyl, O—C$_1$-C$_{10}$ alkyl, —OCF$_3$, O—(CH$_2$)$_2$—O—CH$_3$, 2'-O (CH$_2$)$_2$SCH$_3$, O—(CH$_2$)$_2$—O— N(R$_m$)(R$_n$), or O—CH$_2$—C(=O)—N(R$_m$)(R$_n$), where each R$_m$ and R$_n$ is, independently, H or substituted or unsubstituted C$_1$-C$_{10}$ alkyl. 2'-modified nucleosides may further comprise other modifications, for example, at other positions of the sugar and/or at the nucleobase.

As used herein, "2'-F" refers to a sugar comprising a fluoro group at the 2' position.

As used herein, "2'-OMe" or "2'-OCH$_3$" or "2'-O-methyl" each refers to a nucleoside comprising a sugar comprising an —OCH$_3$ group at the 2' position of the sugar ring.

As used herein, "oligonucleotide" refers to a compound comprising a plurality of linked nucleosides.

In some embodiments, one or more of the plurality of nucleosides is modified. In some embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds {see, e.g., review article: Leumann, J. C, Bioorganic and Medicinal Chemistry, 2002, 10, 841-854). Such ring systems can undergo various additional substitutions to enhance activity. Methods for the preparations of modified sugars are well known to those skilled in the art. In nucleotides having modified sugar moieties, the nucleobase moieties (natural, modified, or a combination thereof) are maintained for hybridization with an appropriate nucleic acid target.

In some embodiments, antisense compounds comprise one or more nucleotides having modified sugar moieties. In some embodiments, the modified sugar moiety is 2'-MOE. In some embodiments, the 2'-MOE modified nucleotides are arranged in a gapmer motif. In some embodiments, the modified sugar moiety is a cEt. In some embodiments, the cEt modified nucleotides are arranged throughout the wings of a gapmer motif.

In some embodiments, in the BNA (LNA), R$^{4*}$ and R$^{2*}$ together designate the biradical —O—CH(CH$_2$OCH$_3$)— (2'O-methoxyethyl bicyclic nucleic acid—Seth at al., 2010, J. Org. Chem). —in either the R- or S-configuration.

In some embodiments, in the BNA (LNA), R$^{4*}$ and R$^{2*}$ together designate the biradical —O—CH(CH$_2$CH$_3$)— (2'O-ethyl bicyclic nucleic acid—Seth at al., 2010, J. Org. Chem). —in either the R- or S-configuration.

In some embodiments, in the BNA (LNA), R$^{4*}$ and R$^{2*}$ together designate the biradical —O—CH(CH$_3$)—. —in either the R- or S-configuration. In some embodiments, R$^{4*}$ and R$^{2*}$ together designate the biradical —O—CH$_2$—O—CH$_2$— (Seth at al., 2010, J. Org. Chem).

In some embodiments, in the BNA (LNA), R$^{4*}$ and R$^{2*}$ together designate the biradical —O—NR—CH$_3$— (Seth at al., 2010, J. Org. Chem).

In some embodiments, the LNA units have a structure selected from the following group:

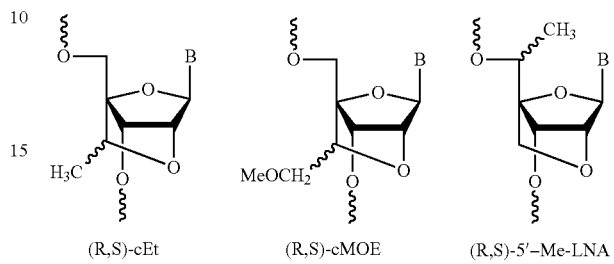

(R,S)-cEt    (R,S)-cMOE    (R,S)-5'–Me-LNA

Incorporation of affinity-enhancing nucleotide analogues in the oligomer, such as BNA, (e.g.) LNA or 2'-substituted sugars, can allow the size of the specifically binding oligomer to be reduced, and may also reduce the upper limit to the size of the oligomer before non-specific or aberrant binding takes place.

In some embodiments, the oligomer comprises at least 1 nucleoside analogue. In some embodiments the oligomer comprises at least 2 nucleotide analogues. In some embodiments, the oligomer comprises from 3-8 nucleotide analogues, e.g. 6 or 7 nucleotide analogues. In the by far most preferred embodiments, at least one of said nucleotide analogues is a BNA, such as locked nucleic acid (LNA); for example at least 3 or at least 4, or at least 5, or at least 6, or at least 7, or 8, of the nucleotide analogues may be BNA, such as LNA. In some embodiments all the nucleotides analogues may be BNA, such as LNA.

It will be recognized that when referring to a preferred nucleotide sequence motif or nucleotide sequence, which consists of only nucleotides, the oligomers of the invention which are defined by that sequence may comprise a corresponding nucleotide analogue in place of one or more of the nucleotides present in said sequence, such as BNA units or other nucleotide analogues, which raise the duplex stability/T$_m$ of the oligomer/target duplex (i.e. affinity enhancing nucleotide analogues).

A preferred nucleotide analogue is LNA, such as oxy-LNA (such as beta-D-oxy-LNA, and alpha-L-oxy-LNA), and/or amino-LNA (such as beta-D-amino-LNA and alpha-L-amino-LNA) and/or thio-LNA (such as beta-D-thio-LNA and alpha-L-thio-LNA) and/or ENA (such as beta-D-ENA and alpha-L-ENA).

In some embodiments, the oligomer of the invention, such as region A, may comprise BNA or LNA units and other nucleotide analogues. further nucleotide analogues present within the oligomer of the invention are independently selected from, for example: 2'-O-alkyl-RNA units, 2'-amino-DNA units, 2'-fluoro-DNA units, BNA units, e.g. LNA units, arabino nucleic acid (ANA) units, 2'-fluoro-ANA units, HNA units, INA (intercalating nucleic acid-Christensen, 2002. Nucl. Acids. Res. 2002 30: 4918-4925, hereby incorporated by reference) units and 2'MOE units. In some embodiments there is only one of the above types of nucleotide analogues present in the oligomer of the invention, such as the first region, or contiguous nucleotide sequence thereof.

In some embodiments, the oligomer according to the invention (region A) may therefore comprises at least one BNA, e.g. Locked Nucleic Acid (LNA) unit, such as 1, 2, 3, 4, 5, 6, 7, or 8 BNA/LNA units, such as from 3-7 or 4 to 8 BNA/LNA units, or 3, 4, 5, 6 or 7 BNA/LNA units. In some embodiments, all the nucleotide analogues are BNA, such as LNA. In some embodiments, the oligomer may comprise both beta-D-oxy-LNA, and one or more of the following LNA units: thio-LNA, amino-LNA, oxy-LNA, and/or ENA in either the beta-D or alpha-L configurations or combinations thereof. In some embodiments all BNA, such as LNA, cytosine units are 5'methyl-Cytosine. In some embodiments of the invention, the oligomer (such as the first and optionally second regions) may comprise both BNA and LNA and DNA units. In some embodiments, the combined total of LNA and DNA units is 10-25, such as 10-24, preferably 10-20, such as 10-18, such as 12-16. In some embodiments of the invention, the nucleotide sequence of the oligomer, of first region thereof, such as the contiguous nucleotide sequence consists of at least one BNA, e.g. LNA and the remaining nucleotide units are DNA units. In some embodiments the oligomer, or first region thereof, comprises only BNA, e.g. LNA, nucleotide analogues and naturally occurring nucleotides (such as RNA or DNA, most preferably DNA nucleotides), optionally with modified internucleotide linkages such as phosphorothioate.

RNAse Recruitment

It is recognized that an oligonucleotide may function via non RNase-mediated degradation of target mRNA, such as by steric hindrance of translation, or other methods, however, the preferred oligonucleotides of the invention are capable of recruiting an endoribonuclease (RNase), such as RNase H.

It is preferable that the oligonucleotide, or contiguous nucleotide sequence, comprises of a region of at least 6, such as at least 7 consecutive nucleotide units, such as at least 8 or at least 9 consecutive nucleotide units, including 7, 8, 9, 10, 11, 12, 13, 14, 15 or 16 consecutive nucleotides, which, when formed in a duplex with the complementary target RNA is capable of recruiting RNase. The contiguous sequence which is capable of recruiting RNAse may be region B as referred to in the context of a gapmer as described herein. In some embodiments the size of the contiguous sequence which is capable of recruiting RNAse, such as region B, may be higher, such as 10, 11, 12, 13, 14, 15, 16, 17, 18, 19 or 20 nucleotide units.

EP 1 222 309 provides in vitro methods for determining RNaseH activity, which may be used to determine the ability to recruit RNaseH. An oligonucleotide is deemed capable of recruiting RNaseH if, when provided with the complementary RNA target, it has an initial rate, as measured in pmol/l/min, of at least 1%, such as at least 5%, such as at least 10% or more than 20% of the of the initial rate determined using a DNA only oligonucleotide, having the same base sequence but containing only DNA monomers, with no 2' substitutions, with phosphorothioate linkage groups between all monomers in the oligonucleotide, using the methodology provided by Example 91-95 of EP 1 222 309.

In some embodiments, an oligonucleotide is deemed essentially incapable of recruiting RNaseH if, when provided with the complementary RNA target, and RNaseH, the RNaseH initial rate, as measured in pmol/l/min, is less than 1%, such as less than 5%, such as less than 10% or less than 20% of the initial rate determined using the equivalent DNA only oligonucleotide, with no 2' substitutions, with phosphorothioate linkage groups between all nucleotides in the oligonucleotide, using the methodology provided by Example 91-95 of EP 1 222 309.

In other embodiments, an oligonucleotide is deemed capable of recruiting RNaseH if, when provided with the complementary RNA target, and RNaseH, the RNaseH initial rate, as measured in pmol/l/min, is at least 20%, such as at least 40%, such as at least 60%, such as at least 80% of the initial rate determined using the equivalent DNA only oligonucleotide, with no 2' substitutions, with phosphorothioate linkage groups between all nucleotides in the oligonucleotide, using the methodology provided by Example 91-95 of EP 1 222 309.

Typically the region of the oligonucleotide which forms the consecutive nucleotide units which, when formed in a duplex with the complementary target RNA is capable of recruiting RNase consists of nucleotide units which form a DNA/RNA like duplex with the RNA target and include both DNA units and LNA units which are in the alpha-L configuration, particularly preferred being alpha-L-oxy LNA.

The oligonucleotides of the invention may comprise a nucleotide sequence which comprises both nucleotides and nucleotide analogues, and may be in the form of a gapmer, a headmer or a mixmer.

A "headmer" is defined as an oligonucleotide that comprises a region X and a region Y that is contiguous thereto, with the 5'-most monomer of region Y linked to the 3'-most monomer of region X. Region X comprises a contiguous stretch of non-RNase recruiting nucleoside analogues and region Y comprises a contiguous stretch (such as at least 7 contiguous monomers) of DNA monomers or nucleoside analogue monomers recognizable and cleavable by the RNase.

A "tailmer" is defined as an oligonucleotide that comprises a region X and a region Y that is contiguous thereto, with the 5'-most monomer of region Y linked to the 3'-most monomer of the region X. Region X comprises a contiguous stretch (such as at least 7 contiguous monomers) of DNA monomers or nucleoside analogue monomers recognizable and cleavable by the RNase, and region X comprises a contiguous stretch of non-RNase recruiting nucleoside analogues.

Other "chimeric" oligonucleotides, called "mixmers", consist of an alternating composition of (i) DNA monomers or nucleoside analogue monomers recognizable and cleavable by RNase, and (ii) non-RNase recruiting nucleoside analogue monomers.

In some embodiments, in addition to enhancing affinity of the oligonucleotide for the target region, some nucleoside analogues also mediate RNase (e.g., RNaseH) binding and cleavage. Since α-L-LNA monomers recruit RNaseH activity to a certain extent, in some embodiments, gap regions (e.g., region Y' as referred to herein) of oligonucleotides containing α-L-LNA monomers consist of fewer monomers recognizable and cleavable by the RNaseH, and more flexibility in the mixmer construction is introduced.

Gapmer Design

In some embodiments, the oligomer of the invention, such as the first region, comprises or is a gapmer. A gapmer oligomer is an oligomer which comprises a contiguous stretch of nucleotides which is capable of recruiting an RNAse, such as RNAseH, such as a region of at least 6 or 7 DNA nucleotides, referred to herein in as region Y' (Y'), wherein region Y' is flanked both 5' and 3' by regions of affinity enhancing nucleotide analogues, such as from 1-6 nucleotide analogues 5' and 3' to the contiguous stretch of nucleotides which is capable of recruiting RNAse—these regions are referred to as regions X' (X') and Z' (Z')

respectively. Examples of gapmers are disclosed in WO2004/046160, WO2008/113832, and WO2007/146511.

In some embodiments, the monomers which are capable of recruiting RNAse are selected from the group consisting of DNA monomers, alpha-L-LNA monomers, C4' alkylayted DNA monomers (see PCT/EP2009/050349 and Vester et al., Bioorg. Med. Chem. Lett. 18 (2008) 2296-2300, hereby incorporated by reference), and UNA (unlinked nucleic acid) nucleotides (see Fluiter et al., Mol. Biosyst., 2009, 10, 1039 hereby incorporated by reference). UNA is unlocked nucleic acid, typically where the C2-C3 C—C bond of the ribose has been removed, forming an unlocked "sugar" residue. Preferably the gapmer comprises a (poly)nucleotide sequence of formula (5' to 3'), X'—Y'—Z', wherein; region X' (X') (5' region) consists or comprises of at least one nucleotide analogue, such as at least one BNA (e.g. LNA) unit, such as from 1-6 nucleotide analogues, such as BNA (e.g. LNA) units, and; region Y' (Y') consists or comprises of at least five consecutive nucleotides which are capable of recruiting RNAse (when formed in a duplex with a complementary RNA molecule, such as the mRNA target), such as DNA nucleotides, and; region Z' (Z') (3' region) consists or comprises of at least one nucleotide analogue, such as at least one BNA (e.g LNA unit), such as from 1-6 nucleotide analogues, such as BNA (e.g. LNA) units.

In some embodiments, region X' consists of 1, 2, 3, 4, 5 or 6 nucleotide analogues, such as BNA (e.g. LNA) units, such as from 2-5 nucleotide analogues, such as 2-5 LNA units, such as 3 or 4 nucleotide analogues, such as 3 or 4 LNA units; and/or region Z consists of 1, 2, 3, 4, 5 or 6 nucleotide analogues, such as BNA (e.g. LNA) units, such as from 2-5 nucleotide analogues, such as 2-5 BNA (e.g. LNA) units), such as 3 or 4 nucleotide analogues, such as 3 or 4 BNA (e.g. LNA) units.

In some embodiments Y' consists or comprises of 5, 6, 7, 8, 9, 10, 11 or 12 consecutive nucleotides which are capable of recruiting RNAse, or from 6-10, or from 7-9, such as 8 consecutive nucleotides which are capable of recruiting RNAse. In some embodiments region Y' consists or comprises at least one DNA nucleotide unit, such as 1-12 DNA units, preferably from 4-12 DNA units, more preferably from 6-10 DNA units, such as from 7-10 DNA units, most preferably 8, 9 or 10 DNA units.

In some embodiments region X' consist of 3 or 4 nucleotide analogues, such as BNA (e.g. LNA), region X' consists of 7, 8, 9 or 10 DNA units, and region Z' consists of 3 or 4 nucleotide analogues, such as BNA (e.g. LNA). Such designs include (X'—Y'—Z') 3-10-3, 3-10-4, 4-10-3, 3-9-3, 3-9-4, 4-9-3, 3-8-3, 3-8-4, 4-8-3, 3-7-3, 3-7-4, 4-7-3.

Further gapmer designs are disclosed in WO2004/046160, which is hereby incorporated by reference. WO2008/113832, which claims priority from U.S. provisional application 60/977,409 hereby incorporated by reference, refers to 'shortmer' gapmer oligomers. In some embodiments, oligomers presented here may be such shortmer gapmers.

In some embodiments the oligomer, e.g. region X', is consisting of a contiguous nucleotide sequence of a total of 10, 11, 12, 13 or 14 nucleotide units, wherein the contiguous nucleotide sequence comprises or is of formula (5'-3') X'—Y'—Z' wherein; X' consists of 1, 2 or 3 nucleotide analogue units, such as BNA (e.g. LNA) units; Y' consists of 7, 8 or 9 contiguous nucleotide units which are capable of recruiting RNAse when formed in a duplex with a complementary RNA molecule (such as a mRNA target); and Z' consists of 1, 2 or 3 nucleotide analogue units, such as BNA (e.g. LNA) units.

In some embodiments X' consists of 1 BNA (e.g. LNA) unit. In some embodiments X' consists of 2 BNA (e.g. LNA) units. In some embodiments X' consists of 3 BNA (e.g. LNA) units. In some embodiments Z' consists of 1 BNA (e.g. LNA) units. In some embodiments Z' consists of 2 BNA (e.g. LNA) units. In some embodiments Z' consists of 3 BNA (e.g. LNA) units. In some embodiments Y' consists of 7 nucleotide units. In some embodiments Y' consists of 8 nucleotide units. In some embodiments Y' consists of 9 nucleotide units. In certain embodiments, region Y' consists of 10 nucleoside monomers. In certain embodiments, region Y' consists or comprises 1-10 DNA monomers. In some embodiments Y' comprises of from 1-9 DNA units, such as 2, 3, 4, 5, 6, 7, 8 or 9 DNA units. In some embodiments Y' consists of DNA units. In some embodiments Y' comprises of at least one BNA unit which is in the alpha-L configuration, such as 2, 3, 4, 5, 6, 7, 8 or 9 LNA units in the alpha-L-configuration. In some embodiments Y' comprises of at least one alpha-L-oxy BNA/LNA unit or wherein all the LNA units in the alpha-L-configuration are alpha-L-oxy LNA units. In some embodiments the number of nucleotides present in X'—Y'—Z' are selected from the group consisting of (nucleotide analogue units—region Y'—nucleotide analogue units): 1-8-1, 1-8-2, 2-8-1, 2-8-2, 3-8-3, 2-8-3, 3-8-2, 4-8-1, 4-8-2, 1-8-4, 2-8-4, or; 1-9-1, 1-9-2, 2-9-1, 2-9-2, 2-9-3, 3-9-2, 1-9-3, 3-9-1, 4-9-1, 1-9-4, or; 1-10-1, 1-10-2, 2-10-1, 2-10-2, 1-10-3, 3-10-1. In some embodiments the number of nucleotides in X'—Y'—Z' are selected from the group consisting of: 2-7-1, 1-7-2, 2-7-2, 3-7-3, 2-7-3, 3-7-2, 3-7-4, and 4-7-3. In certain embodiments, each of regions X' and Y' consists of three BNA (e.g. LNA) monomers, and region Y' consists of 8 or 9 or 10 nucleoside monomers, preferably DNA monomers. In some embodiments both X' and Z' consists of two BNA (e.g. LNA) units each, and Y' consists of 8 or 9 nucleotide units, preferably DNA units. In various embodiments, other gapmer designs include those where regions X' and/or Z' consists of 3, 4, 5 or 6 nucleoside analogues, such as monomers containing a 2'-O-methoxyethyl-ribose sugar (2'-MOE) or monomers containing a 2'-fluoro-deoxyribose sugar, and region Y' consists of 8, 9, 10, 11 or 12 nucleosides, such as DNA monomers, where regions X'—Y'—Z' have 3-9-3, 3-10-3, 5-10-5 or 4-12-4 monomers. Further gapmer designs are disclosed in WO 2007/146511A2, hereby incorporated by reference.

Internucleotide Linkages

The monomers of the oligonucleotides described herein are coupled together via linkage groups. Suitably, each monomer is linked to the 3' adjacent monomer via a linkage group. The person having ordinary skill in the art will understand that, in the context of the present invention, the 5' monomer at the end of an oligonucleotide does not comprise a 5' linkage group, although it may or may not comprise a 5' terminal group.

The phrases "linkage group" and "internucleotide linkage" are intended to mean a group capable of covalently coupling together two nucleotides. Specific and preferred examples include phosphate groups and phosphorothioate groups. In certain embodiments, the antisense oligonucleotides disclosed herein have phosphorothioate internucleotide linkages at each internucleotide linkage (e.g., SEQ ID NOS: 21, 22, 23, 24 and 25). The nucleotides of the oligonucleotide of the invention or contiguous nucleotides sequence thereof are coupled together via linkage groups. Suitably each nucleotide is linked to the 3' adjacent nucleotide via a linkage group.

Suitable internucleotide linkages include those listed within International Application WO 2007/031091, for example the internucleotide linkages listed on the first paragraph of page 34 of WO2007/031091.

It is, in some embodiments, preferred to modify the internucleotide linkage from its normal phosphodiester to one that is more resistant to nuclease attack, such as phosphorothioate or boranophosphate—these two, being cleavable by RNase H, also allow that route of antisense inhibition in reducing the expression of the target gene.

Suitable sulphur (S) containing internucleotide linkages as provided herein may be preferred. Phosphorothioate internucleotide linkages are also preferred, particularly for the gap region (Y') of gapmers. Phosphorothioate linkages may also be used for the flanking regions (X' and Z').

Regions X', Y' and Z', may however comprise internucleotide linkages other than phosphorothioate, such as phosphodiester linkages, particularly, for instance when the use of nucleotide analogues protects the internucleotide linkages within regions X' and Z' from endo-nuclease degradation— such as when regions X' and Z' comprise LNA nucleotides.

The internucleotide linkages in the oligonucleotide may be phosphodiester, phosphorothioate or boranophosphate so as to allow RNase H cleavage of targeted RNA. Phosphorothioate is preferred, for improved nuclease resistance and other reasons, such as ease of manufacture.

In one aspect of the oligonucleotide of the invention, the nucleotides and/or nucleotide analogues are linked to each other by means of phosphorothioate groups.

It is recognised that the inclusion of phosphodiester linkages, such as one or two linkages, into an otherwise phosphorothioate oligonucleotide, particularly between or adjacent to nucleotide analogue units (typically in region X' and or Z') can modify the bioavailability and/or bio-distribution of an oligonucleotide—see International Application WO 2008/053314

In some embodiments, such as the embodiments referred to above, where suitable and not specifically indicated, all remaining linkage groups are either phosphodiester or phosphorothioate, or a mixture thereof. In some embodiments all the internucleotide linkage groups are phosphorothioate.

When referring to specific gapmer oligonucleotide sequences, such as those provided herein it will be understood that, in various embodiments, when the linkages are phosphorothioate linkages, alternative linkages, such as those disclosed herein may be used, for example phosphate (phosphodiester) linkages may be used, particularly for linkages between nucleotide analogues, such as LNA, units. Likewise, when referring to specific gapmer oligonucleotide sequences, such as those provided herein, when the C residues are annotated as 5'methyl modified cytosine, in various embodiments, one or more of the Cs present in the oligonucleotide may be unmodified C residues.

Oligonucleotides

The oligonucleotides of the invention may, for example, comprise a sequence selected from the group consisting of SEQ ID NOS: 9, 10, 11, 12, 13 and 14. In certain embodiments, the oligonucleotides of the invention may comprise a sequence selected from the group consisting of SEQ ID NO: 21, SEQ ID NO: 22, SEQ ID NO: 23, SEQ ID NO: 24 and SEQ ID NO: 25. In some embodiments, the oligonucleotides of the invention may, for example, be selected from the group consisting of the sequences identified in Tables 1 or 4.

Conjugates

In the context of the present invention, the term "conjugate" is intended to indicate a heterogenous molecule formed by the covalent attachment of the oligonucleotide as described herein to one or more non-nucleotide, or non-polynucleotide moieties. Examples of non-nucleotide or non-polynucleotide moieties include macromolecular agents such as proteins, fatty acid chains, sugar residues, glycoproteins, polymers, or combinations thereof. Typically proteins may be antibodies for a target protein. Typical polymers may be polyethylene glycol.

Therefore, in various embodiments, the oligonucleotide of the invention may comprise both a polynucleotide region which typically consists of a contiguous sequence of nucleotides, and a further non-nucleotide region. When referring to the oligonucleotide of the invention consisting of a contiguous nucleotide sequence, the compound may comprise non-nucleotide components, such as a conjugate component.

In various embodiments of the invention the oligonucleotide is linked to ligands/conjugates, which may be used, e.g. to increase the cellular uptake of oligonucleotides. International Application WO 2007/031091 provides suitable ligands and conjugates.

The invention also provides for a conjugate comprising the compound according to the invention as herein described, and at least one non-nucleotide or non-polynucleotide moiety covalently attached to said compound. Therefore, in various embodiments where the compound of the invention consists of a specified nucleic acid or nucleotide sequence, as herein disclosed, the compound may also comprise at least one non-nucleotide or non-polynucleotide moiety (e.g. not comprising one or more nucleotides or nucleotide analogues) covalently attached to said compound.

Conjugation may enhance the activity, cellular distribution or cellular uptake of the oligonucleotide of the invention. Such moieties include, but are not limited to, antibodies, polypeptides, lipid moieties such as a cholesterol moiety, cholic acid, a thioether, e.g. Hexyl-s-tritylthiol, a thiocholesterol, an aliphatic chain, e.g., dodecandiol or undecyl residues, a phospholipids, e.g., di-hexadecyl-rac-glycerol or triethylammonium 1,2-di-o-hexadecyl-rac-glycero-3-h-phosphonate, a polyamine or a polyethylene glycol chain, an adamantane acetic acid, a palmityl moiety, an octadecylamine or hexylamino-carbonyl-oxycholesterol moiety.

The oligonucleotides of the invention may also be conjugated to active drug substances, for example, aspirin, ibuprofen, a sulfa drug, an antidiabetic, an antibacterial or an antibiotic.

In certain embodiments the conjugated moiety is a sterol, such as cholesterol.

In various embodiments, the conjugated moiety comprises or consists of a positively charged polymer, such as a positively charged peptides of, for example from about 1-50, such as 2-20 such as 3-10 amino acid residues in length, and/or polyalkylene oxide such as polyethylglycol (PEG) or polypropylene glycol (see e.g., International Application WO 2008/034123). Suitably the positively charged polymer, such as a polyalkylene oxide may be attached to the oligonucleotide of the invention via a linker such as the releasable linker described in WO 2008/034123.

By way of example, the following conjugate moieties may be used in the conjugates of the invention:

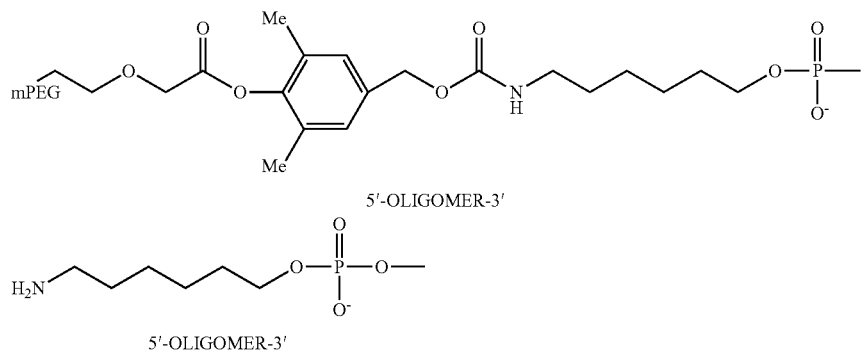

In some embodiments, the oligomeric compound comprises an antisense oligomer such as LNA antisense oligomer, (which may be referred to as region A herein), optionally a biocleavable linker (region B), and a carbohydrate conjugate (which may be referred to as region C). In some embodiments, region B may be a phosphate nucleotide linker. In some embodiments, region B comprises between 1-6 nucleotides, and is covalently linked to the 5' or 3' nucleotide of the A region, such as via a internucleoside linkage group such as a phosphodiester linkage, In some embodiments the carbohydrate moiety is not a linear carbohydrate polymer. The carbohydrate moiety may however be multi-valent, such as, for example 2, 3, 4 or 4 identical or non-identical carbohydrate moieties may be covalently joined to the oligomer, optionally via a linker or linkers. In some embodiments the invention provides a conjugate comprising the oligomer of the invention and a carbohydrate conjugate moiety. In some embodiments the invention provides a conjugate comprising the oligomer of the invention and an asialoglycoprotein receptor targeting moiety conjugate moiety, such as a GalNAc moiety, which may form part of a further region (referred to as region C).

Activated Oligonucleotides

The term "activated oligonucleotide," as used herein, refers to an oligonucleotide of the invention that is covalently linked (i.e., functionalized) to at least one functional moiety that permits covalent linkage of the oligonucleotide to one or more conjugated moieties (i.e., moieties that are not themselves nucleic acids or monomers) to form the conjugates herein described. Typically, a functional moiety will comprise a chemical group that is capable of covalently bonding to the oligonucleotide via, for example, a 3'-hydroxyl group or the exocyclic $NH_2$ group of the adenine base, a spacer that is preferably hydrophilic and a terminal group that is capable of binding to a conjugated moiety (e.g., an amino, sulfhydryl or hydroxyl group). In some embodiments, this terminal group is not protected (e.g., an $NH_2$ group). In other embodiments, the terminal group is protected, for example, by any suitable protecting group such as those described in "Protective Groups in Organic Synthesis" by Theodora W Greene and Peter G M Wuts, 3rd edition (John Wiley & Sons, 1999). Examples of suitable hydroxyl protecting groups include esters such as acetate ester, aralkyl groups such as benzyl, diphenylmethyl, or triphenylmethyl, and tetrahydropyranyl. Examples of suitable amino protecting groups include benzyl, alpha-methylbenzyl, diphenylmethyl, triphenylmethyl, benzyloxycarbonyl, tert-butoxycarbonyl, and acyl groups such as trichloroacetyl or trifluoroacetyl. In some embodiments, the functional moiety is self-cleaving. In other embodiments, the functional moiety is biodegradable (see e.g., U.S. Pat. No. 7,087,229).

In some embodiments, oligonucleotides of the invention are functionalized at the 5' end in order to allow covalent attachment of the conjugated moiety to the 5' end of the oligonucleotide. In other embodiments, oligonucleotides of the invention can be functionalized at the 3' end. In still other embodiments, oligonucleotides of the invention can be functionalized along the backbone or on the heterocyclic base moiety. In yet other embodiments, oligonucleotides of the invention can be functionalized at more than one position independently selected from the 5' end, the 3' end, the backbone and the base.

In some embodiments, activated oligonucleotides of the invention are synthesized by incorporating during the synthesis one or more monomers that is covalently attached to a functional moiety. In other embodiments, activated oligonucleotides of the invention are synthesized with monomers that have not been functionalized, and the oligonucleotide is functionalized upon completion of synthesis. In some embodiments, the oligonucleotides are functionalized with a hindered ester containing an aminoalkyl linker, wherein the alkyl portion has the formula $(CH_2)_w$, wherein w is an integer ranging from 1 to 10, preferably about 6, wherein the alkyl portion of the alkylamino group can be straight chain or branched chain, and wherein the functional group is attached to the oligonucleotide via an ester group (—O—C(O)—$(CH_2)_w$NH).

In other embodiments, the oligonucleotides are functionalized with a hindered ester containing a $(CH_2)_w$-sulfhydryl (SH) linker, wherein w is an integer ranging from 1 to 10, preferably about 6, wherein the alkyl portion of the alkylamino group can be straight chain or branched chain, and wherein the functional group attached to the oligonucleotide via an ester group (—O—C(O)—$(CH_2)_w$SH)

In some embodiments, sulfhydryl-activated oligonucleotides are conjugated with polymer moieties such as polyethylene glycol or peptides (via formation of a disulfide bond).

Activated oligonucleotides containing hindered esters as described above can be synthesized by any method known in the art, and in particular by methods disclosed in International Application WO 2008/034122 and the examples therein In still other embodiments, the oligonucleotides of the invention are functionalized by introducing sulfhydryl, amino or hydroxyl groups into the oligonucleotide by means of a functionalizing reagent substantially as described in U.S. Pat. Nos. 4,962,029 and 4,914,210 (i.e., a substantially linear reagent having a phosphoramidite at one end linked through a hydrophilic spacer chain to the opposing end which comprises a protected or unprotected sulfhydryl, amino or hydroxyl group). Such reagents primarily react with hydroxyl groups of the oligonucleotide. In some embodiments, such activated oligonucleotides have a functionalizing reagent coupled to a 5'-hydroxyl group of the oligonucleotide. In other embodiments, the activated oligonucleotides have a functionalizing reagent coupled to a 3'-hydroxyl group. In still other embodiments, the activated oligonucleotides of the invention have a functionalizing reagent coupled to a hydroxyl group on the backbone of the oligonucleotide. In yet further embodiments, the oligonucleotide of the invention is functionalized with more than one of the functionalizing reagents as described in U.S. Pat. Nos. 4,962,029 and 4,914,210. Methods of synthesizing such functionalizing reagents and incorporating them into monomers or oligonucleotides are disclosed in U.S. Pat. Nos. 4,962,029 and 4,914,210.

In some embodiments, the 5'-terminus of a solid-phase bound oligonucleotide is functionalized with a dienyl phosphoramidite derivative, followed by conjugation of the deprotected oligonucleotide with, e.g., an amino acid or peptide via a Diels-Alder cycloaddition reaction.

In various embodiments, the incorporation of monomers containing 2'-sugar substitutions, such as a 2'-carbamate substituted sugar or a 2'-(O-pentyl-N-phthalimido)-deoxyribose sugar into the oligonucleotide facilitates covalent attachment of conjugated moieties to the sugars of the oligonucleotide. In other embodiments, an oligonucleotide with an amino-containing linker at the 2'-position of one or more monomers is prepared using a reagent such as, for example, 5'-dimethoxytrityl-2'-O-(e-phthalimidylaminopentyl)-2'-deoxyadenosine-3'-N,N-diisopropyl-cyanoethoxy phosphoramidite. (See, e.g., Manoharan, et al., Tetrahedron Letters, (1991) 34:7171.)

In still further embodiments, the oligonucleotides of the invention may have amine-containing functional moieties on the nucleobase, including on the N6 purine amino groups, on the exocyclic N2 of guanine, or on the N4 or 5 positions of cytosine. In various embodiments, such functionalization may be achieved by using a commercial reagent that is already functionalized in the oligonucleotide synthesis.

Some functional moieties are commercially available, for example, heterobifunctional and homobifunctional linking moieties are available from the Pierce Co. (Rockford, Ill.). Other commercially available linking groups are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2, and 3'-Amino-Modifier is also available from Clontech Laboratories Inc. (Palo Alto, Calif.).

Pharmaceutical Compositions

The oligonucleotides of the invention may be used in pharmaceutical formulations and compositions. Suitably, such compositions comprise a pharmaceutically acceptable solvent, such as water or saline, diluent, carrier, salt or adjuvant. PCT/DK2006/000512 provides suitable and preferred pharmaceutically acceptable diluent, carrier, solvent and adjuvants. Suitable dosages, formulations, administration routes, compositions, dosage forms, combinations with other therapeutic agents, pro-drug formulations are also provided in PCT/DK2006/000512.

The present invention also includes pharmaceutical compositions and formulations which include the oligonucleotides of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial (e.g., intrathecal or intraventricular, administration). Oligonucleotides with at least one 2'-O-methoxyethyl substitutions or modification can be particularly useful for oral administration.

Applications

The oligonucleotides of the invention may be utilized as research reagents for, for example, diagnostics, therapeutics and prophylaxis. In research, such oligonucleotides may be used to specifically inhibit the synthesis of FGFR3 (typically by degrading or inhibiting the mRNA and thereby prevent protein formation) in cells and experimental animals thereby facilitating functional analysis of the target or an appraisal of its usefulness as a target for therapeutic intervention.

In diagnostics the oligonucleotides may be used to detect and quantitate FGFR3 expression in cell and tissues by northern blotting, in-situ hybridisation or similar techniques.

For therapeutics, an animal or a human, suspected of having a disease or disorder, which can be treated by modulating the expression of FGFR3 is treated by administering oligonucleotides in accordance with this invention. Further provided are methods of treating a mammal, such as treating a human, suspected of having or being prone to a disease or condition, associated with expression of FGFR3 by administering a therapeutically or prophylactically effective amount of one or more of the oligonucleotides or compositions of the invention. The oligonucleotide, a conjugate or a pharmaceutical composition according to the invention is typically administered in an effective amount.

The invention also provides for the use of the compound or conjugate of the invention as described for the manufacture of a medicament for the treatment of a disorder as referred to herein, or for a method of the treatment of as a disorder as referred to herein.

The invention also provides for a method for treating a disorder as referred to herein said method comprising administering a compound according to the invention as herein described, and/or a conjugate according to the invention, and/or a pharmaceutical composition according to the invention to a patient in need thereof.

Medical Indications

The oligonucleotides and other compositions according to the invention can be used for the treatment of conditions associated with over expression or expression of mutated version of the FGFR3 (e.g., achondroplasia). The invention further provides use of a compound of the invention in the manufacture of a medicament for the treatment of a disease, disorder or condition as referred to herein.

Generally stated, one aspect of the invention is directed to methods of treating a mammal suffering from or susceptible to conditions associated with abnormal levels or aberrant expression of FGFR3 (e.g., relating to the expression of mutated G380R FGFR3), comprising administering to the mammal a therapeutically effective amount of an oligonucleotide targeted to the gene product of a mutated or naturally occurring variant of FGFR3 (e.g., mRNA encoding a mutated FGFR3, such as the G380R mutation) that comprises one or more LNA units. The disease or disorder, as referred to herein, may, in some embodiments be associated with a mutation in the FGFR3 gene or a gene whose protein product is associated with or interacts with FGFR3. Therefore, in some embodiments, the target mRNA is a mutated form of FGFR3 mRNA.

One aspect of the invention is directed to the use of an oligonucleotide or a conjugate for the preparation of a medicament for the treatment of a disease, disorder or condition as referred to herein.

The methods of the invention are preferably employed for treatment or prophylaxis against diseases caused by abnormal levels of FGFR3. Alternatively stated, in some embodiments, the invention is furthermore directed to a method for treating abnormal levels of FGFR3, said method comprising administering a oligonucleotide of the invention, or a conjugate of the invention or a pharmaceutical composition of the invention to a patient in need thereof.

The invention also relates to an oligonucleotide, a composition or a conjugate as defined herein for use as a medicament.

The invention further relates to use of a compound, composition, or a conjugate as defined herein for the manufacture of a medicament for the treatment of abnormal levels of FGFR3 or expression of mutant forms of FGFR3 (such as allelic variants, such as those associated with one of the diseases referred to herein).

Moreover, the invention relates to a method of treating a subject suffering from a disease or condition such as those referred to herein.

A patient who is in need of treatment is a patient suffering from or likely to suffer from the disease or disorder.

In some embodiments, the term "treatment" as used herein refers to both treatment of an existing disease (e.g. a disease or disorder as herein referred to), or prevention of a disease, (i.e., prophylaxis). It will therefore be recognized that treatment as referred to herein may, in some embodiments, be prophylactic.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of FGFR3 is treated by administering oligonucleotides in accordance with this invention. The oligonucleotides of the invention can be utilized in pharmaceutical compositions by adding an effective amount of an oligonucleotide to a suitable pharmaceutically acceptable diluent or carrier.

The antisense compounds of the invention are useful for research and diagnostics, because these compounds hybridize to nucleic acids encoding FGFR3, enabling sandwich and other assays to easily be constructed to exploit this fact. Hybridization of the oligonucleotides of the invention with a nucleic acid encoding FGFR3 can be detected by means known in the art. Such means may include conjugation of an enzyme to the oligonucleotide, radio labelling of the oligonucleotide or any other suitable detection means. Kits using such detection means for detecting the level of FGFR3 protein or mRNA in a sample may also be prepared.

While certain compounds, compositions and methods of the present invention have been described with specificity in accordance with certain embodiments, the following examples serve only to illustrate the compounds of the invention and are not intended to limit the same. Each of the publications, reference materials, GenBank accession numbers and the like referenced herein to describe the background of the invention and to provide additional detail regarding its practice is hereby incorporated by reference in its entirety.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification.

Embodiments of the Invention

1. An oligonucleotide that hybridizes to a nucleic acid comprising SEQ ID NO: 4, wherein said oligonucleotide modulates expression of FGFR3.

2. An oligonucleotide of embodiment 1, wherein said oligonucleotide hybridizes to a region of SEQ ID NO: 4 comprising nucleotide position 1394 of SEQ ID NO: 4.

3. The oligonucleotide of embodiment 1, wherein said oligonucleotide is selected from the group consisting of SEQ ID NO: 9, SEQ ID NO: 10, SEQ ID NO: 11, SEQ ID NO: 12, SEQ ID NO: 13, SEQ ID NO: 14, SEQ ID NO: 21, SEQ ID NO: 22, SEQ ID NO: 23, SEQ ID NO: 24 and SEQ ID NO: 25.

4. The oligonucleotide of embodiment 1, wherein said oligonucleotide is at least 80% identical to an oligonucleotide selected from the group consisting of SEQ ID NO: 9, SEQ ID NO: 10, SEQ ID NO: 11, SEQ ID NO: 12, SEQ ID NO: 13 and SEQ ID NO: 14.

5. The oligonucleotide of embodiment 1, wherein said oligonucleotide is 14 nucleotides in length.

6. The oligonucleotide of embodiment 1, wherein said oligonucleotide is at least 15 nucleotides in length.

7. The oligonucleotide of embodiment 1, wherein said oligonucleotide is at least 16 nucleotides in length.

8. The oligonucleotide of embodiment 1, wherein said oligonucleotide is at least 18 nucleotides in length 9. The oligonucleotide of embodiment 1, wherein said oligonucleotide specifically hybridizes to a region of SEQ ID NO: 4 encoding a G380R mutation.

10. The oligonucleotide of embodiment 1, wherein said oligonucleotide reduces the expression of FGFR3 by at least about 50%.

11. The oligonucleotide of embodiment 1, wherein said oligonucleotide reduces the expression of FGFR3 by at least about 75%.

12. The oligonucleotide of embodiment 1, wherein said oligonucleotide reduces the expression of FGFR3 by at least about 90%.

13. The oligonucleotide of embodiment 1, wherein said oligonucleotide modulates the expression of a mutated form of FGFR3.

14. The oligonucleotide of embodiment 1, wherein said oligonucleotide preferentially modulates expression of a mutated form of FGFR3 in comparison with expression of a wild-type form of FGFR3.

15. The oligonucleotide of embodiment 1, wherein said oligonucleotide inhibits the expression of a mutated form of FGFR3.

16. The oligonucleotide of embodiment 1, wherein said oligonucleotide downregulates the expression of a mutated form of FGFR3.

17. The oligonucleotide of embodiment 1, wherein said oligonucleotide upregulates the expression of a wild-type form of FGFR3 in comparison with expression of a mutated form of FGFR3.

18. The oligonucleotide of embodiment 1, wherein said oligonucleotide does not hybridize to a nucleic acid comprising SEQ ID NO: 1.

19. The oligonucleotide of embodiment 1, wherein said oligonucleotide does not hybridize to a nucleic acid comprising SEQ ID NO: 7 or SEQ ID NO: 8.

20. The oligonucleotide of embodiment 1, wherein said oligonucleotide hybridizes to a nucleic acid comprising SEQ ID NO: 5 or SEQ ID NO: 6.

21. The oligonucleotide of embodiment 1, wherein said oligonucleotide hybridizes to a nucleic acid comprising SEQ ID NO: 4 at codon 380.

22. The oligonucleotide of embodiment 1, wherein said oligonucleotide hybridizes to a nucleic acid comprising SEQ ID NO: 4 at the G380R region.

23. The oligonucleotide of embodiment 1, wherein said oligonucleotide hybridizes to a nucleic acid comprising SEQ ID NO: 4 at position 1138 of codon 380.

24. The oligonucleotide of embodiment 1 wherein said oligonucleotide is an antisense oligonucleotide.

25. The oligonucleotide of embodiment 23, wherein said oligonucleotide is selected from the group consisting of SEQ ID NO: 9, SEQ ID NO: 10, SEQ ID NO: 11, SEQ ID NO: 12, SEQ ID NO: 13, SEQ ID NO: 14, SEQ ID NO: 21, SEQ ID NO: 22, SEQ ID NO: 23, SEQ ID NO: 24 and SEQ ID NO: 25.

26. The oligonucleotide of embodiment 1, wherein said oligonucleotide comprises one or more nucleotide units selected from the group consisting of: Locked Nucleic Acid (LNA) units; 2'-O-alkyl-RNA units, 2'-OMe-RNA units, 2'-amino-DNA units, and 2'-fluoro-DNA units.

27. The oligonucleotide of embodiment 1, wherein said oligonucleotide comprises two or more LNA monomeric units.

28. The oligonucleotide of embodiment 27, wherein the two or more LNA monomeric units are located adjacent to each other.

29. The oligonucleotide of embodiment 27, wherein the two or more LNA monomeric units are located consecutively relative to each other.

30. The oligonucleotide of embodiment 1, wherein modulation of the expression of FGFR3 restores chondrocyte function.

31. The use of an oligonucleotide of embodiment 1 for the treatment of a condition associated with the aberrant expression of FGFR3.

32. The use of an oligonucleotide of embodiment 1 for the treatment of achondroplasia.

33. An oligonucleotide comprising SEQ ID NO: 9, wherein said oligonucleotide modulates expression of FGFR3.

34. An oligonucleotide comprising SEQ ID NO: 10, wherein said oligonucleotide modulates expression of FGFR3.

35. An oligonucleotide comprising SEQ ID NO: 11, wherein said oligonucleotide modulates expression of FGFR3.

36. An oligonucleotide comprising SEQ ID NO: 12, wherein said oligonucleotide modulates expression of FGFR3.

37. An oligonucleotide comprising SEQ ID NO: 13, wherein said oligonucleotide modulates expression of FGFR3.

38. An oligonucleotide which hybridizes to a nucleic acid comprising SEQ ID NO: 1, wherein said oligonucleotide comprises one or more LNA monomeric units, and wherein said oligonucleotide modulates expression of FGFR3.

39. The oligonucleotide of embodiment 38, wherein said oligonucleotide is 8 nucleotides in length.

40. The oligonucleotide of embodiment 38, wherein said oligonucleotide is 15 nucleotides in length.

41. The oligonucleotide of embodiment 38, wherein said oligonucleotide is 18 nucleotides in length 42. The oligonucleotide of claim 38, wherein said oligonucleotide reduces the expression of FGFR3 by at least about 50%.

43. The oligonucleotide of claim 38, wherein said oligonucleotide reduces the expression of FGFR3 by at least about 75%.

44. The oligonucleotide of claim 38, wherein said oligonucleotide reduces the expression of FGFR3 by at least about 90%.

45. The oligonucleotide of claim 38, wherein said oligonucleotide modulates the expression of a mutated form of FGFR3.

46. The oligonucleotide of claim 38, wherein said oligonucleotide inhibits the expression of a mutated form of FGFR3.

47. The oligonucleotide of claim 38, wherein said oligonucleotide downregulates the expression of a mutated form of FGFR3.

48. The oligonucleotide of claim 38, wherein said oligonucleotide upregulates the expression of a wild-type form of FGFR3.

49. The oligonucleotide of embodiment 38, wherein said oligonucleotide hybridizes to a nucleic acid comprising SEQ ID NO: 4.

50. The oligonucleotide of embodiment 38, wherein said oligonucleotide hybridizes to a nucleic acid comprising SEQ ID NO: 4 at position 1138 of codon 380.

51. The oligonucleotide of embodiment 38, wherein said oligonucleotide hybridizes to a nucleic acid comprising SEQ ID NO: 4 at the G380R region.

52. The oligonucleotide of embodiment 38, wherein said oligonucleotide is an antisense oligonucleotide.

53. The oligonucleotide of embodiment 38, wherein said oligonucleotide comprises two or more LNA monomeric units.

54. The oligonucleotide of embodiment 53, wherein the two or more LNA monomeric units are located adjacent to each other.

55. The oligonucleotide of embodiment 53, wherein the two or more LNA monomeric units are located consecutively relative to each other.
56. The oligonucleotide of embodiment 38, wherein modulation of the expression of FGFR3 restores chondrocyte function.
57. The use of an oligonucleotide of embodiment 38, for the treatment of a condition associated with the aberrant expression of FGFR3.
58. The use of an oligonucleotide of embodiment 38, for the treatment of achondroplasia.
59. An oligonucleotide which is useful for the treatment of achondroplasia, wherein said oligonucleotide hybridizes to a nucleic acid comprising SEQ ID NO: 1 or SEQ ID NO: 4, and wherein said oligonucleotide comprises at least one LNA monomeric unit.
60. The oligonucleotide of embodiment 59, wherein said oligonucleotide is 8 nucleotides in length.
61. The oligonucleotide of embodiment 59, wherein said oligonucleotide is 15 nucleotides in length.
62. The oligonucleotide of embodiment 59, wherein said oligonucleotide is 18 nucleotides in length.
63. The oligonucleotide of embodiment 59, wherein said oligonucleotide downregulates the expression of FGFR3.
64. The oligonucleotide of embodiment 59, wherein said oligonucleotide is an antisense oligonucleotide.
65. An oligonucleotide which is useful for the treatment of cancer or achondroplasia, wherein said oligonucleotide hybridizes to the G380R region of a nucleic acid comprising SEQ ID NO: 5, and wherein said oligonucleotide comprises at least one LNA monomeric unit.
66. A method of modulating the expression of FGFR3 mRNA comprising delivering to said FGFR3 mRNA the oligonucleotide of embodiment 1 under conditions appropriate for hybridization of said FGFR3 mRNA with said oligonucleotide, thereby modulating the expression of the FGFR3 mRNA.
67. The method of embodiment 66, wherein modulating the expression of FGFR3 results in a reduced expression of the FGFR3.
68. A method of modulating the expression of FGFR3 comprising contacting said FGFR3 with the oligonucleotide of embodiment 1 under conditions appropriate for hybridization of said FGFR3 with said oligonucleotide, thereby modulating the expression of FGFR3.
69. The method of embodiment 68, wherein modulating the expression of FGFR3 results in a reduced expression of FGFR3.
70. A method of treating a condition associated with aberrant expression of FGFR3, comprising selecting a patient diagnosed with said condition and administering to said patient the oligonucleotide of embodiment 1.
71. A method of treating a condition associated with aberrant expression of FGFR3, comprising selecting a patient diagnosed with said condition and administering to said patient an oligonucleotide of embodiment 38.
72. An oligonucleotide which hybridizes to a nucleic acid comprising SEQ ID NO: 4, wherein said oligonucleotide comprises at least one LNA monomeric unit, and wherein said oligonucleotide does not hybridize to a nucleic acid comprising SEQ ID NO: 1.
73. A pharmaceutical composition comprising an oligonucleotide which is useful for the treatment of cancer, such as bladder cancer or achondroplasia, wherein said oligonucleotide hybridizes to a nucleic acid comprising SEQ ID NO: 1 or SEQ ID NO: 4, and wherein said oligonucleotide comprises at least one LNA monomeric unit.
74. The pharmaceutical composition of embodiment 73, wherein said oligonucleotide is an antisense oligonucleotide.
75. The pharmaceutical composition of embodiment 73, wherein said composition is formulated for pulmonary administration.
76. The pharmaceutical composition of embodiment 73, wherein said composition is formulated for parenteral administration.
77. The pharmaceutical composition of embodiment 73, wherein said oligonucleotide modulates the expression of FGFR3 by hybridizing to a nucleic acid comprising SEQ ID NO: 4.
78. The pharmaceutical composition of embodiment 77, wherein said oligonucleotide does not hybridize to a nucleic acid comprising SEQ ID NO: 1.
79. The pharmaceutical composition of embodiment 73, wherein said oligonucleotide modulates the expression of FGFR3 by hybridizing to a nucleic acid comprising SEQ ID NO: 1.
80. The pharmaceutical composition of embodiment 79, wherein said oligonucleotide does not hybridize to a nucleic acid comprising SEQ ID NO: 4.
81. An oligonucleotide which modulates the expression of FGFR3, wherein said oligonucleotide comprises at least one LNA monomeric unit.
82. An oligonucleotide of about 14-20 nucleotides in length, wherein said oligonucleotide comprises a nucleotide sequence that is at least 80% homologous to the reverse complement SEQ ID NO: 4, or naturally occurring variant thereof.
83. The oligonucleotide of embodiment 82, wherein the contiguous nucleotide sequence comprises no more than one mismatch with the reverse complement of SEQ ID NO: 4.
84. The oligonucleotide of embodiment 82, wherein the nucleotide sequence comprises one or more nucleotide analogues.
85. The oligonucleotide of embodiment 84, wherein the one or more nucleotide analogues comprise a chemically altered sugar moiety as compared to a wild-type nucleotide in a wild-type oligonucleotide.
86. The oligonucleotide of embodiment 85, wherein the one or more nucleotide analogues are selected from the group consisting of locked nucleic acid (LNA) units, 2'-O-alkyl-RNA units, 2'-OMe-RNA units, 2'-amino-DNA units and 2'-fluoro-DNA units.
87. The oligonucleotide of embodiment 84, wherein the one or more nucleotide analogues are LNA.
88. The oligonucleotide of embodiment 82, wherein the oligonucleotide is selected from the group consisting of SEQ ID NO: 21, SEQ ID NO: 22, SEQ ID NO: 23, SEQ ID NO: 24 and SEQ ID NO: 25.
89. The oligonucleotide according to embodiment 82, wherein the oligonucleotide is a gapmer.
90. The oligonucleotide of embodiment 82, wherein the oligonucleotide inhibits the expression of FGFR3 mRNA in a cell which is expressing FGFR3 mRNA.
91. The oligonucleotide of embodiment 90, wherein the FGFR3 mRNA comprises a mutation.
92. The oligonucleotide of embodiment 91, wherein the mutation is the G380R mutation.
93. A conjugate comprising the oligonucleotide of embodiment 82 and at least one non-nucleotide moiety covalently attached to said oligonucleotide.
94. A pharmaceutical composition comprising the oligonucleotide of embodiment 82 and a pharmaceutically acceptable diluent, carrier, solvent, salt or adjuvant.

95. The use of the oligonucleotide of embodiment 82 for the treatment of achondroplasia.

96. A method of treating a subject affected by cancer, such as bladder cancer achondroplasia, the method comprising the step of administering the oligonucleotide of embodiment 82 to the subject, such that one or more objective symptoms of the achondroplasia are improved.

97. The method of embodiment 96, wherein the objective symptoms are selected from the group consisting of increased muscle tone, lengthening of the arms, lengthening of the legs and increased height.

98. A method of reducing the aberrant expression of FGFR3 in a cell expressing aberrantly expressing FGFR3, the method comprising contacting the cell with the oligonucleotide of embodiment 82, such that the expression of FGFR3 is reduced.

99. The method of embodiment 98, wherein the FGFR3 comprises the G380R mutation.

100. A method of treating a mammal suffering from cancer, such as bladder cancer achondroplasia, the method comprising administering to the mammal a therapeutically effective amount of an oligonucleotide targeted to FGFR3, wherein the oligonucleotide comprises one or more LNA units.

101. The method of embodiment 100, wherein the oligonucleotide comprises a sequence selected from the group consisting of SEQ ID NO: 9, SEQ ID NO: 10, SEQ ID NO: 11, SEQ ID NO: 12, SEQ ID NO: 13, SEQ ID NO: 14, SEQ ID NO: 21, SEQ ID NO: 22, SEQ ID NO: 23, SEQ ID NO: 24 and SEQ ID NO: 25.

102. The method of embodiment 100, wherein the oligonucleotide is administered parenterally.

103. The method of embodiment 100, wherein the oligonucleotide is administered intravenously.

104. The method of embodiment 100 wherein the oligonucleotide is administered by bolus injection into a target organ or tissue.

105. The method of embodiment 100, wherein the oligonucleotide is administered intraperitoneally.

106. An oligonucleotide comprising SEQ ID NO: 21, wherein said oligonucleotide modulates the expression of FGFR3.

107. The oligonucleotide of embodiment 106, wherein said oligonucleotide hybridizes to nucleic acids encoding FGFR3 to form a duplexed structure having a $T_m$ of dissociation of at least about 60° C.

108. The oligonucleotide of embodiment 106, wherein said FGFR3 comprises the G380R mutation, and wherein said modulating the expression of FGFR3 comprises inhibiting the expression of FGFR3.

109. The oligonucleotide of embodiment 108, wherein said oligonucleotide inhibits said expression of FGFR3 at an $IC_{50}$ concentration of between about 0.05 to about 0.75 nM.

110. The oligonucleotide of embodiment 106, wherein said oligonucleotide is stable in plasma at 37° C. for at least about 96 hours.

111. An oligonucleotide comprising SEQ ID NO: 22, wherein said oligonucleotide modulates expression of FGFR3.

112. The oligonucleotide of embodiment 111, wherein said oligonucleotide hybridizes to nucleic acids encoding FGFR3 to form a duplexed structure having a $T_m$ of dissociation of at least about 70° C.

113. The oligonucleotide of embodiment 111, wherein said FGFR3 comprises the G380R mutation, and wherein said modulating the expression of FGFR3 comprises inhibiting the expression of FGFR3.

114. The oligonucleotide of embodiment 113, wherein said oligonucleotide inhibits said expression of FGFR3 at an $IC_{50}$ concentration of between about 0.05 to about 0.75 nM.

115. The oligonucleotide of embodiment 111, wherein said oligonucleotide is stable in plasma at 37° C. for at least about 96 hours.

116. An oligonucleotide comprising SEQ ID NO: 23, wherein said oligonucleotide modulates expression of FGFR3.

117. The oligonucleotide of embodiment 116, wherein said oligonucleotide hybridizes to nucleic acids encoding FGFR3 to form a duplexed structure having a $T_m$ of dissociation of at least about 70° C.

118. The oligonucleotide of embodiment 116, wherein said FGFR3 comprises the G380R mutation, and wherein said modulating the expression of FGFR3 comprises inhibiting the expression of FGFR3.

119. The oligonucleotide of embodiment 118, wherein said oligonucleotide inhibits said expression of FGFR3 at an $IC_{50}$ concentration of between about 0.05 to about 0.75 nM.

120. The oligonucleotide of embodiment 116, wherein said oligonucleotide is stable in plasma at 37° C. for at least about 96 hours.

121. An oligonucleotide comprising SEQ ID NO: 24, wherein said oligonucleotide modulates expression of FGFR3.

122. The oligonucleotide of embodiment 121, wherein said oligonucleotide hybridizes to nucleic acids encoding FGFR3 to form a duplexed structure having a $T_m$ of dissociation of at least about 70° C.

123. The oligonucleotide of embodiment 121, wherein said FGFR3 comprises the G380R mutation, and wherein said modulating the expression of FGFR3 comprises inhibiting the expression of FGFR3.

124. The oligonucleotide of embodiment 123, wherein said oligonucleotide inhibits said expression of FGFR3 at an $IC_{50}$ concentration of between about 0.05 to about 0.75 nM.

125. The oligonucleotide of embodiment 121, wherein said oligonucleotide is stable in plasma at 37° C. for at least about 96 hours.

126. An oligonucleotide comprising SEQ ID NO: 25, wherein said oligonucleotide modulates expression of FGFR3.

127. The oligonucleotide of embodiment 126, wherein said oligonucleotide hybridizes to nucleic acids encoding FGFR3 to form a duplexed structure having a $T_m$ of dissociation of at least about 70° C.

128. The oligonucleotide of embodiment 127, wherein said FGFR3 comprises the G380R mutation, and wherein said modulating the expression of FGFR3 comprises inhibiting the expression of FGFR3.

129. The oligonucleotides of embodiment 128, wherein said oligonucleotide inhibits said expression of FGFR3 at an $IC_{50}$ concentration of between about 0.05 to about 0.75 nM.

130. The oligonucleotide of embodiment 126, wherein said oligonucleotide is stable in plasma at 37° C. for at least about 96 hours.

131. An oligonucleotide that hybridizes to a nucleic acid comprising SEQ ID NO: 20, wherein said oligonucleotide modulates expression of FGFR3.

132. The oligonucleotide of embodiment 131, wherein said oligonucleotide comprises SEQ ID NO: 14.

133. An oligonucleotide comprising SEQ ID NO: 14, wherein said oligonucleotide modulates expression of FGFR3.

134. The oligonucleotide of embodiment 133, wherein said oligonucleotide comprises at least one nucleotide analogue and wherein said nucleotide analogue is a locked nucleic acid.

135. An oligonucleotide comprising SEQ ID NO: 14, wherein said oligonucleotide modulates expression of FGFR3, and wherein said oligonucleotide comprises at least one nucleotide analogue at one or more positions selected from the group consisting of:
(a) the guanine nucleotide at position 1 is an oxy-LNA;
(b) the adenine nucleotide at one or more of positions 2 and 3 is an oxy-LNA;
(c) the cytosine nucleotide at one or more of positions 10 and 11 is an oxy-LNA; and
(d) the thymine nucleotide at position 12 is an oxy-LNA.

136. The oligonucleotide of embodiment 135, wherein said cytosine nucleotide at position 11 is a C5-methylcytosine, wherein said C5-methylcytosine is a β-D-oxy-LNA, wherein said thymine nucleotide at position 12 is a β-D-oxy-LNA, and wherein all internucleotide linkage groups are phosphorothioate internucleotide linkage groups.

137. The oligonucleotide of embodiment 135, wherein said guanine nucleotide at position 1 is a β-D-oxy-LNA, wherein said adenine nucleotide at positions 2 and 3 are β-D-oxy-LNA, and wherein all internucleotide linkage groups are phosphorothioate internucleotide linkage groups.

138. The oligonucleotide of embodiment 135, wherein said guanine nucleotide at position 1 is a β-D-oxy-LNA, wherein said cytosine nucleotide at positions 10 and 11 are both C5-methylcytosine, wherein said C5-methylcytosine is a β-D-oxy-LNA, wherein said thymine nucleotide at position 12 is β-D-a oxy-LNA, and wherein all internucleotide linkage groups are phosphorothioate internucleotide linkage groups.

139. The oligonucleotide of embodiment 135, wherein said cytosine nucleotide at positions 10 and 11 are both C5-methylcytosine, wherein said C5-methylcytosine is a β-D-oxy-LNA, wherein said thymine nucleotide at position 12 is β-D-a oxy-LNA, and wherein all internucleotide linkage groups are phosphorothioate internucleotide linkage groups.

140. The oligonucleotide of embodiment 135, wherein at least one nucleotide is a modified nucleobase independently selected from the group consisting of 5-methylcytosine, isocytosine, pseudoisocytosine, 5-bromouracil, 5-propynyluracil, 6-aminopurine, 2-aminopurine, inosine, diaminopurine and 2-chloro-6-aminopurine cytosine.

141. The oligonucleotide of embodiment 135, wherein each of said cytosine nucleotides at positions 10 and 11 are modified nucleobases.

142. The oligonucleotide of embodiment 141, wherein said modified nucleobases are C5-methylcytosine.

143. The oligonucleotide of embodiment 135, wherein said oxy-LNA is a β-D-oxy LNA.

144. The oligonucleotide of embodiment 135, wherein at least one internucleotide linkage group is a phosphorothioate internucleotide linkage group.

145. The oligonucleotide of embodiment 135, wherein all internucleotide linkage groups are phosphorothioate internucleotide linkage groups.

EXAMPLES

The following examples describe several oligonucleotides targeting the mutant FGFR3 G380R mRNA transcript, as well as various superior properties of these oligonucleotides. In particular, Example 1 demonstrates the efficacy of 21 oligonucleotides to knock-down mutant G380R FGFR3 expression and the selectivity of those 21 oligonucleotides (e.g., inhibition of mutant G380R FGFR3 expression as compared to inhibition of wild-type FGFR3 expression). Example 2 demonstrates the strength of each of ten oligonucleotides to inhibit mutant G380R FGFR3 expression, measured as an $IC_{50}$ value, and the difference in the strength to inhibit mutant G380R FGFR3 expression as compared to wild-type FGFR3 expression. Example 3 describes an investigation into non-specific effects of those ten oligonucleotides by comparing the inhibition effect of each oligonucleotide on two unrelated targets. Example 4 describes the binding energy, measured as melting temperature ($T_m$), between each of those ten oligonucleotides and either the mutant G380R FGFR3 (perfect complement) or wild-type FGFR3 (one complementarity mismatch at mutation site). Example 5 demonstrates the nuclease sensitivity, measured as plasma stability, of those ten oligonucleotides. Example 6 describes an assessment of the in vivo tolerance for selected oligonucleotides in a standard 16-day mouse study.

Example 1

Efficacy and Selectivity Testing for 21 Oligonucleotides

A total of 21 antisense oligonucleotides, each having a locked nucleic acid (LNA) backbone, were designed to selectively target the human FGFR3 G380R mutation and the region surrounding or adjacent to the mutation. In particular, the 21 LNA antisense oligonucleotides were designed to hybridize to a region including an "A" at the 1394 position of the FGFR3 mRNA (i.e., the GGG→AGG missense mutation at position 1394 of NM_000142.3) and nucleotides upstream and/or downstream of the 1394 position, ranging from position 1380 to 1408.

Human cells transiently transfected with vectors containing FLAG-tagged sequences of either the full length FGFR3 having the G380R mutation or the corresponding wild-type FGFR3 were used for initial characterization of the efficacy of each of the 21 oligonucleotides. The human A549 cell line used for the assay was selected because of its relatively low expression of endogenous FGFR3. A qualitative PCR (qPCR) assay was designed to specifically recognize the vector expression products by targeting the FLAG sequence. In addition, a qPCR assay was designed to specifically recognize the endogenous expression product by targeting the 3'UTR of FGFR3, which was not part of the vector expression system.

Figure 1B:
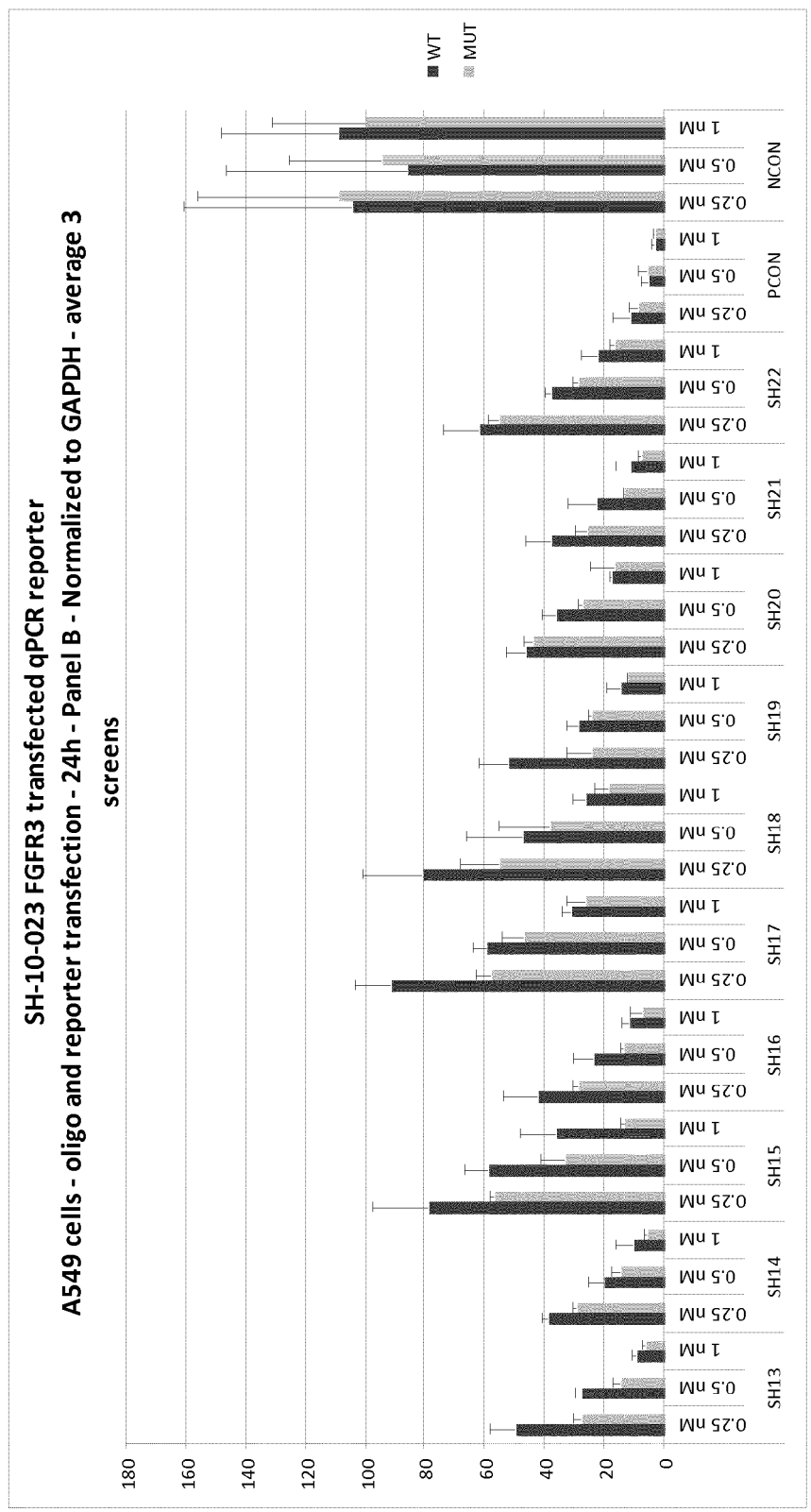

The efficacy and selectivity of each of the 21 oligonucleotides was assessed by co-transfecting human A549 cells with each oligonucleotide and either the wild-type (WT) or mutant (MUT) FLAG-tagged vector construct. The oligonucleotide concentrations were assessed at 0.25 nM, 0.5 nM, and 1.0 nM. Cells were harvested 24 hours after transfection, and the level of the expressed FLAG-tag reporter was determined with the reporter-specific qPCR assay. Results, which were normalized to the endogenous GAPDH levels, are shown in FIGS. 1A and 1B as a percent of the mock-treated samples. The 21 oligonucleotides are identified with identifiers, each starting with "SH," while the oligonucleotide designated as PCON represents a positive control which targets both wild-type and mutant FGFR3 transcripts at a region distinct from the 1394 mutation site. The mock-treated samples were transfected with the FLAG-tagged reporter construct described above in the absence of a test oligonucleotide, which was replaced with water. In addition, a random scrambled oligonucleotide designated as NCON was used as a negative control.

As illustrated in FIGS. 1A and 1B, certain oligonucleotides diminished the wild-type FGFR3 and/or mutant FGFR3 expression by 80% or less, 60% or less, 50% or less, 40% or less, 30% or less, 25% or less, 20% or less, and even 10% or less as compared to the FGFR3 expression of the mock samples, depending on the concentration (0.25 nM, 0.5 nM, or 1 nM) of the oligonucleotide. Moreover, certain oligonucleotides substantially and preferentially reduced expression (i.e., down-regulated expression) of the mutant FGFR3 as compared to the wild-type FGFR3 expression. For example, the oligonucleotide designated as SH13 (SEQ ID NO: 22) at a concentration of 0.25 nM diminished the mutant FGFR3 level to nearly half of the corresponding wild-type FGFR3 level. The positive control, designated as PCON, demonstrated substantial inhibition of both mutant and wild-type FGFR3 levels, showing little to no specificity because it is not directed to the mutation site.

The 21 oligonucleotides were also tested for efficacy and selectivity using gymnosis (i.e., unassisted uptake) as a means of introducing the oligonucleotides into the A549 cells. Specifically, the oligonucleotides were delivered by gymnosis for 48 hours, after which the A549 cells were washed thoroughly to eliminate any oligonucleotide still adhering to the surface of the cell or otherwise remaining in the culture vessel. The mutant or wild-type construct was then delivered by standard transfection, and the A549 cells were harvested and assayed by qPCR 24 hours later.

Figure 2A:
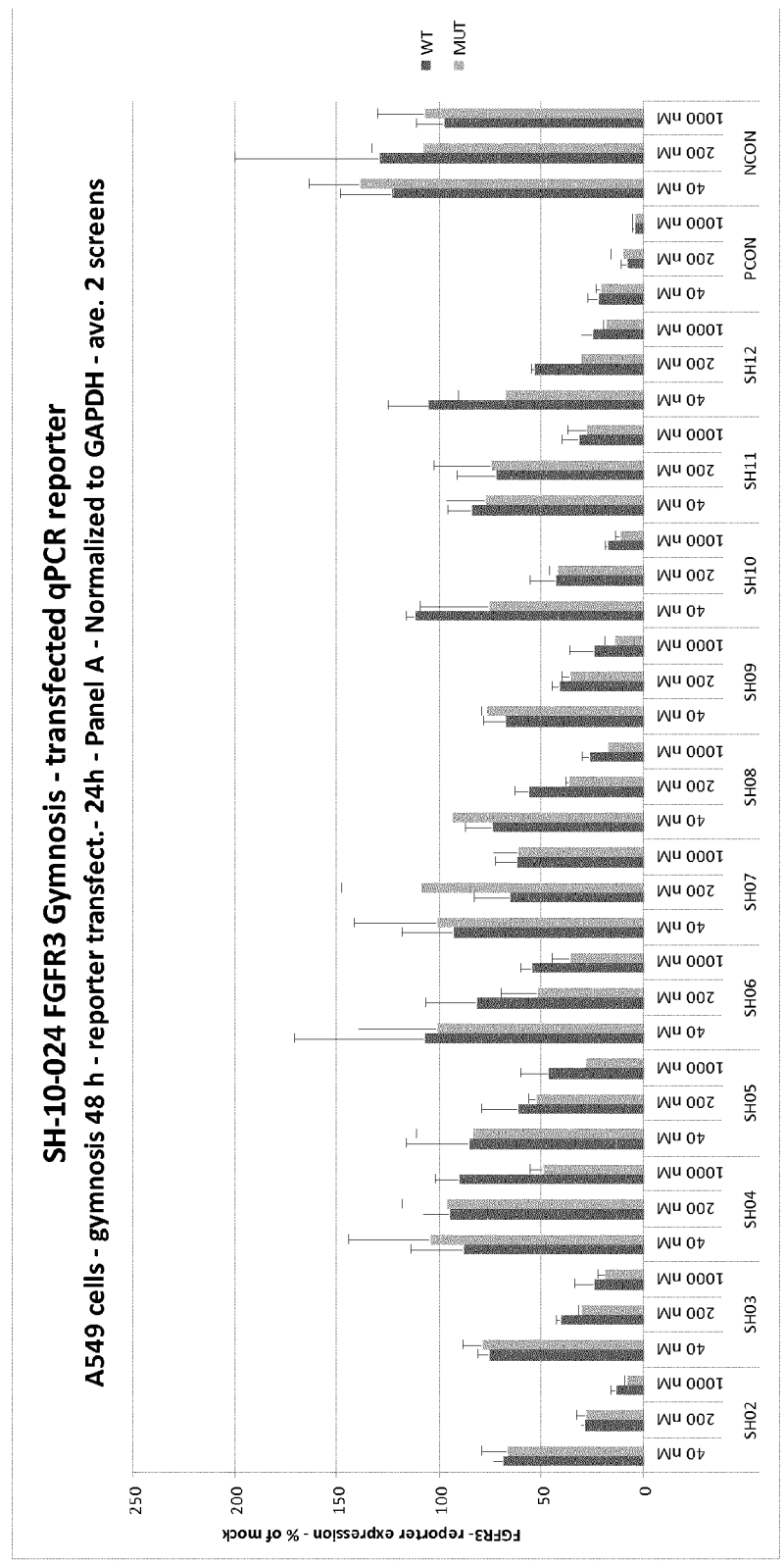
FIGS. 2A and 2B illustrate flag-tagged wild-type (WT) and mutant (MUT) reporter construct levels in human A549 cells having undergone 48 hours of gymnotic treatment with oligonucleotides complementary to portions of the region including and surrounding the nucleotides encoding the FGFR3 G380R mutation. The human A549 cells were transfected with either the WT or MUT reporter construct following gymnotic treatment with the oligonucleotide. The cells were then harvested 24 hours after transfection, and the level of the flag-tagged reporter transcript was determined with a reporter-specific quantitative PCR assay. The results are reported as a percentage of the mock-treated samples and are reported as the average of three independent studies per oligonucleotide. The depicted error bars indicate the standard deviation. As illustrated in both FIGS. 2A and 2B the 21 oligonucleotides demonstrated a robust knock-down of the MUT reporter construct with a marked dose response relative to the WT reporter.
Figure 2B:
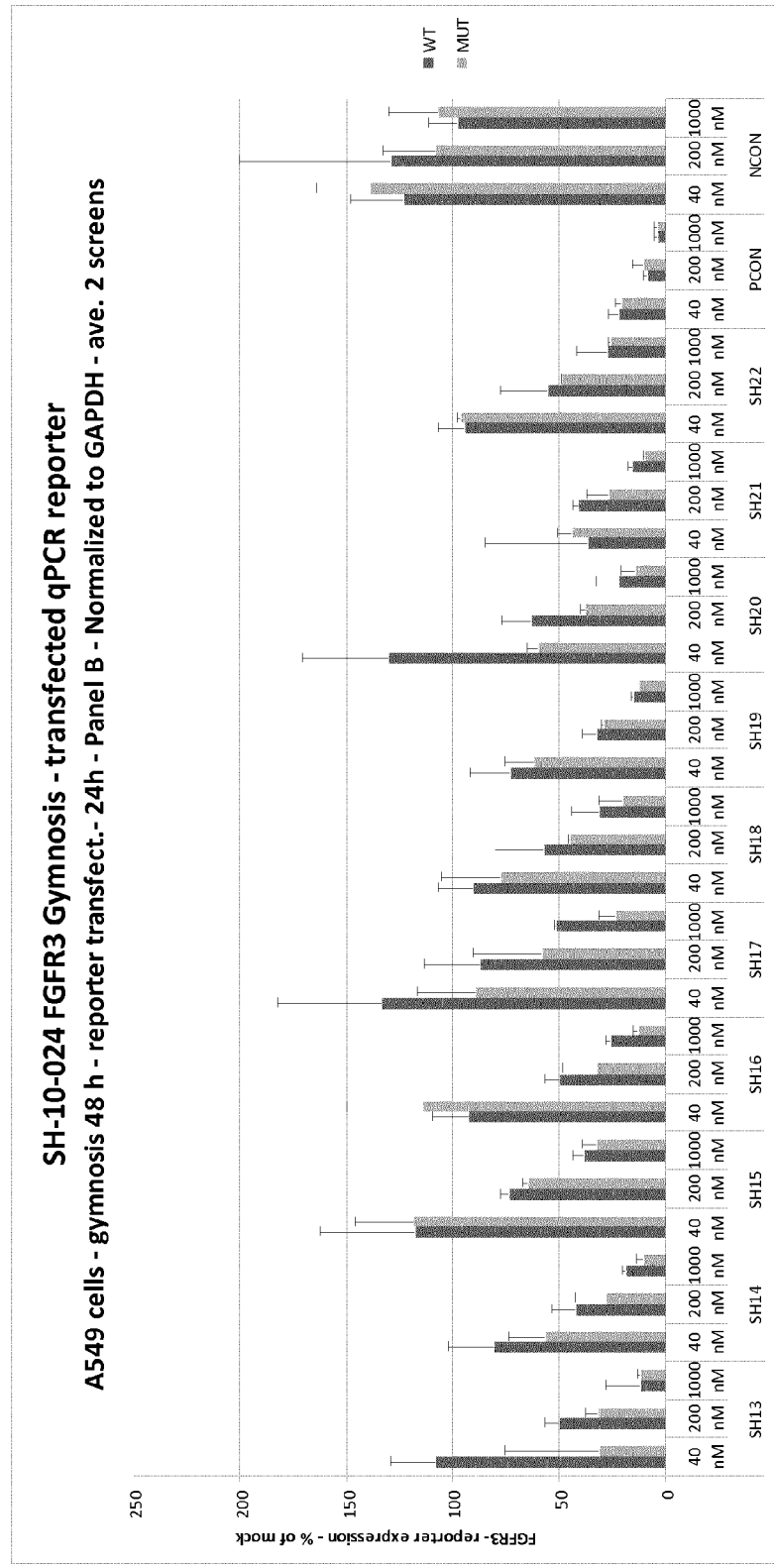

As with the transfection data presented in FIGS. 1A and 1B, a robust knock-down with marked dose response was seen for most of the oligonucleotides tested, as illustrated in FIGS. 2A and 2B, and a clear ranking could be established. In fact, there was a significant correspondence between the rank order of the oligonucleotides in both transfection and gymnosis studies. However, the discrimination between the mutant and the wild-type reporter was less noticeable in the gymnosis studies relative to the transfection studies. No significant discrepancies were seen in ranking between the data collected in the transfection experiments and the gymnosis experiment described herein.

The transfection and gymnosis data illustrated that each of the 21 oligonucleotides showed efficacy and selectively at one or more concentrations. From that collective data, which was used to determine the specificity and/or potency of the 21 oligonucleotides evaluated, ten oligonucleotides were identified for additional characterization.

To confirm the ability of the ten selected oligonucleotides to knock-down FGFR3 expression, a co-transfection experiment similar to that described above in human A549 cells was performed in HeLa cells. Specifically, for each of the ten oligonucleotides, HeLa cells were co-transfected with the oligonucleotide and either the wild-type (WT) or mutant (MUT) reporter construct. The initial screening concentrations evaluated were 0.2 nM, 1.0 nM and 5.0 nM. Cells were harvested 24 hours after transfection, and the level of the transcript was determined with a reporter-specific qPCR assay. Results were normalized to the endogenous GAPDH levels and expressed as percent of the mock-treated samples.

Figure 3:
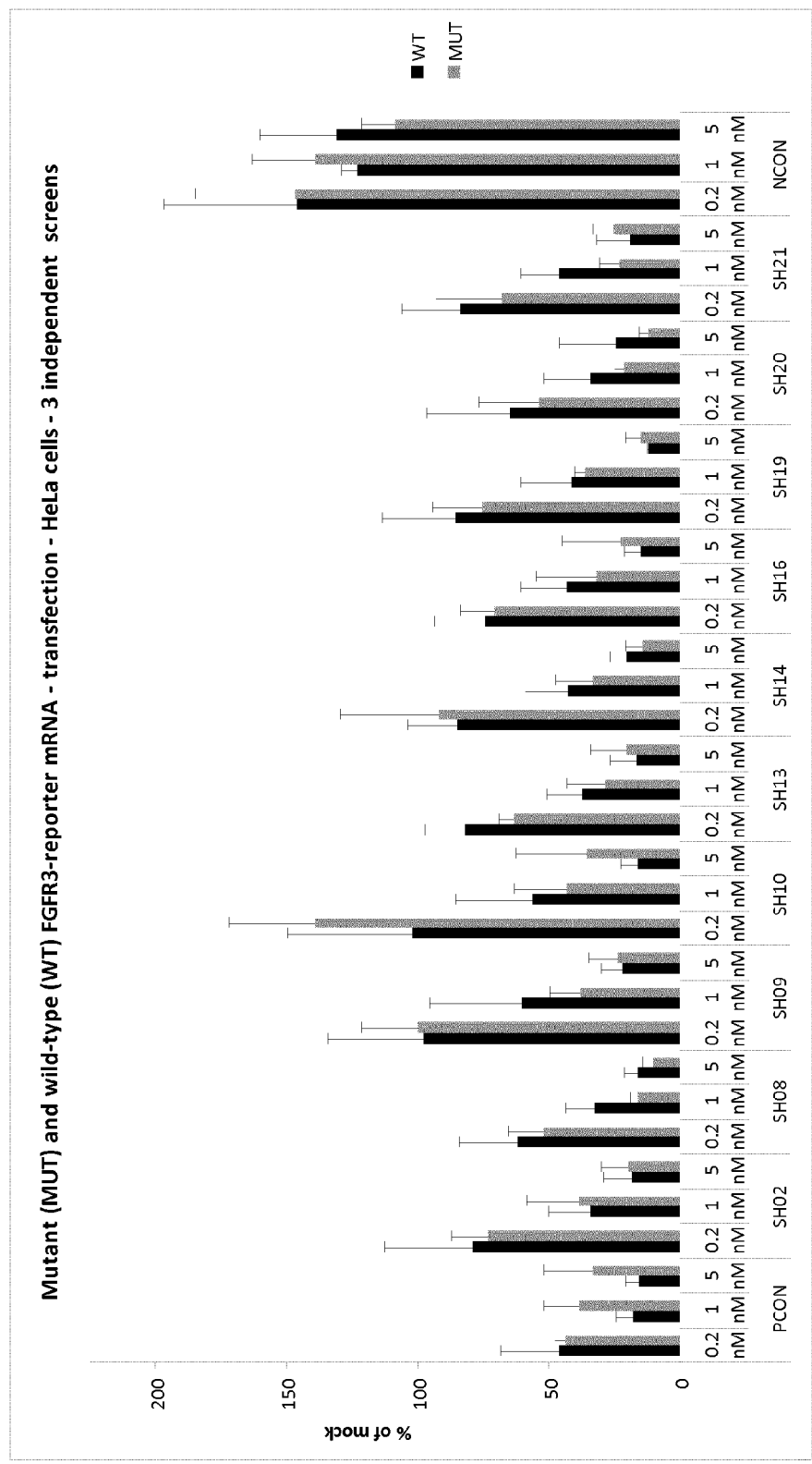
FIG. 3 illustrates flag-tagged wild-type (WT) and mutant (MUT) reporter levels in HeLa cells transfected with each of ten oligonucleotides complementary to different portions of the region including and surrounding the FGFR3 G380 mutation. The oligonucleotides were evaluated at initial screening concentrations of 0.2 nM, 1.0 nM and 5.0 nM. The HeLa cells were co-transfected with an oligonucleotide and either the WT or MUT reporter construct. The cells were then harvested 24 hours after transfection, and the level of the reporter construct was determined with a reporter-specific quantitative PCR assay. The results are reported as the average of three independent studies per oligonucleotide and the error bars indicate the standard deviation.

As illustrated in FIG. 3, all ten oligonucleotides demonstrated a dose-dependent knock-down at the concentrations evaluated. The effect of the oligonucleotides was similar to that observed in the A549 cells, although slight differences were evident. These differences included the observation that the positive control (designated PCON) which had been significantly more efficient against the reporter target in the A549 cells, had efficiency similar to that of the mutation-specific oligonucleotides in HeLa cells. A second, minor difference was the observation that the previously best-performing oligonucleotide (designated SH02 and corresponding to SEQ ID NO: 21) did not perform appreciably better than the remaining selections in the HeLa cells. However, these minor observations did not alter the overall conclusion of the instant studies and confirmed that the oligonucleotides tested were effective and demonstrated selectivity between the mutant and wild-type reporter constructs in both HeLa cells and in A549 cells.

Example 2

$IC_{50}$ Testing for Ten Oligonucleotides

The ten oligonucleotides selected as a result of the studies described in Example 1 were further assessed for their inhibition strength by assessing the $IC_{50}$ value for each oligonucleotide. In particular, transfected oligonucleotides were further divided into those having an $IC_{50}$ value lower than 5 nM and those having an $IC_{50}$ value greater than 5 nM. A second characterization criterion for each oligonucleotide was whether it showed more or less than a three-fold difference between the $IC_{50}$ values for the mutant reporter relative to the wild-type reporter.

Figure 4:
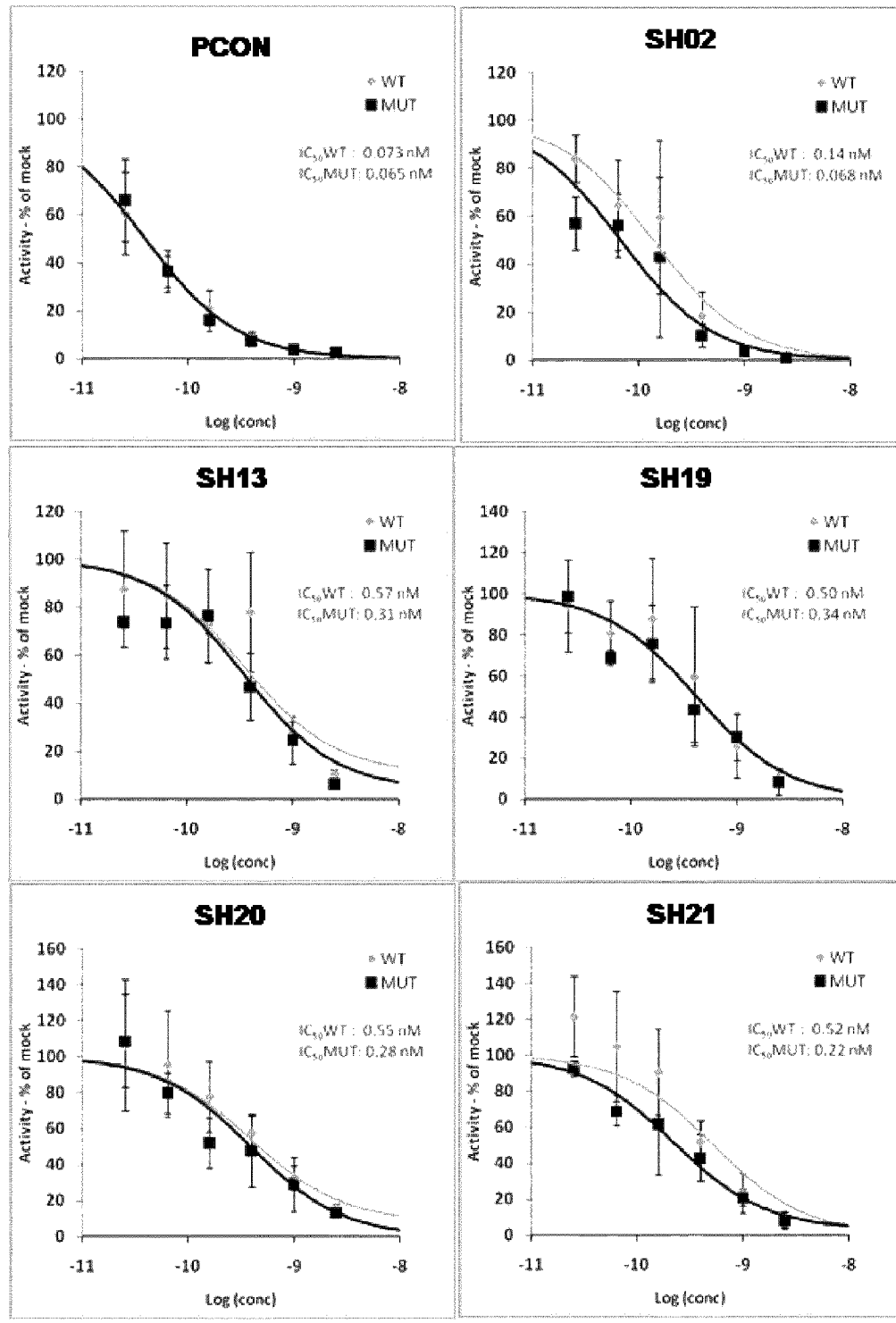
FIG. 4 illustrates the half maximal inhibitory concentration ($IC_{50}$) curves for selected oligonucleotides designed to be complementary to portions of the region including and surrounding the nucleotides encoding the FGFR3 G380 mutation. Either the flag-tagged wild-type (WT) or mutant (MUT) reporter construct and one of ten oligonucleotides were co-transfected in human A549 cells. The cells were then harvested and RNA extracted for reporter-specific quantitative PCR 24 hours following transfection. The plotted data points represent the average reporter signal of three independent experiments and the error bars represent the standard deviation. The grey curve represents the fitted response curve of the WT reporter and the black curve represents the fitted response curve of the MUT reporter. The corresponding $IC_{50}$ value for each curve is indicated on each graph and also in Table 2.

To establish an $IC_{50}$ value for each of the ten oligonucleotides, each oligonucleotide was co-transfected in A549 cells with either the wild-type (WT) or mutant (MUT) reporter constructs. The oligonucleotides were transfected at 2.5 nM, 1 nM, 0.4 nM, 0.16 nM, 0.064 nM, and 0.0256 nM concentrations. Cells were harvested and RNA extracted for qPCR after 24 hours. The studies were repeated three times and the values were plotted in Graphpad Prism against a sigmoidal response curve using non-linear regression. From the regression, an estimate of the $IC_{50}$ value in the reporter assay was determined. The regression curves are presented in FIG. 4, and the corresponding $IC_{50}$ values are tabulated in Table 2 below.

TABLE 2

| Oligo | | IC50 |
|---|---|---|
| PCON | WT | 0.038 |
|  | MUT | 0.040 |
| SH02 | WT | 0.14 |
|  | MUT | 0.068 |
| SH13 | WT | 0.57 |
|  | MUT | 0.31 |
| SH19 | WT | 0.50 |
|  | MUT | 0.34 |
| SH20 | WT | 0.55 |
|  | MUT | 0.28 |
| SH21 | WT | 0.52 |
|  | MUT | 0.22 |
| NCON | WT |  |
|  | MUT |  |

As shown in Table 2, the $IC_{50}$ values for five selected oligonucleotides against the (perfectly complementary) mutant G380R FGFR3 target fell below 5 nM, and even under 0.5 nM. The selected oligonucleotide that demonstrated an $IC_{50}$ better than 0.2 nM was the nucleotide designated SH02 (SEQ ID NO: 21), which demonstrated $IC_{50}$ value of 0.068 nM. The positive control, designated PCON, which targets both reporter transcripts at a site separate from the mutation site, demonstrated an $IC_{50}$ of approximately 0.04 nM for both the mutant and the wild-type reporter constructs. With regard to the selectively of the selected oligonucleotides for the mutant G380R FGFR3 reporter as compared to the wild-type FGFR3 reporter, no oligonucleotide demonstrated a better than approximately 2.5 fold selectivity of the mutant over the wild-type reporter.

Example 3

Target Specificity for Ten Oligonucleotides

The ten oligonucleotides described in Example 2 were further assessed for their ability to non-specifically knock-down non-targeted transcripts at a concentration of 25 nM. One of each of the ten oligonucleotides was delivered to the same A549 cells by transfection. The cells were harvested and tested by qPCR for knock-down of endogenous SCA3 mRNA (FIG. 5A) or PTEN mRNA (FIG. 5B). The results presented were normalized to the endogenous GAPDH levels and expressed as a percent of the mock treated samples.

Figure 5A:
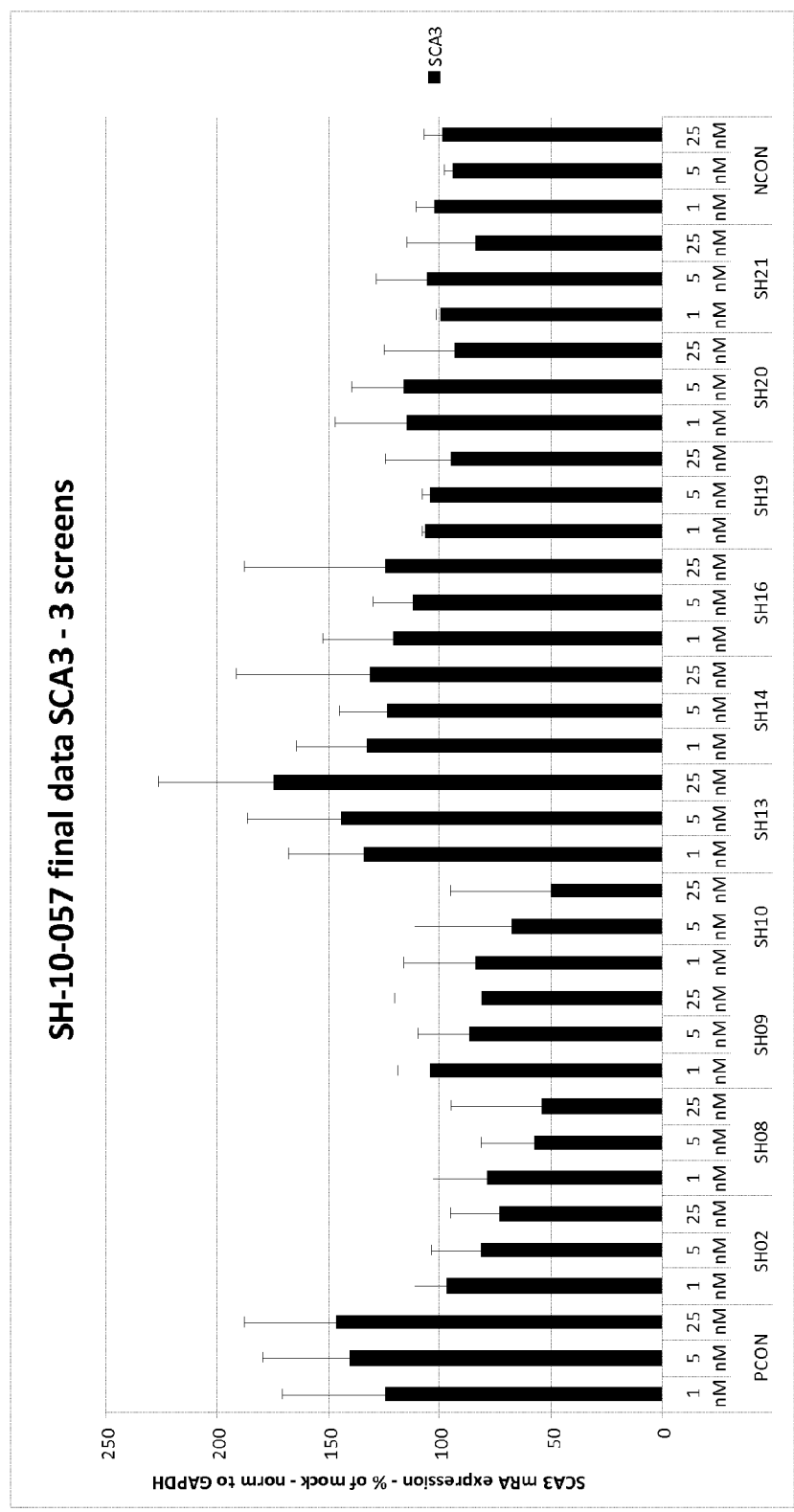
FIGS. 5A and 5B illustrate the specificity of each of ten oligonucleotides complementary to portions of the region including and surrounding the nucleotides encoding the FGFR3 G380 mutation toward unrelated SCA3 and PTEN targets, respectively. Each of the ten oligonucleotides was delivered to human A549 cells by transfection. The human A549 cells were then harvested and tested by quantitative PCR for knock-down of either the SCA3 or PTEN mRNA. The results are presented as the average of three independent studies per pre-lead oligonucleotide. The error bars represent standard deviation of the three studies per oligonucleotide.
Figure 5B:
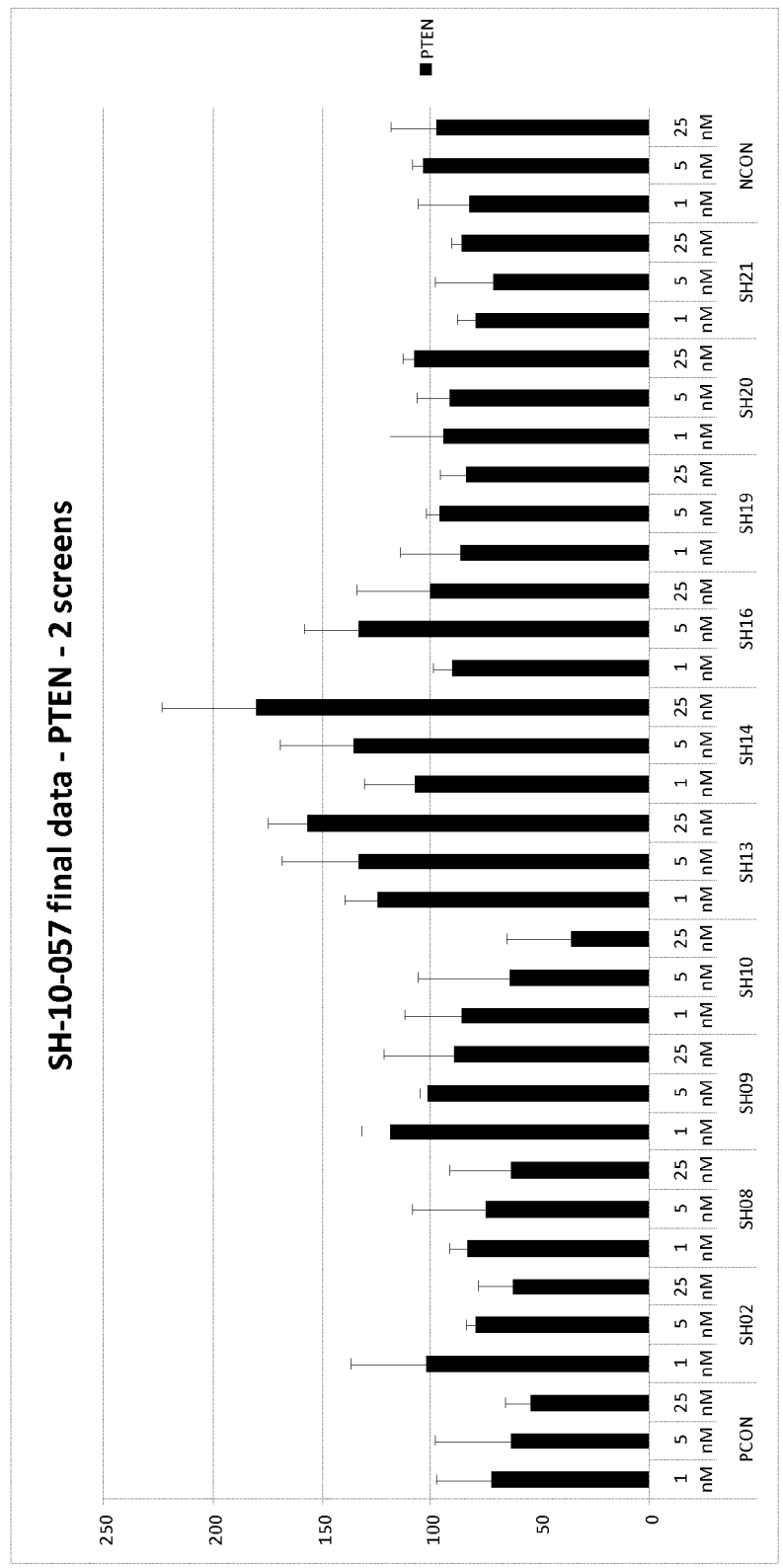

As illustrated by FIGS. 5A and 5B, the results of the instant studies demonstrated a slight knock-down of both the SCA3 and PTEN transcripts by some of the oligonucleotides, though significantly less than the knock-down of the FGFR3 wild-type or mutant transcripts described in Example 1 above. Accordingly, the effect of each of the ten oligonucleotides on non-specific targets was significantly lower than the effect on the specific FGFR3 target.

Example 4

Melting Temperature for Ten Oligonucleotides Annealed to Wild-Type or Mutant FGFR3

As part of the characterization of the oligonucleotide candidates described in Examples 2 and 3 above, the melting temperature ($T_m$) of each oligonucleotide from a complementary mutant target RNA (designated cMUT) was evaluated. Each of the ten oligonucleotides was also tested against an RNA representing the wild-type allele (designated cWT), which included a single complementarity mismatch against each oligonucleotide at the G380R mutation site.

The $T_m$ values for each of the ten oligonucleotides was determined twice, and the change in $T_m$ ($\Delta T_m$) represents the average of the melting and annealing temperature for each oligonucleotide. The $T_m$ data representing five selected oligonucleotide candidates is presented in Table 3, where the $\Delta T_m$ was defined as the difference between the cMUT (perfect complement) and cWT (one complementary mismatch at mutation site) values.

TABLE 3

| Oligo | RNA cMUT $T_m$ (° C.) | RNA cWT $T_m$ (° C.) | $\Delta T_m$ (MUT − WT) (° C.) |
| --- | --- | --- | --- |
| SH02 | 66.9 | 62.1 | 4.8 |
| SH13 | 75.8 | 71.4 | 4.4 |
| SH19 | 72.0 | 71.0 | 1.0 |
| SH20 | 72.6 | 73.5 | −0.9 |
| SH21 | 71.2 | 72.3 | −1.1 |

When targeting the ten oligonucleotides against the WT allele of FGFR3, the single mismatch is a G-T mismatch. This particular mismatch is not particularly discriminatory in terms of binding energy, a fact that is clearly apparent from the $\Delta T_m$. The $\Delta T_m$ ranged from a high of 4.8° C. to a low of negative −1.1° C.; the latter indicating that two of the oligonucleotides anneal better to the single-mismatch RNA than to the perfectly complementary RNA. These observations correspond with the relatively low degree of discrimination seen from the $IC_{50}$ values of some of the ten oligonucleotides between the wild-type reporter and the mutant reporter, as described in Example 2 above.

Example 5

Plasma Stability for Each of Ten Oligonucleotides

As part of the characterization of the ten oligonucleotides described in Examples 2, 3 and 4, the nuclease sensitivity of each of the ten oligonucleotides was assessed. Specifically, each of the ten oligonucleotides was incubated in mouse plasma for 96 hours at 37° C., and samples were taken every 24 hours and analyzed. The samples were evaluated by gel electrophoresis for the loss of full length oligonucleotide and the emergence of degradation products. The samples were compared to an unstable control oligonucleotide (designated Con).

Figure 6:
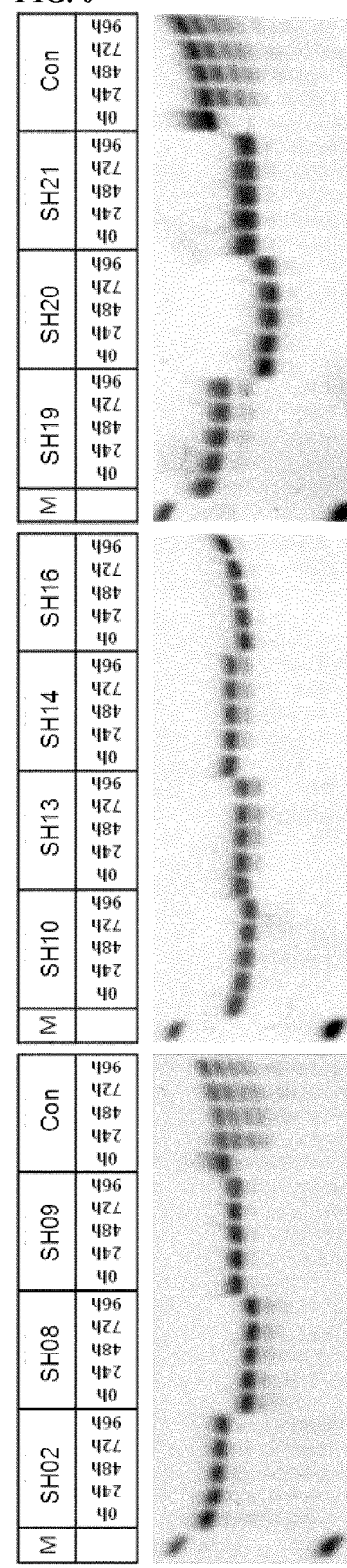
FIG. 6 illustrates the plasma stability of each of ten oligonucleotides complementary to portions of the region including and surrounding nucleotides encoding the FGFR3 G380 mutation. Each of the ten oligonucleotides was incubated for up to 96 hours in mouse plasma at 37° C. Samples were taken every 24 hours and analyzed by PAGE. The plasma stability of each of the ten oligonucleotides was found to be well within the expected ranges, and in particular all of the ten oligonucleotides were found to have an overall half-life greater than 96 hours.

The plasma stability of all of the oligonucleotides was found to be within the expected ranges. As illustrated in FIG. 6, all ten of the oligonucleotides were found to have an overall half-life of greater than 96 hours.

Example 6

In Vivo Tolerance Study for Each of Ten Oligonucleotides

The in vivo tolerance of each of the ten oligonucleotides was tested in a standard 16-day mouse study. Each of the ten oligonucleotides was tested for in vivo tolerance in female NMRI mice, primarily to assess any undesired effects on the liver. The subject animals were dosed at 15 mg/kg intravenously every 3 days until day 14, and then sacrificed at day 16. Serum was sampled and analyzed for alanine aminotransferase (ALT) and aspartate aminotransferase (AST) concentrations.

Figure 7:
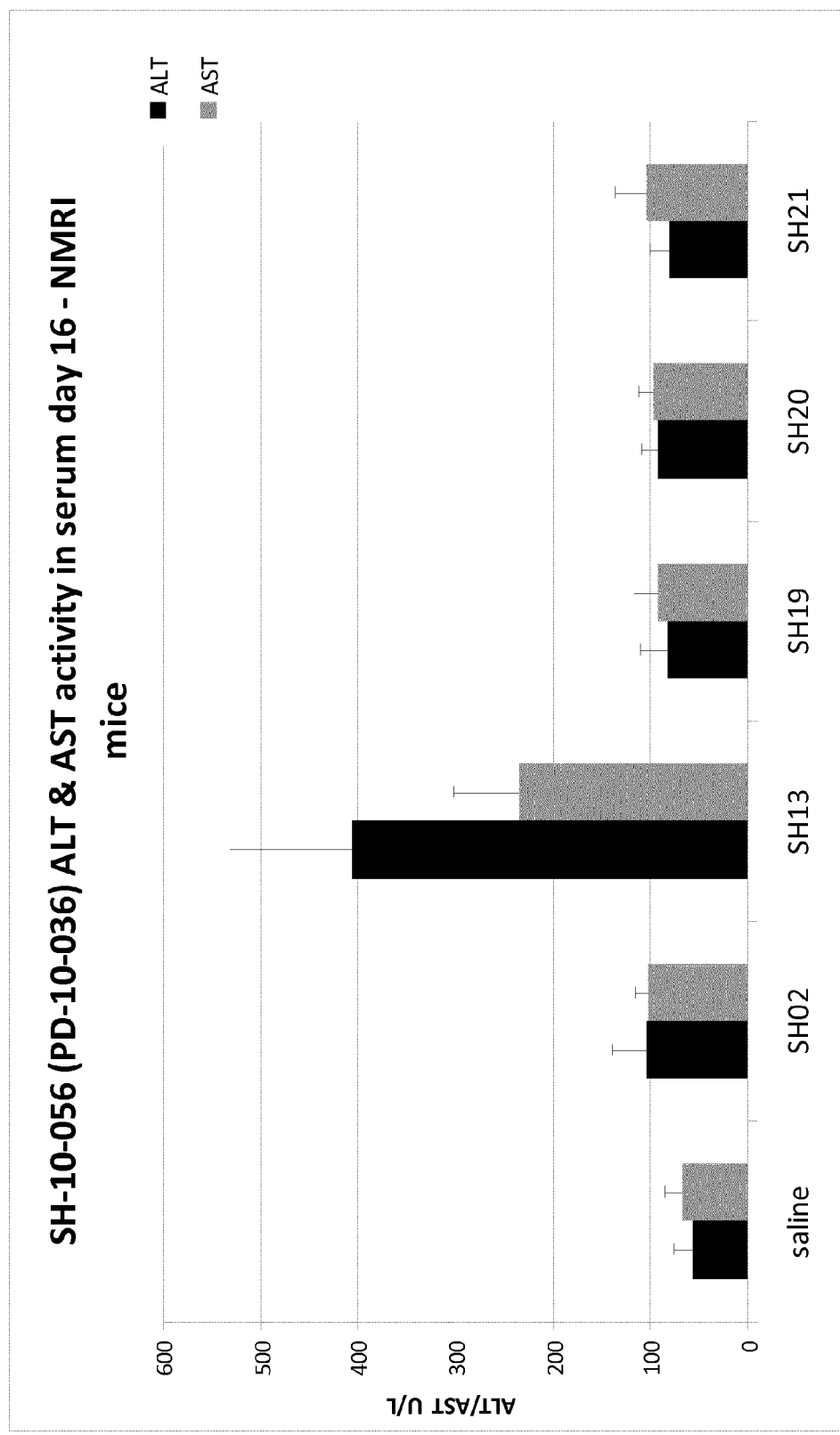
FIG. 7 illustrates the results of a 16-day in vivo tolerance study in which oligonucleotides complementary to portions of the region including and surrounding the nucleotides encoding the FGFR3 G380 mutation were administered to mice every 3 days until day 14. The mice were sacrificed and evaluated at day 16. Controls included mice administered a saline control. The five selected oligonucleotides (SH02, SH13, SH19, SH20 and SH21 which correspond to SEQ ID NOS: 21, 22, 23, 24 and 25, respectively) resulted in acceptable elevations of the liver enzymes alanine aminotranferease (ALT) and aspartate aminotransferase (AST).

As depicted in FIG. 7 oligonucleotide SH13 (SEQ ID NO: 22) demonstrated an intermediate, but acceptable elevation in the levels of liver enzymes, and the oligonucleotides designated SH02 (SEQ ID NO: 21), SH19 (SEQ ID NO: 23), SH20 (SEQ ID NO: 24), and SH21 (SEQ ID NO: 25) demonstrated a negligible elevation in the levels of liver enzymes.

Based on the characteristics identified in Examples 1-6, five oligonucleotides (namely the oligonucleotides designated SH02, SH13, SH19, SH20, and SH21) were shown to have superior properties for use in administration to a subject to diminish the expression of (mutant) G380R FGFR3. As described above, the selected oligonucleotides were selected as being superior compared with a population of unselected oligonucleotides. The sequences of these five oligonucleotides are set forth in Table 4 below, where β-D-oxy LNA are illustrated in bold capital letters with the superscript "o" the right, lowercase letters indicate deoxyriboses, and 's' and 'm' correspond to phosphorothioate and C5-methylcytosine, respectively.

TABLE 4

| Identifier | SEQ ID NO: | FGFR3 Target Nucleotide Position | Length | OLIGONUCLEOTIDE SEQUENCE | mRNA Target Sequence |
|---|---|---|---|---|---|
| SH02 | 21 | 1380-1395 | 16 | 5'- $C_s^m T_s^o G_s^o G_s^o t_s a_s g_s c_s t_s g_s a_s g_s a_s T_s^o G_s^o C_s^{mo}$ -3' | 5'-GCAUCCUCAGCUACAG-3' (SEQ ID NO: 15) |
| SH13 | 22 | 1391-1405 | 15 | 5'- $G_s^o A_s^o A_s^o g_s c_s c_s a_s c_s c_s t_s G_s^o T_s^o A^o$ 3' | 5'-UACAGGGUGGGCUUC-3' (SEQ ID NO: 16) |
| SH19 | 23 | 1393-1408 | 16 | 5'- $G_s^o A_s^o A_s^o g_s a_s g_s c_s c_s c_s a_s c_s c_s- C_s^m T_s^o G^o$ 3' | 5'-CAGGGUGGGCUUCUUC-3' (SEQ ID NO: 17) |
| SH20 | 24 | 1394-1407 | 14 | 5'- $A_s^o A_s^o G_s^o a_s a_s g_s c_s c_s c_s a_s c_s- C_s^m C_s^{mo} T^o$ 3' | 5'-AGGGUGGGUUCUU-3' (SEQ ID NO: 18) |
| SH21 | 25 | 1394-1408 | 15 | 5'- $G_s^o A_s^o A_s^o g_s a_s g_s c_s c_s c_s a_s c_s- C_s^m C_s^{mo} T^o$ 3' | 5'-AGGGUGGGCUUCUUC-3' (SEQ ID NO: 19) |

Example 7

Demonstration of Therapeutic Benefit of Oligonucleotides in Mouse Model of Achondroplasia The ability of the oligonucleotides designated as SH02, SH13, SH19, SH20, and SH21 (corresponding to SEQ ID NOS: 21, 22, 23, 24 and 25, respectively) to reduce disease pathology relating to the expression of G380R-mutated FGFR3 is determined as follows. An animal model is selected from several known animal models of achondroplasia. The preferred mouse model correlates with the human mutation FGFR3-G380R. FGFR3-G380R is a naturally occurring mutation found in approximately 97% of human achondroplasia patients, and in mice results in a phenotype that mimics human achondroplasia. Primary endpoints for the in-life efficacy can include, for example, growth rate, normalization of long bone proportions, and histopathological assessment of the hyperproliferative region of the epiphyseal growth plates. Disease phenotype, and reversal thereof by each oligonucleotide, can be verified by various methodologies known in the art, for example, by histological examination of the epiphyseal growth plates.

Parameters to be investigated can include, among other things, an increase in femur length in oligonucleotide-treated G380R mice that is statistically longer than in oligonucleotide-untreated G380R mice and/or an increase in thickness of hyperproliferative zone in oligonucleotide-treated G380R mice that is statistically greater than in oligonucleotide-untreated G380R mice.

The studies described in this Example can provide further characterization of (1) antisense-locked nucleic acid oligonucleotides directed against mutant G380R FGFR3 as an effective treatment of diseases relating to the G380 FGRF3 mutation, (2) oligonucleotides for use in particular achondroplasia disease models and as candidates for pharmacokinetics and toxicology studies and (3) dosing and dose-schedules for clinical administration of the oligonucleotides described herein.

The invention claimed is:

1. An antisense oligonucleotide 8-25 nucleotides in length comprising one or more nucleotide analogues, wherein said oligonucleotide is 100% complementary to a region of SEQ ID NO: 4 which comprises nucleotide position 1394 of SEQ ID NO: 4 and comprises a nucleotide sequence selected from the group consisting of SEQ ID NO: 9, SEQ ID NO: 10, SEQ ID NO: 11, SEQ ID NO: 12, SEQ ID NO: 13 and SEQ ID NO: 14.

2. The oligonucleotide of claim 1, wherein said oligonucleotide is 14-18 nucleotides in length.

3. The oligonucleotide of claim 1, wherein said oligonucleotide is selected from the group consisting of SEQ ID NO: 9, SEQ ID NO: 10, SEQ ID NO: 11, SEQ ID NO: 12, SEQ ID NO: 13, SEQ ID NO: 14, SEQ ID NO: 21, SEQ ID NO: 22, SEQ ID NO: 23, SEQ ID NO: 24 and SEQ ID NO: 25.

4. The oligonucleotide of claim 1, wherein said one or more nucleotide analogues are selected from the group consisting of: Locked Nucleic Acid (LNA) units; 2'-O-alkyl-RNA units, 2'-OMe-RNA units, 2'-amino-DNA units, and 2'-fluoro-DNA units.

5. The oligonucleotide of claim 1, wherein said oligonucleotide comprises two or more LNA monomeric units.

6. The oligonucleotide claim 1, wherein the oligonucleotide is selected from the group consisting of SEQ ID NO: 21, SEQ ID NO: 22, SEQ ID NO: 23, SEQ ID NO: 24 and SEQ ID NO: 25.

7. The oligonucleotide of claim 1 which comprises SEQ ID NO: 21.

8. A conjugate comprising the oligonucleotide according to claim 1 or claim 3 and at least one non-nucleotide moiety covalently attached to said oligonucleotide.

9. A method of reducing the expression of FGFR3 mRNA comprising delivering to said FGFR3 mRNA the oligonucleotide according to claim 1 or claim 3, under conditions appropriate for hybridization of said FGFR3 mRNA with said oligonucleotide, thereby reducing the expression of the FGFR3 mRNA.

10. An in vitro method of reducing the expression of FGFR3 mRNA comprising delivering to said FGFR3 mRNA the oligonucleotide according claim 1 or claim 3, thereby reducing the expression of the FGFR3 mRNA.

11. A method of treating a condition associated with aberrant expression of FGFR3, comprising selecting a patient diagnosed with said condition and administering to said patient the oligonucleotide according to claim 1 or claim 3.

12. A pharmaceutical composition comprising the oligonucleotide according to claim 1 or claim 3 and a pharmaceutically acceptable diluent, carrier, solvent, salt or adjuvant.

13. A method of reducing the expression of FGFR3 mRNA comprising delivering the conjugate comprising the oligonucleotide according to claim 1 or claim 3 and at least one non-nucleotide moiety covalently attached to said oligonucleotide to a cell or tissue comprising FGFR3 mRNA, under conditions appropriate for hybridization of said FGFR3 mRNA with said oligonucleotide, thereby reducing the expression of the FGFR3 mRNA.

14. A pharmaceutical composition comprising the conjugate according to claim 8 and a pharmaceutically acceptable diluent, carrier, solvent, salt or adjuvant.

* * * * *

UNITED STATES PATENT AND TRADEMARK OFFICE
CERTIFICATE OF CORRECTION

PATENT NO. : 9,725,723 B2
APPLICATION NO. : 14/647430
DATED : August 8, 2017
INVENTOR(S) : Maj Hedtjärn and Soren Ottosen Page 1 of 1

It is certified that error appears in the above-identified patent and that said Letters Patent is hereby corrected as shown below:

In the Claims

Column 81, Line 47, Claim 2, delete "14-18" and insert -- 12-18 --

Column 82, Line 48, Claim 10, after "according" insert -- to --

Signed and Sealed this
Eighth Day of May, 2018

Andrei Iancu
*Director of the United States Patent and Trademark Office*

SEQUENCE LISTING

<160> NUMBER OF SEQ ID NOS: 25

<210> SEQ ID NO 1
<211> LENGTH: 4304
<212> TYPE: DNA
<213> ORGANISM: Homo sapiens

<400> SEQUENCE: 1

```
gtcgcgggca gctggcgccg cgcggtcctg ctctgccggt cgcacggacg caccggcggg    60
ccgccggccg gagggacggg gcgggagctg ggcccgcgga cagcgagccg gagcgggagc   120
cgcgcgtagc gagccgggct ccggcgctcg ccagtctccc gagcggcgcc cgcctcccgc   180
cggtgcccgc gccgggccgt ggggggcagc atgcccgcgc gcgctgcctg aggacgccgc   240
```

```
ggcccccgcc cccgccatgg gcgccctgc ctgcgccctc gcgctctgcg tggccgtggc    300
catcgtggcc ggcgcctcct cggagtcctt ggggacggag cagcgcgtcg tggggcgagc    360
ggcagaagtc ccgggcccag agcccggcca gcaggagcag ttggtcttcg gcagcgggga    420
tgctgtggag ctgagctgtc ccccgccggg ggtggtccc atggggccca ctgtctgggt     480
caaggatggc acagggctgg tgccctcgga gcgtgtcctg gtggggcccc agcggctgca    540
ggtgctgaat gcctcccacg aggactccgg ggcctacagc tgccggcagc ggctcacgca    600
gcgcgtactg tgccacttca gtgtgcgggt gacagacgct ccatcctcgg gagatgacga    660
agacggggag gacgaggctg aggacacagg tgtggacaca ggggcccctt actggacacg    720
gcccgagcgg atggacaaga agctgctggc cgtgccggcc gccaacaccg tccgcttccg    780
ctgcccagcc gctggcaacc ccactccctc catctcctgg ctgaagaacg gcagggagtt    840
ccgcggcgag caccgcattg gaggcatcaa gctgcggcat cagcagtgga gcctggtcat    900
ggaaagcgtg gtgccctcgg accgcggcaa ctacacctgc gtcgtggaga acaagtttgg    960
cagcatccgg cagacgtaca cgctggacgt gctggagcgc tccccgcacc ggcccatcct    1020
gcaggcgggg ctgccggcca accagacggc ggtgctgggc agcgacgtgg agttccactg    1080
caaggtgtac agtgacgcac agccccacat ccagtggctc aagcacgtgg aggtgaatgg    1140
cagcaaggtg ggcccggacg gcacaccct cgttaccgtg ctcaagacgg cgggcgctaa    1200
caccaccgac aaggagctag aggttctctc cttgcacaac gtcacctttg aggacgccgg    1260
ggagtacacc tgcctggcgg gcaattctat tgggttttct catcactctg cgtggctggt    1320
ggtgctgcca gccgaggagg agctggtgga ggctgacgag gcgggcagtg tgtatgcagg    1380
catcctcagc tacggggtgg gcttcttcct gttcatcctg gtggtggcgg ctgtgacgct    1440
ctgccgcctg cgcagccccc ccaagaaagg cctgggctcc ccaccgtgc acaagatctc     1500 ccgcttcccg ctcaagcgac aggtgtccct ggagtccaac cgtccatga gctccaacac     1560 accactggtg cgcatcgcaa ggctgtcctc aggggagggc cccacgctgg ccaatgtctc    1620
cgagctcgag ctgcctgccg accccaaatg ggagctgtct cgggcccggc tgaccctggg    1680 caagccccctt ggggagggct gcttcggcca ggtggtcatg gcggaggcca tcggcattga    1740
caaggaccgg gccgccaagc ctgtcaccgt agccgtgaag atgctgaaag acgatgccac    1800
tgacaaggac ctgtcggacc tggtgtctga gatggagatg atgaagatga tcggaaaaca    1860
caaaaacatc atcaacctgc tgggcgcctg cacgcagggc gggccctgt acgtgctggt     1920 ggagtacgcg gccaagggta acctgcggga gtttctgcgg gcgcggcggc cccgggcct    1980 ggactactcc ttcgacacct gcaagccgcc cgaggagcag ctcaccttca aggacctggt    2040
gtcctgtgcc taccaggtgg cccgggggcat ggagtacttg gcctcccaga agtgcatcca    2100
cagggacctg gctgcccgca atgtgctggt gaccgaggac aacgtgatga agatcgcaga    2160
cttcgggctg gccgggacg tgcacaacct cgactactac aagaagacaa ccaacggccg    2220 gctgccgtg aagtggatgg cgcctgaggc cttgtttgac cgagtctaca ctcaccagag     2280
tgacgtctgg tcctttgggg tcctgctctg ggagatcttc acgctggggg gctccccgta    2340
ccccggcatc cctgtggagg agctcttcaa gctgctgaag gagggccacc gcatggacaa    2400
gcccgccaac tgcacacacg acctgtacat gatcatgcgg gagtgctggc atgccgcgcc    2460
ctcccagagg cccaccttca gcagctggt ggaggacctg accgtgtcc ttaccgtgac       2520 gtccaccgac gagtacctgg acctgtcggc gcctttcgag cagtactccc cgggtggcca    2580
ggacaccccc agctccagct cctcaggga cgactccgtg tttgcccacg acctgctgcc    2640
```

```
cccggccccca cccagcagtg ggggctcgcg gacgtgaagg gccactggtc cccaacaatg    2700 tgagggtcc  ctagcagccc accctgctgc tggtgcacag ccactccccg gcatgagact    2760
cagtgcagat ggagagacag ctacacagag ctttggtctg tgtgtgtgtg tgtgcgtgtg    2820
tgtgtgtgtg tgtgcacatc cgcgtgtgcc tgtgtgcgtg cgcatcttgc ctccaggtgc    2880
agaggtaccc tgggtgtccc cgctgctgtg caacggtctc ctgactggtg ctgcagcacc    2940
gagggccctt tgttctgggg ggacccagtg cagaatgtaa gtgggccac  ccggtgggac    3000 ccccgtgggg cagggagctg ggcccgacat ggctccggcc tctgcctttg caccacggga    3060
catcacaggg tgggcctcgg cccctcccac acccaaagct gagcctgcag ggaagcccca    3120
catgtccagc accttgtgcc tggggtgtta gtggcaccgc ctccccacct ccaggctttc    3180
ccacttccca ccctgcccct cagagactga aattacgggt acctgaagat gggagccttt    3240 acctttatg  caaaaggttt attccggaaa ctagtgtaca tttctataaa tagatgctgt    3300
gtatatggta tatatacata tatatatata acatatatgg aagagaaaa  ggctggtaca    3360 acggaggcct gcgaccctgg gggcacagga ggcaggcatg gccctgggcg gggcgtgggg    3420
gggcgtggag ggaggcccca gggggtctca cccatgcaag cagaggacca gggcctttc   3480 tggcaccgca gttttgtttt aaaactggac ctgtatattt gtaaagctat ttatgggccc    3540
ctggcactct tgttcccaca ccccaacact tccagcattt agctggccac atggcggaga    3600
gttttaattt ttaacttatt gacaaccgag aaggtttatc ccgccgatag agggacggcc    3660
aagaatgtac gtccagcctg ccccggagct ggaggatccc ctccaagcct aaaaggttgt    3720
taatagttgg aggtgattcc agtgaagata ttttatttcc tttgtccttt ttcaggagaa    3780
ttagatttct ataggatttt tctttaggag atttatttttt tggacttcaa agcaagctgg    3840
tattttcata caaattcttc taattgctgt gtgtcccagg cagggagacg gtttccaggg    3900
aggggccggc cctgtgtgca ggttccgatg ttattagatg ttacaagttt atatatatct    3960
atatatataa tttattgagt ttttacaaga tgtatttgtt gtagacttaa cacttcttac    4020
gcaatgcttc tagagtttta tagcctggac tgctaccttt caaagcttgg agggaagccg    4080
tgaattcagt tggttcgttc tgtactgtta ctgggccctg agtctgggca gctgtccctt    4140
gcttgcctgc agggcatgg  ctcagggtgg tctcttcttg gggcccagtg catggtggcc    4200
agaggtgtca cccaaaccgg caggtgcgat tttgttaacc cagcgacgaa ctttccgaaa    4260
aataaagaca cctggttgct aacctggaaa aaaaaaaaa  aaaa                    4304
```

<210> SEQ ID NO 2
<211> LENGTH: 111
<212> TYPE: DNA
<213> ORGANISM: Homo sapiens

<400> SEQUENCE: 2

```
gcatcctcag ctacggggtg ggcttcttcc tgttcatcct ggtggtggcg gctgtgacgc      60
tctgccgcct gcgcagcccc cccaagaaag gcctgggctc ccccaccgtg c             111
```

<210> SEQ ID NO 3
<211> LENGTH: 26
<212> TYPE: DNA
<213> ORGANISM: Homo sapiens

<400> SEQUENCE: 3

```
gcatcctcag ctacggggtg ggcttc                                           26
```

<210> SEQ ID NO 4
<211> LENGTH: 4304
<212> TYPE: DNA
<213> ORGANISM: Homo sapiens

<400> SEQUENCE: 4

| | | | | | |
|---|---|---|---|---|---|
| gtcgcgggca | gctggcgccg | cgcggtcctg | ctctgccggt | cgcacggacg | caccggcggg | 60 |
| ccgccggccg | gagggacggg | gcgggagctg | ggcccgcgga | cagcgagccg | gagcgggagc | 120 |
| cgcgcgtagc | gagccgggct | ccggcgctcg | ccagtctccc | gagcggcgcc | cgcctcccgc | 180 |
| cggtgcccgc | gccgggccgt | gggggcagc | atgcccgcgc | gcgctgcctg | aggacgccgc | 240 |
| ggccccgcc | cccgccatgg | gcgcccctgc | ctgcgccctc | gcgctctgcg | tggccgtggc | 300 |
| catcgtggcc | ggcgcctcct | cggagtcctt | ggggacggag | cagcgcgtcg | tggggcgagc | 360 |
| ggcagaagtc | ccgggcccag | agcccggcca | gcaggagcag | ttggtcttcg | gcagcgggga | 420 |
| tgctgtggag | ctgagctgtc | ccccgcccgg | ggtggtccc | atgggggccca | ctgtctgggt | 480 |
| caaggatggc | acagggctgg | tgccctcgga | gcgtgtcctg | gtgggccccc | agcggctgca | 540 |
| ggtgctgaat | gcctcccacg | aggactccgg | ggcctacagc | tgccggcagc | ggctcacgca | 600 |
| gcgcgtactg | tgccacttca | gtgtgcgggt | gacagacgct | ccatcctcgg | gagatgacga | 660 |
| agacgggag | gacgaggctg | aggacacagg | tgtggacaca | ggggcccctt | actggacacg | 720 |
| gcccgagcgg | atggacaaga | agctgctggc | cgtgccggcc | gccaacaccg | tccgcttccg | 780 |
| ctgcccagcc | gctggcaacc | ccactccctc | catctcctgg | ctgaagaacg | gcagggagtt | 840 |
| ccgcggcgag | caccgcattg | gaggcatcaa | gctgcggcat | cagcagtgga | gcctggtcat | 900 |
| ggaaagcgtg | gtgccctcgg | accgcggcaa | ctacacctgc | gtcgtggaga | caagtttgg | 960 |
| cagcatccgg | cagacgtaca | cgctggacgt | gctggagcgc | tccccgcacc | ggcccatcct | 1020 |
| gcaggcgggg | ctgccggcca | accagacggc | ggtgctgggc | agcgacgtgg | agttccactg | 1080 |
| caaggtgtac | agtgacgcac | agccccacat | ccagtggctc | aagcacgtgg | aggtgaatgg | 1140 |
| cagcaaggtg | ggcccggacg | gcacacccta | cgttaccgtg | ctcaagacgg | cgggcgctaa | 1200 |
| caccaccgac | aaggagctag | aggttctctc | cttgcacaac | gtcacctttg | aggacgccgg | 1260 |
| ggagtacacc | tgcctggcgg | gcaattctat | tgggttttct | catcactctg | cgtggctggt | 1320 |
| ggtgctgcca | gccgaggagg | agctggtgga | ggctgacgag | gcgggcagtg | tgtatgcagg | 1380 |
| catcctcagc | tacagggtgg | gcttcttcct | gttcatcctg | gtggtggcgg | ctgtgacgct | 1440 |
| ctgccgcctg | cgcagccccc | ccaagaaagg | cctgggctcc | ccaccgtgc | acaagatctc | 1500 |
| ccgcttcccg | ctcaagcgac | aggtgtccct | ggagtccaac | gcgtccatga | gctccaacac | 1560 |
| accactggtg | cgcatcgcaa | ggctgtcctc | aggggagggc | cccacgctgg | ccaatgtctc | 1620 |
| cgagctcgag | ctgcctgccg | accccaaatg | ggagctgtct | cgggcccggc | tgaccctggg | 1680 |
| caagcccctt | ggggagggct | gcttcggcca | ggtggtcatg | gcgaggcca | tcggcattga | 1740 |
| caaggaccgg | gccgccaagc | ctgtcaccgt | agccgtgaag | atgctgaaag | acgatgccac | 1800 |
| tgacaaggac | ctgtcggacc | tggtgtctga | gatggagatg | atgaagatga | tcgggaaaca | 1860 |
| caaaaacatc | atcaacctgc | tgggcgcctg | cacgcagggc | gggcccctgt | acgtgctggt | 1920 |
| ggagtacgcg | gccaagggta | acctgcggga | gtttctgcgg | gcgcggcggc | cccgggcct | 1980 |
| ggactactcc | ttcgacaccct | gcaagccgcc | cgaggagcag | ctcaccttca | aggacctggt | 2040 |
| gtcctgtgcc | taccaggtgg | cccggggcat | ggagtacttg | gcctcccaga | gtgcatcca | 2100 |
| cagggacctg | gctgcccgca | atgtgctggt | gaccgaggac | aacgtgatga | agatcgcaga | 2160 |

```
cttcgggctg gcccgggacg tgcacaacct cgactactac aagaagacaa ccaacggccg   2220
gctgcccgtg aagtggatgg cgcctgaggc cttgtttgac cgagtctaca ctcaccagag   2280
tgacgtctgg tcctttgggg tcctgctctg ggagatcttc acgctggggg gctccccgta   2340 cccccggcatc cctgtggagg agctcttcaa gctgctgaag gagggccacc gcatggacaa   2400
gcccgccaac tgcacacacg acctgtacat gatcatgcgg gagtgctggc atgccgcgcc   2460
ctcccagagg cccaccttca agcagctggt ggaggacctg accgtgtcc ttaccgtgac   2520 gtccaccgac gagtacctgg acctgtcggc gcctttcgag cagtactccc cgggtggcca   2580
ggacaccccc agctccagct cctcagggga cgactccgtg tttgcccacg acctgctgcc   2640
cccggcccca cccagcagtg ggggctcgcg gacgtgaagg gccactggtc cccaacaatg   2700
tgaggggtcc ctagcagccc accctgctgc tggtgcacag ccactccccg gcatgagact   2760
cagtgcagat ggagagacag ctacacagag ctttggtctg tgtgtgtgtg tgtgcgtgtg   2820
tgtgtgtgtg tgtgcacatc cgcgtgtgcc tgtgtgcgtg cgcatcttgc ctccaggtgc   2880
agaggtaccc tgggtgtccc cgctgctgtg caacggtctc ctgactggtg ctgcagcacc   2940 gaggggccctt tgttctgggg ggacccagtg cagaatgtaa gtgggcccac ccggtgggac   3000
ccccgtgggg cagggagctg ggcccgacat ggctccggcc tctgcctttg caccacggga   3060
catcacaggg tgggcctcgg cccctcccac acccaaagct gagcctgcag ggaagcccca   3120
catgtccagc accttgtgcc tggggtgtta gtggcaccgc ctccccacct ccaggctttc   3180
ccacttccca ccctgcccct cagagactga aattacgggt acctgaagat gggagccttt   3240
accttttatg caaaaggttt attccggaaa ctagtgtaca tttctataaa tagatgctgt   3300
gtatatggta tatatacata tatatatata acatatatgg aagaggaaaa ggctggtaca   3360
acggaggcct gcgaccctgg gggcacagga ggcaggcatg gccctgggcg gggcgtgggg   3420
gggcgtggag ggaggcccca gggggtctca cccatgcaag cagaggacca gggccttttc   3480
tggcaccgca gttttgtttt aaaactggac ctgtatattt gtaaagctat ttatgggccc   3540
ctggcactct tgttcccaca ccccaacact tccagcattt agctggccac atggcggaga   3600 gtttttaattt ttaacttatt gacaaccgag aaggtttatc ccgccgatag agggacggcc   3660
aagaatgtac gtccagcctg ccccggagct ggaggatccc ctccaagcct aaaaggttgt   3720
taatagttgg aggtgattcc agtgaagata ttttatttcc tttgtccttt ttcaggagaa   3780
ttagatttct ataggatttt tctttaggag atttatttttt tggacttcaa agcaagctgg   3840 tatttttcata caaattcttc taattgctgt gtgtcccagg cagggagacg gtttccaggg   3900
aggggccggc cctgtgtgca ggttccgatg ttattagatg ttacaagttt atatatatct   3960
atatatataa tttattgagt ttttacaaga tgtatttgtt gtagacttaa cacttcttac   4020
gcaatgcttc tagagtttta tagcctggac tgctaccttt caaagcttgg agggaagccg   4080
tgaattcagt tggttcgttc tgtactgtta ctgggccctg agtctgggca gctgtccctt   4140
gcttgcctgc agggccatgg ctcagggtgg tctcttcttg gggcccagtg catggtggcc   4200
agaggtgtca cccaaaccgg caggtgcgat tttgttaacc cagcgacgaa ctttccgaaa   4260
aataaagaca cctggttgct aacctggaaa aaaaaaaaaa aaaa               4304
```

<210> SEQ ID NO 5
<211> LENGTH: 111
<212> TYPE: DNA
<213> ORGANISM: Homo sapiens

```
<400> SEQUENCE: 5
gcatcctcag ctacagggtg ggcttcttcc tgttcatcct ggtggtggcg gctgtgacgc    60
tctgccgcct gcgcagcccc cccaagaaag gcctgggctc ccccaccgtg c            111

<210> SEQ ID NO 6
<211> LENGTH: 25
<212> TYPE: DNA
<213> ORGANISM: Homo sapiens

<400> SEQUENCE: 6
catcctcagc tacagggtgg gcttc                                          25

<210> SEQ ID NO 7
<211> LENGTH: 2887
<212> TYPE: DNA
<213> ORGANISM: Mus musculus

<400> SEQUENCE: 7
ccggcggggg gactcagtgg tgggcggccg gcactgggac agaggagacc ctggaaaagc    60
gggccgagag acggagccgc gcgtggtgag ttgggctcta gcggccgcca gtctccacag   120
aggcgttctc ccaccggcgc cggagccgcg tgggggttg cagcatgccc gcgcgcgctg    180
cttgaggacg ccgcggcccc cgctctggag ccatggtagt cccggcctgc gtgctagtgt   240
tctgcgtggc ggtcgtggct ggagctactt ccgagcctcc tggtccagag cagcgagttg   300
tgcggagagc ggcagaggtt ccagggcctg aacctagcca gcaggagcag gtggccttcg   360
gcagtgggga caccgtggag ctgagctgcc atcctcctgg aggtgccccc acagggccca   420
cggtctgggc taaggatggt acaggtctgg tggcctccca ccgcatcctg gtggggcctc   480
agaggctgca agtgctaaat gcctcccacg aagatgcagg ggtctacagc tgccagcacc   540
ggctcactcg gcgtgtgctg tgccacttca gtgtgcgtgt aacagatgct ccatcctcag   600
gagatgacga agatgggag gacgtggctg aagacacagg ggctccttat tggactcgcc   660
cggagcgaat ggataagaaa ctgctggctg tgccagccgc aaacactgtc cgcttccgct   720
gcccagctgc tggcaaccct accccctcca tctcctggct gaagaatggc aaagaattcc   780
gagggcagca tcgcattggg ggcatcaagc tccggcacca gcagtggagc ttggtcatgg   840
aaagtgtggt accctccgat cgtggcaact atacctgtgt agttgagaac aagtttggca   900
gcatccggca gacatacaca ctggatgtgc tggagcgctc ccacaccgg cccatcctgc    960 aggctgggct gccggccaac cagacagcca ttctaggcag tgacgtggag ttccactgca  1020
aggtgtacag cgatgcacag ccacacatcc agtggctgaa gcacgtggaa gtgaacggca  1080
gcaaggtggg ccctgacggc acgcctacg acactgtact caagactgca ggcgctaaca  1140
ccaccgacaa ggagctagag gttctgtcct tgcacaatgt caccttgag acgcgggggg   1200 agtacacctg cctggcgggc aattctattg gttttcccca tcactctgcg tggctggtgg  1260
tgctgccagc tgaggaggag ctgatggaaa ctgatgaggc tggcagcgtg tacgcaggcg  1320
tcctcagcta cggggtggtc ttcttcctct tcatcctggt ggtggcagct gtgatactct  1380
gccgcctgcg cagtccccca agaagggct tgggctcgcc caccgtgcac aaggtctctc  1440
gcttcccgct taagcgacag gtgtccttgg aatctaactc ctctatgaac tccaacacac  1500
cccttgtccg gattgcccgg ctgtcctcag gagaaggtcc tgttctggcc aatgtttctg  1560
aacttgagct gcctgctgac cccaagtggg agctatccag gacccggctg acacttggta  1620
agcctcttgg agaaggctgc tttggacagg tggtcatggc agaagctatt ggcatcgaca  1680
```

-continued

| | |
|---|---|
| aggaccgtac tgccaagcct gtcaccgtgg ccgtgaagat gctgaaagat gatgcgactg | 1740 |
| acaaggacct gtcggacctg gtatctgaga tggagatgat gaaaatgatt ggcaagcaca | 1800 |
| agaacatcat taacctgctg ggggcgtgca cacagggtgg gcccctgtat gtgctggtgg | 1860 |
| agtacgcagc caagggcaat ctccgggagt tccttcgggc gcggcggcct ccaggcatgg | 1920 |
| actactcctt tgatgcctgc aggctgccag aggaacagct cacctgcaag gatctagtgt | 1980 |
| cctgtgccta ccaggtggca cggggcatgg aatacttggc ttctcagaag tgtattcaca | 2040 |
| gagacttggc tgccagaaac gtcctggtga ccgaggacaa tgtgatgaag attgcggact | 2100 |
| ttggcctggc tcgagatgtg cacaacctgg actactacaa gaagaccaca aatggccggc | 2160 |
| tacctgtgaa gtggatggca ccagaggccc ttttttgaccg agtctacacc caccagagtg | 2220 |
| atgtttggtc ttttggtgtc ctcctctggg agatctttac gctgggggc tcaccgtacc | 2280 |
| ctggcatccc agtggaagag cttttcaagc tgttgaaaga gggccaccgc atggacaagc | 2340 |
| cagccagctg cacacatgac ctgtacatga tcatgcggga atgttggcat gcggtgcctt | 2400 |
| cacagaggcc caccttcaag cagttggtag aggatttaga ccgcatcctc actgtgacat | 2460 |
| caaccgacga gtacttggac ctctccgtgc cgtttgagca gtactcgcca ggtggccagg | 2520 |
| acacgcctag ctccagctcg tccggagatg actcggtgtt cacccatgac ctgctacccc | 2580 |
| caggtccacc cagtaacggg ggacctcgga cgtgaagggc caacagtccc acagaccaag | 2640 |
| ccccaggcaa tgtttaccgg accctagccc gccctgctac tgctggtgtg cagtggaccc | 2700 |
| tagccagccc agtgcaatgg gccaacagta gacaagactt cctgcgtgtt tatccttggc | 2760 |
| tcctgggtgc agaggccctt gggaacatgc actgctgtag agtaatctcc tgactggcca | 2820 |
| gggccaggag caccaaacaa gaatgtaaga ggcccaccct gtgcaaccct ggggttctgg | 2880 |
| cccctct | 2887 |

<210> SEQ ID NO 8
<211> LENGTH: 3187
<212> TYPE: DNA
<213> ORGANISM: Rattus norvegicus
<220> FEATURE:
<221> NAME/KEY: misc_feature
<222> LOCATION: (246)..(246)
<223> OTHER INFORMATION: n is a, c, g, or t

<400> SEQUENCE: 8

| | |
|---|---|
| atggtagtcc cggcctgcgt gctagtgttc tgcgtggcgg tcgtggctgg agttacttcc | 60 |
| gagcctcccg gtccagagca gcgagttggt cggagagcgg cagaggttcc agggcctgaa | 120 |
| cctagccagc aggagcaggt ggccttcggc agtggggaca ctgtggagct gagctgccat | 180 |
| ccgcctggag gtgcccccac aggccccact ctctgggcta aggacggtgt ggggctggtg | 240 |
| gcctcncacc gtatcctggt ggggcctcag aggcttcaag tgctaaacgc cacccatgag | 300 |
| gatgctgggg tctacagctg ccagcagcgg ctaacccggc gtgtgctgtg ccactttagt | 360 |
| gtgcgtgtaa cagatgctcc gtcctcagga gatgacgaag atggggagga cgtggctgaa | 420 |
| gacacagggg ctccttactg gactcgaccg gagcgtatgg ataagaaact gctggctgtg | 480 |
| ccagctgcaa acactgtacg cttccgctgc ccagctgctg gcaaccccac ccctccatc | 540 |
| ccctggctga agaacggcaa agaattccga ggggagcacc gcattggggg cattaagctc | 600 |
| cggcaccagc agtggagctt ggtcatggaa agtgtggtgc cctctgaccg cggcaattac | 660 |
| acctgcgtgg ttgagaacaa gtttggcagc atccggcaga cgtacacccc tggatgtgctg | 720 |

```
gagcgctccc cacaccggcc catcctgcag gctgggctgc cagccaacca gacagccgtt    780
ctgggcagtg acgtggagtt ccactgcaag gtgtacagcg acgcacagcc acacatccag    840
tggctgaagc acgtggaggt gaatgggagc aaggtgggcc ctgacggcac gccctacgtc    900
actgtactca agactgcagg agctaacacc accgacaggg agctagaggt tctgtccttg    960
cacaatgtca cctttgagga tgcggggag tacacctgcc tggcgggcaa ttctatcggg   1020
ttttcccatc actctgcgtg gctggtggtg ctgccagccg aggaggagct gatggaagtt   1080
gacgaggctg gcagcgtgta cgcgggtgtc ctcagctacg gggtgggctt cttcctcttc   1140
atcctggtgg tggcggcagt gacgctctgc cgtctgcgca gtcccccaaa gaagggcctg   1200
ggctcgccca ccgtgcacaa ggtctctcgc ttcccgctta agcacaggt gtccttggag    1260 tctaattcct ctatgaactc caacacacct ctcgtccgga ttgcccggct gtcctcagga   1320
gaaggtcctg tcctggccaa tgtttctgaa cttgagctgc ctgctgaccc caagtgggag   1380
ctatccagga cccggctgac actcggtaag cctcttggag aaggctgctt tggacaggtt   1440
gtcatggcag aagctattgg catcgacaag gaccgcactg ccaagcctgt caccgtggcc   1500
gtgaagatgc tgaaagatga tgcgactgac aaggacctgt cggacctggt gtctgagatg   1560
gagatgatga aaatgattgg caagcacaag aacatcatta acctgttggg ggcctgcacc   1620
cagggtgggc cctgtatgt gctggtggag tatgcagcca agggcaacct gcgagagttc   1680
ctccgggcac ggcggcctcc aggcatggat tactcctttg atgcctgcag gctgccagag   1740
gaacagctca cctgcaagga tctggtgtcc tgtgcctacc aggtggcacg gggcatggag   1800
tacttggctt cccagaagtg tattcacaga gacctggctg ccagaaacgt gctggtgact   1860
gaggacaatg tgatgaagat tgcagacttt ggcctggccc gagatgtgca acctggat    1920 tactacaaga gaccacaaa tggccggcta cctgtgaagt ggatggcacc agaggccctt   1980
tttgaccgag tctacaccca tcagagtgat gtctggtcct ttggtgtcct cctctgggag   2040
atctttacac tgggtgggtc accatatcct ggcatcccag tggaagagct tttcaagctg   2100
ttgaaagagg ccaccgcat ggacaagcca gccaactgca cacatgacct gtacatgatc   2160
atgcgggaat gttggcatgc agtgccttca cagaggccca ccttcaagca gttggtagag   2220
gatttagacc gcatcctcac ggtgacatca actgacgagt acttggacct ctcggtgcca   2280
tttgaacagt actcgccagg tggccaagat actcctagct ccagctcgtc cggggacgac   2340
tctgtgttca cccatgacct gctacccca ggcccaccca gcaatggggg acctcggacg   2400
tgaagggccg acagtcccac agaccaagcc ccagccaatg tttacgcgga ccctagcccg   2460
ccctgctact gctggtgtgc agtggaccct agccagccca gcgcaatggg ccagcaatag   2520
acaagacttc ctgcgtgttt atccttggct cctgggtgca gaggcccctg ggaacatgt    2580 actgctgtag aatgatctcc tgactggcca gggccaggag caccaaatga aatgtaaga    2640 gggcccccc gccctgtgc gacagtgggg ttctggctcc ctcactcccc actgctacct   2700
tacagggacc gttgtagaga gggctggact tcatgtccag ggtgggcctt ggcctttttg   2760
gtgcccaaag ctgagcctgt agggaggctc tgctcttatg tggcaagcct ctctcctaca   2820
tggcaccttg tgcctgggt gagtcatagc tcgacacctc caggctgccc gcttcccatc   2880
ctgtccctca aattacgggt acctgaaggg ggggtggcca taacttctat cagaaaggtt   2940
tattccagag gaaaatgtac atttatataa atagatgttg tgtatgatat atagatat    3000 atacatacat atatataaga atatctatat ggaaaaggc aaagctgagg cccaaggag    3060 caagacaccc catggggctc accagtgaga tggcacaggc aggccgagaa gcaggggcct   3120
```

```
tgtctggcat tgcagtgttg tttgtatctg gacctgtata tttgtaaagc tatttatcaa    3180
ccctcgg                                                                3187

<210> SEQ ID NO 9
<211> LENGTH: 16
<212> TYPE: DNA
<213> ORGANISM: Artificial
<220> FEATURE:
<223> OTHER INFORMATION: Oligonucleotide sequence motif

<400> SEQUENCE: 9
ctgtagctga ggatgc                                                      16

<210> SEQ ID NO 10
<211> LENGTH: 15
<212> TYPE: DNA
<213> ORGANISM: Artificial
<220> FEATURE:
<223> OTHER INFORMATION: Oligonucleotide sequence motif

<400> SEQUENCE: 10
gaagcccacc ctgta                                                       15

<210> SEQ ID NO 11
<211> LENGTH: 16
<212> TYPE: DNA
<213> ORGANISM: Artificial
<220> FEATURE:
<223> OTHER INFORMATION: Oligonucleotide sequence motif

<400> SEQUENCE: 11
gaagaagccc accctg                                                      16

<210> SEQ ID NO 12
<211> LENGTH: 14
<212> TYPE: DNA
<213> ORGANISM: Artificial
<220> FEATURE:
<223> OTHER INFORMATION: Oligonucleotide sequence motif

<400> SEQUENCE: 12
aagaagccca ccct                                                        14

<210> SEQ ID NO 13
<211> LENGTH: 15
<212> TYPE: DNA
<213> ORGANISM: Artificial
<220> FEATURE:
<223> OTHER INFORMATION: Oligonucleotide sequence motif

<400> SEQUENCE: 13
gaagaagccc accct                                                       15

<210> SEQ ID NO 14
<211> LENGTH: 12
<212> TYPE: DNA
<213> ORGANISM: artificial
<220> FEATURE:
<223> OTHER INFORMATION: Oligonucleotide sequence motif

<400> SEQUENCE: 14
gaagcccacc ct                                                          12

<210> SEQ ID NO 15
```

-continued

```
<210> SEQ ID NO 15
<211> LENGTH: 16
<212> TYPE: RNA
<213> ORGANISM: Homo sapiens

<400> SEQUENCE: 15
gcauccucag cuacag                                                    16

<210> SEQ ID NO 16
<211> LENGTH: 15
<212> TYPE: RNA
<213> ORGANISM: Homo sapiens

<400> SEQUENCE: 16
uacagggugg gcuuc                                                     15

<210> SEQ ID NO 17
<211> LENGTH: 16
<212> TYPE: RNA
<213> ORGANISM: Homo sapiens

<400> SEQUENCE: 17
cagggugggc uucuuc                                                    16

<210> SEQ ID NO 18
<211> LENGTH: 14
<212> TYPE: RNA
<213> ORGANISM: Homo sapiens

<400> SEQUENCE: 18
agggugggcu ucuu                                                      14

<210> SEQ ID NO 19
<211> LENGTH: 15
<212> TYPE: RNA
<213> ORGANISM: Homo sapiens

<400> SEQUENCE: 19
agggugggcu ucuuc                                                     15

<210> SEQ ID NO 20
<211> LENGTH: 12
<212> TYPE: RNA
<213> ORGANISM: Homo sapiens

<400> SEQUENCE: 20
agggugggcu uc                                                        12

<210> SEQ ID NO 21
<211> LENGTH: 16
<212> TYPE: DNA
<213> ORGANISM: Artificial
<220> FEATURE:
<223> OTHER INFORMATION: LNA antisense oligomer
<220> FEATURE:
<221> NAME/KEY: misc_feature
<222> LOCATION: (1)..(16)
<223> OTHER INFORMATION: Phosphorothioate internucleoside linkages
<220> FEATURE:
<221> NAME/KEY: misc_feature
<222> LOCATION: (1)..(3)
<223> OTHER INFORMATION: LNA nucleosides, such as beta-D-oxy LNA
<220> FEATURE:
<221> NAME/KEY: misc_feature
<222> LOCATION: (1)..(1)
<223> OTHER INFORMATION: 5 methyl cytosine LNA
<220> FEATURE:
<221> NAME/KEY: misc_feature
```

```
<222> LOCATION: (14)..(6)
<223> OTHER INFORMATION: LNA nucleosides, such as beta-D-oxy LNA
<220> FEATURE:
<221> NAME/KEY: misc_feature
<222> LOCATION: (16)..(16)
<223> OTHER INFORMATION: 5 methyl cytosine LNA

<400> SEQUENCE: 21
ctgtagctga ggatgc                                                    16

<210> SEQ ID NO 22
<211> LENGTH: 15
<212> TYPE: DNA
<213> ORGANISM: Artificial
<220> FEATURE:
<223> OTHER INFORMATION: LNA antisense oligomer
<220> FEATURE:
<221> NAME/KEY: misc_feature
<222> LOCATION: (1)..(15)
<223> OTHER INFORMATION: Phosphorothioate internucleoside linkages
<220> FEATURE:
<221> NAME/KEY: misc_feature
<222> LOCATION: (1)..(3)
<223> OTHER INFORMATION: LNA nucleosides, such as beta-D-oxy LNA
<220> FEATURE:
<221> NAME/KEY: misc_feature
<222> LOCATION: (13)..(15)
<223> OTHER INFORMATION: LNA nucleosides, such as beta-D-oxy LNA

<400> SEQUENCE: 22
gaagcccacc ctgta                                                     15

<210> SEQ ID NO 23
<211> LENGTH: 16
<212> TYPE: DNA
<213> ORGANISM: Artificial
<220> FEATURE:
<223> OTHER INFORMATION: LNA antisense oligomer
<220> FEATURE:
<221> NAME/KEY: misc_feature
<222> LOCATION: (1)..(16)
<223> OTHER INFORMATION: Phosphorothioate internucleoside linkages
<220> FEATURE:
<221> NAME/KEY: misc_feature
<222> LOCATION: (1)..(3)
<223> OTHER INFORMATION: LNA nucleosides, such as beta-D-oxy LNA
<220> FEATURE:
<221> NAME/KEY: misc_feature
<222> LOCATION: (14)..(16)
<223> OTHER INFORMATION: LNA nucleosides, such as beta-D-oxy LNA
<220> FEATURE:
<221> NAME/KEY: misc_feature
<222> LOCATION: (14)..(14)
<223> OTHER INFORMATION: 5 methyl cytosine LNA

<400> SEQUENCE: 23
gaagaagccc accctg                                                    16

<210> SEQ ID NO 24
<211> LENGTH: 14
<212> TYPE: DNA
<213> ORGANISM: Artificial
<220> FEATURE:
<223> OTHER INFORMATION: LNA antisense oligomer
<220> FEATURE:
<221> NAME/KEY: misc_feature
<222> LOCATION: (1)..(14)
<223> OTHER INFORMATION: Phosphorothioate internucleoside linkages
<220> FEATURE:
<221> NAME/KEY: misc_feature
<222> LOCATION: (1)..(3)
<223> OTHER INFORMATION: LNA nucleosides, such as beta-D-oxy LNA
<220> FEATURE:
```

```
<221> NAME/KEY: misc_feature
<222> LOCATION: (12)..(14)
<223> OTHER INFORMATION: LNA nucleosides, such as beta-D-oxy LNA
<220> FEATURE:
<221> NAME/KEY: misc_feature
<222> LOCATION: (12)..(13)
<223> OTHER INFORMATION: 5 methyl cytosine LNA

<400> SEQUENCE: 24
aataatccca ccct                                                              14

<210> SEQ ID NO 25
<211> LENGTH: 15
<212> TYPE: DNA
<213> ORGANISM: Artificial
<220> FEATURE:
<223> OTHER INFORMATION: LNA antisense oligomer
<220> FEATURE:
<221> NAME/KEY: misc_feature
<222> LOCATION: (1)..(15)
<223> OTHER INFORMATION: Phosphorothioate internucleoside linkages
<220> FEATURE:
<221> NAME/KEY: misc_feature
<222> LOCATION: (1)..(3)
<223> OTHER INFORMATION: LNA nucleosides, such as beta-D-oxy LNA
<220> FEATURE:
<221> NAME/KEY: misc_feature
<222> LOCATION: (13)..(15)
<223> OTHER INFORMATION: LNA nucleosides, such as beta-D-oxy LNA
<220> FEATURE:
<221> NAME/KEY: misc_feature
<222> LOCATION: (13)..(14)
<223> OTHER INFORMATION: 5 methyl cytosine LNA

<400> SEQUENCE: 25
gaagaagccc accct                                                             15
```